(12) United States Patent
Hegyi

(10) Patent No.: US 11,611,735 B2
(45) Date of Patent: Mar. 21, 2023

(54) OPEN VIEW, MULTI-MODAL, CALIBRATED DIGITAL LOUPE WITH DEPTH SENSING

(71) Applicant: PHOTONIC MEDICAL INC., Palo Alto, CA (US)

(72) Inventor: Alex Hegyi, San Francisco, CA (US)

(73) Assignee: Photonic Medical Inc., Palo Alto, CA (US)

( * ) Notice: Subject to any disclaimer, the term of this patent is extended or adjusted under 35 U.S.C. 154(b) by 0 days.

(21) Appl. No.: 17/491,006

(22) Filed: Sep. 30, 2021

(65) Prior Publication Data
US 2022/0038675 A1    Feb. 3, 2022

Related U.S. Application Data

(63) Continuation of application No. 17/156,217, filed on Jan. 22, 2021, now Pat. No. 11,166,006.
(Continued)

(51) Int. Cl.
*H04N 13/00*      (2018.01)
*H04N 13/246*   (2018.01)
(Continued)

(52) U.S. Cl.
CPC ........... *H04N 13/246* (2018.05); *A61B 90/35* (2016.02); *A61B 90/361* (2016.02); *A61B 90/37* (2016.02);
(Continued)

(58) Field of Classification Search
CPC .. H04N 13/344; H04N 13/254; H04N 13/239; H04N 13/398; H04N 5/23299;
(Continued)

(56) References Cited

U.S. PATENT DOCUMENTS

| 4,763,968 A | 8/1988 | Minami et al. |
| 4,907,296 A * | 3/1990 | Blecha .................. A42B 3/042 |
| | | 2/6.2 |

(Continued)

FOREIGN PATENT DOCUMENTS

| CA | 2339880 C | 11/2004 |
| CA | 2905427 A1 | 10/2014 |
| CA | 2692368 C | 9/2016 |
| CA | 3021561 A1 | 11/2017 |
| CN | 2781417 Y | 5/2006 |
| CN | 101610354 A | 12/2009 |
| CN | 102247209 A | 11/2011 |
| CN | 102697563 A | 10/2012 |

(Continued)

OTHER PUBLICATIONS

US 9,492,073 B2, 11/2016, Tesar et al. (withdrawn)
(Continued)

*Primary Examiner* — Frank F Huang
(74) *Attorney, Agent, or Firm* — Shay Glenn LLP

(57) ABSTRACT

A digital loupe system is provided which can include a number of features. In one embodiment, the digital loupe system can include a stereo camera pair and a distance sensor. The system can further include a processor configured to perform a transformation to image signals from the stereo camera pair based on a distance measurement from the distance sensor and from camera calibration information. In some examples, the system can use the depth information and the calibration information to correct for parallax between the cameras to provide a multi-channel image. Ergonomic head mounting systems are also provided. In some implementations, the head mounting systems can be configurable to support the weight of a digital loupe system, including placing one or two oculars in a line of sight with an eye of a user, while improving overall ergonomics, including peripheral vision, comfort, stability, and adjustability. Methods of use are also provided.

21 Claims, 18 Drawing Sheets

Related U.S. Application Data

(60) Provisional application No. 62/964,287, filed on Jan. 22, 2020.

(51) Int. Cl.

| | |
|---|---|
| H04N 13/344 | (2018.01) |
| G09G 5/10 | (2006.01) |
| H04N 9/04 | (2006.01) |
| G06T 7/50 | (2017.01) |
| H04N 9/64 | (2023.01) |
| H04N 5/225 | (2006.01) |
| H04N 5/235 | (2006.01) |
| G01C 3/14 | (2006.01) |
| A61B 90/00 | (2016.01) |
| A61B 90/35 | (2016.01) |
| H04N 13/239 | (2018.01) |
| A61B 90/53 | (2016.01) |
| H04N 13/254 | (2018.01) |
| H04N 13/398 | (2018.01) |
| H04N 5/232 | (2006.01) |
| G02C 3/00 | (2006.01) |
| A61B 5/00 | (2006.01) |
| A61B 90/50 | (2016.01) |

(52) U.S. Cl.
CPC .......... *A61B 90/53* (2016.02); *G01C 3/14* (2013.01); *G02C 3/003* (2013.01); *G06T 7/50* (2017.01); *G09G 5/10* (2013.01); *H04N 5/2253* (2013.01); *H04N 5/2256* (2013.01); *H04N 5/2354* (2013.01); *H04N 5/23299* (2018.08); *H04N 9/045* (2013.01); *H04N 9/646* (2013.01); *H04N 13/239* (2018.05); *H04N 13/254* (2018.05); *H04N 13/344* (2018.05); *H04N 13/398* (2018.05); *A61B 5/0075* (2013.01); *A61B 2090/3612* (2016.02); *A61B 2090/371* (2016.02); *A61B 2090/372* (2016.02); *A61B 2090/373* (2016.02); *A61B 2090/502* (2016.02); *A61B 2560/0247* (2013.01); *G09G 2320/0626* (2013.01); *G09G 2354/00* (2013.01); *G09G 2360/144* (2013.01); *H04N 2213/001* (2013.01); *H04N 2213/008* (2013.01)

(58) Field of Classification Search
CPC .......... H04N 5/2253; H04N 2213/001; H04N 2213/008; A61B 90/37; A61B 90/53; A61B 2090/371; A61B 2090/372; A61B 2090/502; G02C 3/003
See application file for complete search history.

(56) References Cited

U.S. PATENT DOCUMENTS

| | | | |
|---|---|---|---|
| 5,042,930 A | 8/1991 | Hutt | |
| 5,078,469 A | 1/1992 | Clark et al. | |
| 5,312,393 A | 5/1994 | Mastel | |
| 5,374,820 A | 12/1994 | Haaksman | |
| 5,695,492 A | 12/1997 | Brown | |
| 5,709,459 A | 1/1998 | Gourgouliatos et al. | |
| 5,856,811 A * | 1/1999 | Shih ............... G02B 27/0176 345/8 | |
| 5,971,540 A | 10/1999 | Ofner | |
| 6,005,710 A | 12/1999 | Pensel et al. | |
| 6,032,070 A | 2/2000 | Flock et al. | |
| 6,055,451 A | 4/2000 | Bambot et al. | |
| 6,255,650 B1 | 7/2001 | Warner et al. | |
| 6,884,980 B2 | 4/2005 | Spink | |
| 6,891,518 B2 | 5/2005 | Sauer et al. | |
| 7,234,824 B2 | 6/2007 | Langley | |
| 7,286,287 B1 | 10/2007 | Ofner | |
| 7,319,437 B2 | 1/2008 | Yamamoto | |
| 7,367,809 B2 | 5/2008 | Takahashi | |
| 7,426,258 B1 | 9/2008 | Zweig | |
| 7,554,723 B2 | 6/2009 | Moeller et al. | |
| 7,594,188 B2 | 9/2009 | Rudolph et al. | |
| 8,068,169 B2 | 11/2011 | Chang | |
| 8,253,778 B2 | 8/2012 | Atsushi | |
| 8,487,989 B2 | 7/2013 | Sander | |
| 8,758,021 B2 | 6/2014 | Takahashi | |
| 8,998,609 B2 | 4/2015 | Prakash et al. | |
| 9,077,973 B2 | 7/2015 | Aguren | |
| 9,254,103 B2 | 2/2016 | Krishnaswamy et al. | |
| 9,314,148 B2 | 4/2016 | Galstian et al. | |
| 9,335,567 B2 | 5/2016 | Nakamura | |
| 9,372,348 B2 | 6/2016 | Hilkes | |
| 9,532,841 B2 | 1/2017 | Stern et al. | |
| 9,636,188 B2 | 5/2017 | Gattani et al. | |
| 9,642,526 B2 | 5/2017 | Gerten | |
| 9,690,119 B2 | 6/2017 | Garofolo et al. | |
| 9,729,831 B2 | 8/2017 | Birnkrant et al. | |
| 9,766,441 B2 | 9/2017 | Rappel | |
| 9,772,495 B2 | 9/2017 | Tam et al. | |
| 9,820,820 B2 | 11/2017 | Jess et al. | |
| 9,927,611 B2 | 3/2018 | Rudy et al. | |
| 9,931,171 B1 | 4/2018 | Peyman | |
| 9,967,475 B2 | 5/2018 | Schneider et al. | |
| 9,999,350 B2 | 6/2018 | Heeren | |
| 10,057,547 B2 | 8/2018 | Nakamura | |
| 10,073,515 B2 | 9/2018 | Awdeh | |
| 10,169,925 B2 | 1/2019 | Takano et al. | |
| 10,175,507 B2 | 1/2019 | Nakamura | |
| 10,222,597 B2 | 3/2019 | Hauger | |
| 10,222,619 B2 | 3/2019 | Yu | |
| 10,225,526 B2 | 3/2019 | Hilkes et al. | |
| 10,230,943 B2 | 3/2019 | Achilefu et al. | |
| 10,231,607 B2 | 3/2019 | Charles et al. | |
| 10,278,566 B2 | 5/2019 | Okazaki et al. | |
| 10,398,514 B2 | 9/2019 | Ryan et al. | |
| 11,006,093 B1 | 5/2021 | Hegyi | |
| 11,166,006 B2 | 11/2021 | Hegyi | |
| 2001/0056238 A1 | 12/2001 | Tsujita | |
| 2003/0139736 A1 | 7/2003 | Sander | |
| 2004/0113867 A1 | 6/2004 | Tomine et al. | |
| 2004/0233280 A1 | 11/2004 | Aoyama | |
| 2005/0033145 A1 | 2/2005 | Graham et al. | |
| 2005/0088763 A1 | 4/2005 | Weaver et al. | |
| 2006/0077543 A1 | 4/2006 | Miyoshi et al. | |
| 2007/0274577 A1 | 11/2007 | De Font-Reaulx Rojas | |
| 2008/0088937 A1 | 4/2008 | Tang | |
| 2008/0180521 A1 | 7/2008 | Ahearn | |
| 2010/0045783 A1 | 2/2010 | State et al. | |
| 2010/0238551 A1 | 9/2010 | Hubbs | |
| 2010/0321409 A1 | 12/2010 | Komori | |
| 2011/0145978 A1 | 6/2011 | Harbin | |
| 2012/0050493 A1 | 3/2012 | Ernst et al. | |
| 2012/0140322 A1 | 6/2012 | Schnell et al. | |
| 2014/0146153 A1* | 5/2014 | Birnkrant ............... H04N 7/18 348/77 | |
| 2015/0009550 A1* | 1/2015 | Misago ............... H04N 9/3155 359/205.1 | |
| 2015/0164327 A1 | 6/2015 | Yaroslavsky et al. | |
| 2015/0173846 A1 | 6/2015 | Schneider et al. | |
| 2015/0226969 A1 | 8/2015 | Tsukahara et al. | |
| 2015/0331230 A1 | 11/2015 | Wilt et al. | |
| 2016/0033770 A1 | 2/2016 | Fujimaki et al. | |
| 2016/0057343 A1 | 2/2016 | Duan et al. | |
| 2016/0131867 A1 | 5/2016 | Greene et al. | |
| 2016/0187969 A1 | 6/2016 | Larsen et al. | |
| 2016/0209648 A1 | 7/2016 | Haddick et al. | |
| 2016/0225192 A1* | 8/2016 | Jones ................. G06F 3/011 | |
| 2016/0248994 A1 | 8/2016 | Liu | |
| 2016/0262608 A1 | 9/2016 | Krueger | |
| 2016/0358327 A1 | 12/2016 | Lemchen | |
| 2016/0360074 A1 | 12/2016 | Winer et al. | |
| 2017/0007351 A1* | 1/2017 | Yu ................. G02B 27/0172 | |
| 2017/0045721 A1 | 2/2017 | Charles | |
| 2017/0099479 A1* | 4/2017 | Browd ................. H04N 13/156 | |
| 2017/0171538 A1 | 6/2017 | Bell et al. | |

(56) References Cited

U.S. PATENT DOCUMENTS

| | | | |
|---|---|---|---|
| 2017/0181802 A1* | 6/2017 | Sachs | A61B 34/30 |
| 2017/0199366 A1 | 7/2017 | Rappel | |
| 2017/0202633 A1 | 7/2017 | Liu | |
| 2017/0208252 A1 | 7/2017 | Tamura | |
| 2017/0245954 A1 | 8/2017 | Beira | |
| 2017/0273549 A1 | 9/2017 | Nazareth et al. | |
| 2017/0322410 A1* | 11/2017 | Watson | H04N 13/254 |
| 2017/0336609 A1 | 11/2017 | Lerner et al. | |
| 2017/0336635 A1 | 11/2017 | Yoon et al. | |
| 2018/0012413 A1* | 1/2018 | Jones | G06F 3/012 |
| 2018/0032130 A1 | 2/2018 | Meglan | |
| 2018/0149467 A1 | 5/2018 | Ren et al. | |
| 2018/0249891 A1 | 9/2018 | Fukuda et al. | |
| 2018/0270474 A1 | 9/2018 | Liu | |
| 2018/0316834 A1 | 11/2018 | Grabow | |
| 2018/0333049 A1 | 11/2018 | Charles | |
| 2018/0368690 A1 | 12/2018 | Muschaweck et al. | |
| 2019/0036992 A1 | 1/2019 | Stewart et al. | |
| 2019/0099226 A1 | 4/2019 | Hallen | |
| 2019/0121168 A1 | 4/2019 | Greget | |
| 2019/0132526 A1 | 5/2019 | Reimer et al. | |
| 2019/0142256 A1 | 5/2019 | Zhao et al. | |
| 2019/0212533 A9 | 7/2019 | Heeren et al. | |
| 2019/0254754 A1* | 8/2019 | Johnson | G16H 20/40 |
| 2019/0327394 A1 | 10/2019 | Ramirez Luna et al. | |
| 2020/0117025 A1* | 4/2020 | Sauer | G02C 9/00 |
| 2020/0275087 A1 | 8/2020 | Yasuda et al. | |
| 2020/0330179 A1* | 10/2020 | Ton | G02C 7/088 |
| 2021/0067764 A1* | 3/2021 | Shau | A61F 9/022 |
| 2021/0235061 A1 | 7/2021 | Hegyi | |

FOREIGN PATENT DOCUMENTS

| | | |
|---|---|---|
| CN | 102711652 A | 10/2012 |
| CN | 202615066 U | 12/2012 |
| CN | 103211573 A | 7/2013 |
| CN | 203101728 U | 7/2013 |
| CN | 102224732 B | 4/2015 |
| CN | 104939925 A | 9/2015 |
| CN | 205433937 U | 8/2016 |
| CN | 205982831 U | 2/2017 |
| CN | 106725906 A | 5/2017 |
| CN | 103596488 B | 8/2017 |
| CN | 104834091 B | 10/2017 |
| CN | 107277463 A | 10/2017 |
| CN | 107771050 A | 3/2018 |
| CN | 107850778 A | 3/2018 |
| CN | 207253386 U | 4/2018 |
| CN | 107976795 A | 5/2018 |
| CN | 207545230 U | 6/2018 |
| CN | 108618852 A | 10/2018 |
| CN | 108652824 A | 10/2018 |
| CN | 108852525 A | 11/2018 |
| CN | 108852617 A | 11/2018 |
| CN | 108885086 A | 11/2018 |
| CN | 208207348 U | 12/2018 |
| CN | 106707487 B | 3/2019 |
| DE | 10050351 A1 | 5/2001 |
| EP | 815801 B1 | 8/2003 |
| EP | 1400829 B1 | 1/2007 |
| EP | 1067875 B1 | 11/2008 |
| EP | 2786196 A1 | 10/2014 |
| EP | 221321981 | 4/2016 |
| EP | 3069679 A1 | 9/2016 |
| EP | 3322329 A1 | 5/2018 |
| EP | 3373796 A2 | 9/2018 |
| EP | 3426127 A1 | 1/2019 |
| GB | 2552257 A | 1/2018 |
| IN | 200606157 P1 | 11/2009 |
| IN | 201304960 I4 | 5/2015 |
| IN | 201500610 P2 | 12/2015 |
| IN | 201614022016 A | 2/2017 |
| JP | 6261913 A | 9/1994 |
| JP | 7325270 A | 12/1995 |
| JP | H11153412 A | 6/1999 |
| JP | 2938940 B2 | 8/1999 |
| JP | H11271639 A | 10/1999 |
| JP | 2000042023 A | 2/2000 |
| JP | 3197558 B2 | 8/2001 |
| JP | 2003149559 A | 5/2003 |
| JP | 2003204972 A | 7/2003 |
| JP | 2005021453 A | 1/2005 |
| JP | 2005034285 A | 2/2005 |
| JP | 3789960 B2 | 6/2006 |
| JP | 2006319660 A | 11/2006 |
| JP | 2006345119 A | 12/2006 |
| JP | 4025357 B2 | 12/2007 |
| JP | 4067309 B2 | 3/2008 |
| JP | 2009092808 A * | 4/2009 |
| JP | 4440893 B2 | 3/2010 |
| JP | 3162115 U | 8/2010 |
| JP | 4598449 B2 | 12/2010 |
| JP | 5261588 B2 | 8/2013 |
| JP | 5311601 B1 | 10/2013 |
| JP | 2014104365 A | 6/2014 |
| JP | 5652973 B1 | 1/2015 |
| JP | 2015061615 A | 4/2015 |
| JP | 6097590 B2 | 3/2017 |
| JP | 2017523817 A | 8/2017 |
| JP | 2018029980 A | 3/2018 |
| JP | 2018101134 A | 6/2018 |
| JP | 2019033838 A | 3/2019 |
| KR | 20090091624 A | 8/2009 |
| KR | 10109845381 | 12/2011 |
| KR | 10-1638628 B1 | 7/2016 |
| KR | 10-1654589 B1 | 9/2016 |
| KR | 10-1660011 B1 | 9/2016 |
| KR | 10-1664468 B1 | 10/2016 |
| KR | 10-20170035831 A | 3/2017 |
| KR | 10-1870837 B1 | 6/2018 |
| KR | 10-1874778 B1 | 8/2018 |
| WO | WO96/009566 A1 | 3/1996 |
| WO | WO01/005161 A1 | 1/2001 |
| WO | WO2005/088539 A2 | 9/2005 |
| WO | WO2007/033326 A2 | 3/2007 |
| WO | WO2007/107266 A1 | 9/2007 |
| WO | WO2010/067267 A1 | 6/2010 |
| WO | WO2011/002209 A2 | 1/2011 |
| WO | WO2012/038582 A2 | 3/2012 |
| WO | WO2014/005388 A1 | 1/2014 |
| WO | WO2014/076045 A2 | 5/2014 |
| WO | WO2014/144940 A2 | 9/2014 |
| WO | WO2015/061793 A1 | 4/2015 |
| WO | WO2015/100129 A1 | 7/2015 |
| WO | WO2015/125447 A1 | 8/2015 |
| WO | WO2015/126466 A1 | 8/2015 |
| WO | WO2015/164402 A1 | 10/2015 |
| WO | WO2015/164881 A1 | 10/2015 |
| WO | WO2016/030873 A1 | 3/2016 |
| WO | WO2016/162789 A2 | 10/2016 |
| WO | WO2016/170816 A1 | 10/2016 |
| WO | WO2017/072860 A1 | 5/2017 |
| WO | WO2017/147235 A1 | 8/2017 |
| WO | WO2018/002674 A1 | 1/2018 |
| WO | WO2018/059934 A1 | 4/2018 |
| WO | WO2018/097831 A1 | 5/2018 |
| WO | WO2018/123198 A1 | 7/2018 |
| WO | WO2018/183905 A1 | 10/2018 |
| WO | WO2018/200309 A2 | 11/2018 |
| WO | WO2018/203473 A1 | 11/2018 |
| WO | WO2018/211332 A1 | 11/2018 |
| WO | WO2018/211782 A1 | 11/2018 |
| WO | WO2018235088 A1 | 12/2018 |
| WO | WO2019/040244 A1 | 2/2019 |

OTHER PUBLICATIONS

Cha et al.; Real time, label-free, introoperative visualization of peripheral nerves and micro-vasculatures using multimodal optical imaging techniques: Biomedical Optics Express; 9(3); pp. 1097-1110; Mar. 2018.

(56) References Cited

OTHER PUBLICATIONS

Dang et al.; Continuous stereo self-calibration by camera parameter tracking; IEEE Transactions on image processing; 18(7); pp. 1536-1550; Jun. 2009.

Edwards et al.; Video see-through design for merging of real and virtual enviroments; InProceedings of IEEE Virtual Reality Annual International Symposium; pp. 223-233; Sep. 1993.

I-Med Technology; Digital Surgical Loupe; retrieved from the internet (https://www.i-medtech.nl/); 5 pages (Product Discription); on Mar. 10, 2021.

Medstartr; Augmented reality guided surge: next generation fluorescent and image guided surgery; retrieved from the internet (https://www.medstartr.com/project/detail/200429); 15 pages (Product Discription); on Mar. 10, 2021.

Mela et al.; Steroscopic integrated imaging goggles for multimodal intraoperative image guidance; Plos One; 10(11); e0141956; 17 pages; Nov. 2015.

Nueyes; Creating inclusive experiences through technology; retrieved from the internet (https://www.nueyes.com/); 4 pages (Product Discription); on Mar. 10, 2021.

Park et al.; Multispectral imaging using multiplexed illumination; In2007 IEEE 11th International conference on Computer Vision; pp. 1-8; Oct. 2007.

Quang et al.; Fluorescence imaging topography scanning system for intraoperative multimodal imaging; Plos one; 12(4); e0174928; 14 pages; Apr. 2017.

Surglasses; Evolution in surgery; retrieved from the internet (https://www.surglasses.com/surglasses/index.html); 4 pages (Product Discription): on Mar. 10, 2021.

Zhang; A flexible new technique for camera calibration; Microsoft Corporation Technical Report MSR-TR-98-71; retrieved from the internet (https://www.microsoft.com/en-us/research/wp-content/uploads/2016/02/tr98-71.pdf); 22 pages; on Mar. 9, 2021.

\* cited by examiner

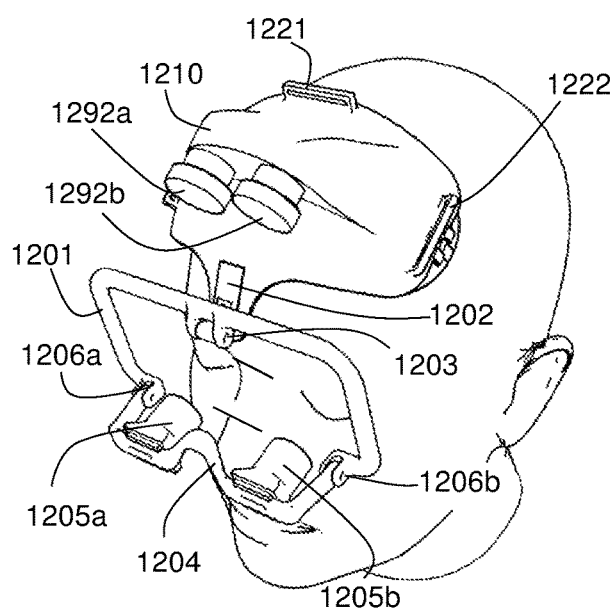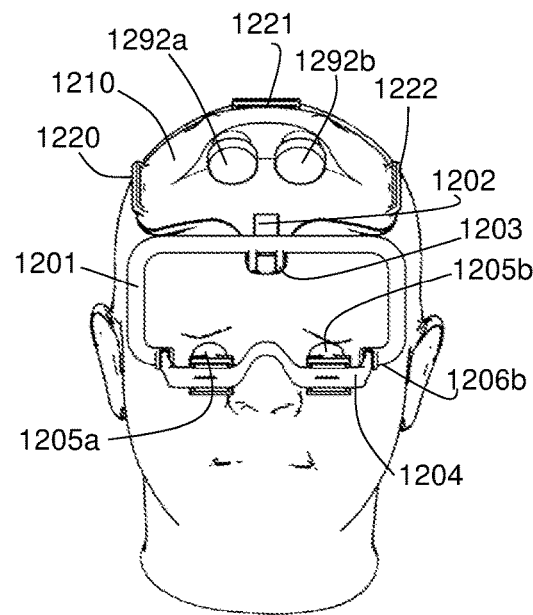
FIG. 12A  FIG. 12B
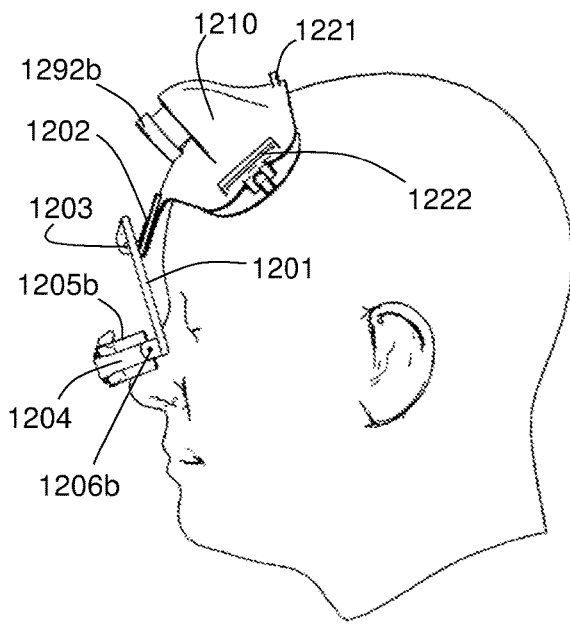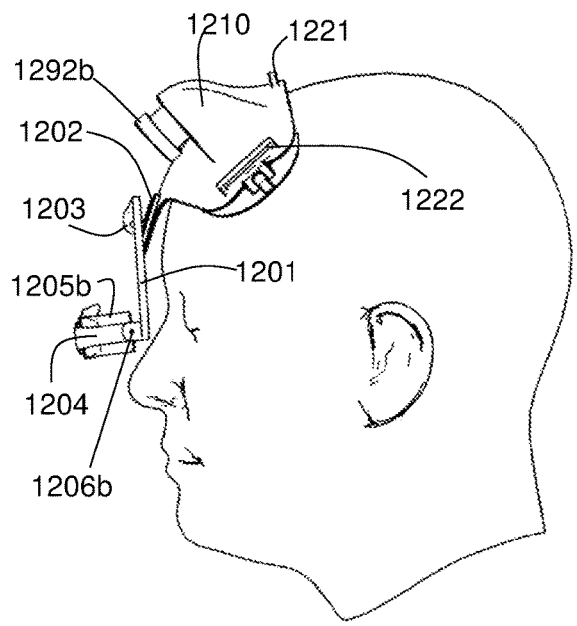
FIG. 12C  FIG. 12D

FIG. 13A
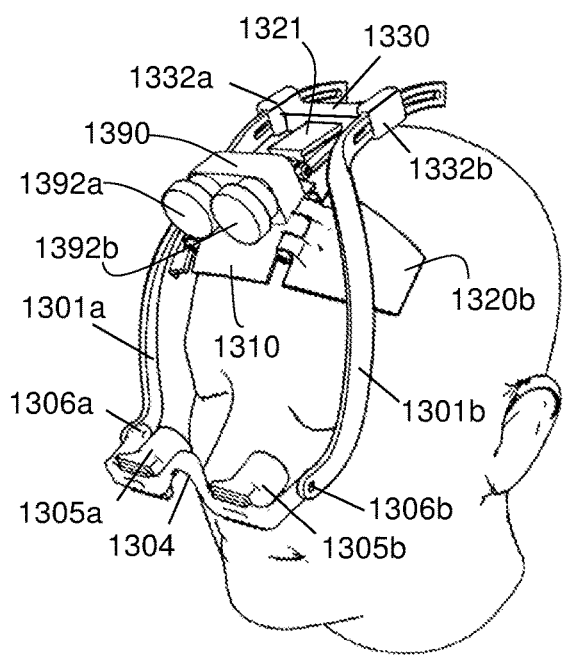
FIG. 13B
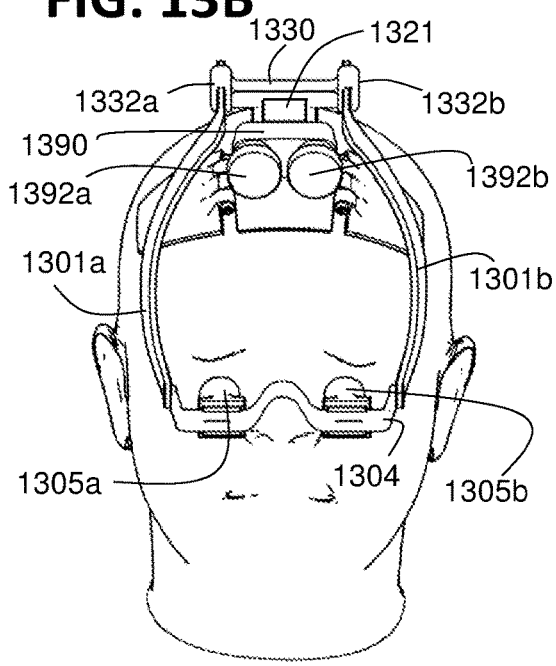
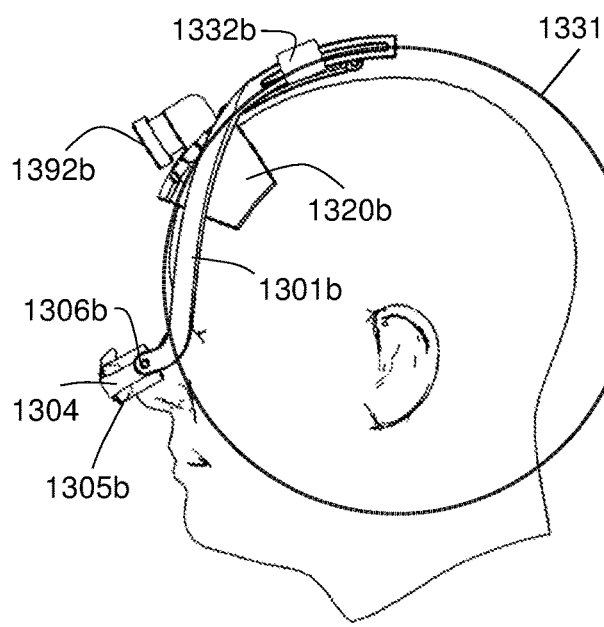
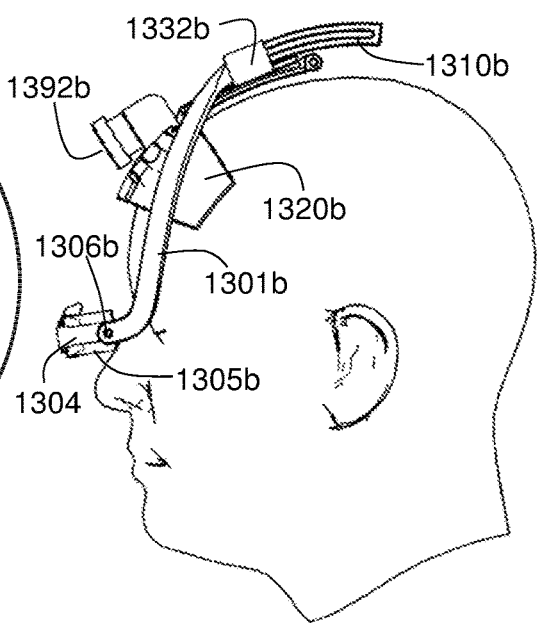
FIG. 13C
FIG. 13D

OPEN VIEW, MULTI-MODAL, CALIBRATED DIGITAL LOUPE WITH DEPTH SENSING

CROSS-REFERENCE TO RELATED APPLICATIONS

This application is a continuation of U.S. application Ser. No. 17/156,217, filed Jan. 22, 2021, entitled "OPEN VIEW, MULTI-MODAL, CALIBRATED DIGITAL LOUPE WITH DEPTH SENSING," which application claims the benefit of priority of U.S. Provisional Application No. 62/964,287, filed Jan. 22, 2020, entitled "DIGITAL LOUPE WITH CALIBRATED DEPTH SENSING", all of which are incorporated by reference as if fully set forth herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure describes devices and methods for improving digital magnifying loupes. More specifically, these devices and methods allow for an increased range of working distances, superior visual ergonomics, and the incorporation of advanced multi-channel optical imaging modalities.

BACKGROUND

Surgeons, dentists, jewelers, and others whose work relies on precise hand-eye coordination at a miniature scale have long used binocular loupes as a visual aid. Such loupes comprise a pair of non-inverting telescopes with a working distance of approximately 0.5 m, that is, the distance from the eyes of the user to the nominal point of convergence of the optical axes of the two telescopes, which in normal usage is the location of the subject or work area under observation, is approximately 0.5 m. The telescopes are usually embedded in a user's spectacles in a "near-vision" position, similar to the near-vision position at the bottom of the lenses of bifocals, except they offer an angular magnification of around 2× to 3× over a relatively limited field of view, while permitting both peripheral and "far" vision when the user looks around the telescopes.

The term "digital loupe" has been used to refer to loupe-like systems, often for use in surgery, where a focal plane array (image sensor) is placed at the focal plane of each of the telescopes to digitize the image. The digitized images can be transformed through various forms of signal processing before being displayed at the focal planes of two eyepieces or oculars, one for each eye. This arrangement forms a binocular head-mounted display (HMD) with a digitally created magnified view of the work area.

With a digital loupe comes both many challenges and many opportunities. For example, there is the added weight of the image sensors, displays, and other electronic components, as well as the loss of depth of field that would otherwise come from the eye's natural focusing accommodation. However, as will be explained in the context of the present disclosure, digital technology brings capabilities like image stabilization, automatic focus, and automatic convergence that enable magnifications approaching those of a surgical microscope. Such capabilities enable flexibility of working distance and freedom of movement, neither of which are afforded by such microscopes, nor by traditional analog loupes. Furthermore, the bifurcation of the sensing/imaging side and the display side of the loupes, enabled by the digital, rather than optical, information transfer between the two, allows for separate optimization of their mounting configurations. As will be shown, this creates more ergonomic working conditions for the surgeon, such as a more vertical head position, as well as the ability to simultaneously and concurrently view an object or work area directly (i.e., without looking through the loupes) and through the loupes. Finally, with digital technology, it is possible to include more advanced optical imaging modalities such as fluorescence imaging or hyperspectral imaging, e.g., for a visualization of tumor margins overlaid on the loupe image.

There are several outstanding challenges of digital loupes in the prior art that embodiments of the present disclosure aim to solve. First, with high-magnification binocular systems, a condition known as diplopia or double vision is known to arise, especially if left and right optical axes of the system are not properly aligned. Also, at higher magnifications, slight changes in working distance may translate to large relative shifts in the positions of left and right images, such that the human visual system cannot comfortably maintain single vision. The prior art has attempted to overcome this, but in an incomplete manner, whereas the present disclosure overcomes this challenge completely by incorporating a distance sensor with a defined angular field of view as well as a processor with camera calibration information that is used to electronically transform the image along with measurements from the distance sensor. We now review the prior art relevant to this first outstanding challenge before delineating the others.

It was recognized some time ago that, just as it is important for a camera to have autofocus to maintain a sharp image as the distance to a subject is changed, so a set of loupes should automatically adjust its horizontal convergence angle, or the acute angle formed between the optical axes of the left and right telescopes as viewed in a top projection, such that the optical axes of the left and right telescopes converge to the subject or work area being observed. U.S. Pat. No. 5,374,820 teaches using a distance sensor on a traditional (analog) loupe to measure the distance to a subject. This distance measurement is then used to mechanically change, in a corresponding fashion, the focal distance and the convergence angle of the telescopes, or oculars. However, such mechanical movement is not sufficiently precise at high magnification, there is no provision for incorporation of calibration information that might be used to correct for angular misalignments (both horizontal and vertical) of the telescopes as a function of distance, and the distance sensor does not have a defined field of view. There is only a provision for adjusting the convergence angle as viewed in a top projection, that is, the horizontal convergence angle. The eyes are generally more sensitive to image misalignments in the vertical direction, but this patent does not teach a method to overcome any such misalignments, which may be caused by slightly different tilts of the oculars relative to their as-designed or as-intended configuration.

WO2001005161 teaches a digital surgical loupe that dynamically optimizes the image based on surgical conditions. It teaches that the optimal stereoscopic vision is given when a baseline (corresponding to the interpupillary distance (IPD) of the stereo camera pair) is about ¹⁄₂₀th of the working distance. Based on the focus distance inferred from the best focus setting of the stereo camera pair, this system has motors that first adjust the IPD to be in the optimal range, and then subsequently adjust the horizontal convergence angle (in the plane of the two cameras and the subject) so the cameras of the stereo pair converge on the subject. However, the use of focus setting as a proxy for a true distance measurement to the subject is too inaccurate for the needs of a high-magnification loupe—for example, conversion of a focus setting to a distance may be accurate to within a few cm, whereas a distance accuracy of better than a few mm is needed for an optimal system. Also, the use of motors to adjust IPD and convergence angle leads to a bulky system and may lack sufficient accuracy, repeatability, stability, and rapid settling to a given convergence angle setting. There is no provision to include camera calibration information that could be used to actively correct for horizontal and vertical misalignments between a horizontal convergence angle setting and the actual camera orientations. The present disclosure overcomes these limitations.

Some embodiments of digital loupes and/or augmented reality headsets within the prior art rely on methods that do not use distance sensors or direct distance measurements to determine a convergence angle, while others also do not rely on motor-driven systems. For example, US 2010/0045783 teaches, for a video see-through head-mounted display used in a surgical context, a method of dynamic virtual convergence. Each camera of a stereo pair has a field of view larger than the displays used to display the camera images, and a heuristic (for example, the distance to the points closest to the viewer within an estimated scene geometry, or the distance to a tracked tool) is used to estimate the gaze distance of the viewer. Display frustums are transformed, electronically, to match the estimated gaze distance. Effectively, the convergence is virtually adjusted because only a portion of each camera image is shown on each corresponding display, that portion which corresponds to the object that the viewer is gazing at, and which depends on the distance to that object. One notable feature of the system described in US 2010/0045783 is the use of filtering high temporal frequency components of the gaze distance. However, the user's gaze distance is not accurately measured by an independent sensor. Also, the display frustums are transformed to a convergence angle of 0 degrees, i.e., parallel vision, as if the object is at infinity, so that the technique can be used with conventional binocular head-mounted displays that have a relative ocular convergence angle of 0 degrees. This approach creates a vergence-disparity conflict, whereby the horizontal disparities (pixel shifts) between the left and right images are the same as if the object were at its original (near) location, but the lack of convergence of the eyes sends a conflicting signal to the brain that the object is far away. Thus, this approach is not useful for comfortably maintaining concurrence between peripheral near vision and augmented vision, where one may want to switch between a magnified or augmented view of an object or work area and a direct view of the object or work area while looking through the oculars or displays, and while maintaining the same vergence state of the eyes when looking over or under the oculars or displays. The present disclosure overcomes this limitation with an ocular convergence angle of the head-mounted display that nominally matches the actual working distance of the user and with a processor that can transform the images from the stereo camera pair such that the eyes do not substantially need to change their vergence state when switching between viewing the images of an object or work area through the head-mounted display and concurrently viewing the object or work area directly over a range of working distances.

Some embodiments of digital loupes use position tracking or image feature tracking to maintain an object within the field of view of both eyes, effectively maintaining a convergence of a stereo camera pair to that object. U.S. Pat. No. 9,967,475 B2 teaches a digital loupe that requires an operator to manually select an object of interest in an image, and a processor that determines the line of sight of the object of interest relative to the camera optical axis and re-positions and crops a portion of the image based on tracked head deviations from the line of sight, such that the object of interest stays within the center of the cropped image. US 20160358327 A1 teaches a sort of digital loupe, wherein a live, magnified view of a (dental) work area is provided, and automatically tracked to keep it centered within the field of view of a head-mounted display, using image feature recognition and micro pan and tilt adjustments of the attached cameras. U.S. Pat. No. 9,690,119 B2 teaches a first optical path and a second optical path on a head-worn apparatus where the direction of the first optical path is separately adjustable relative to the direction of the second optical path, and a magnified image passes between the two. U.S. Pat. No. 9,690,119 B2 also teaches the setting of a convergence angle (e.g., using adjustable mirrors) such that single vision occurs at the working distance, and it teaches automatic tracking of a point within the field of view by recognition of implicit or explicit features, but it does not teach the use of a direct measurement of distance to the subject.

U.S. Pat. No. 9,772,495 teaches a digital loupe that is intended to replace both the conventional surgical loupe and the surgical microscope. It teaches two cameras, each on an axial rotation system, and an illumination module. The axial rotation systems and illumination module respond to a feedback signal derived from the two cameras to maintain consistent illumination and a stable image. Moreover, while U.S. Pat. No. 9,772,495 teaches that the axial rotation modules rotate to allow for capturing a desired surgical view, no provision is given for how to determine, either manually or automatically, what this desired view comprises, nor how to track it as the surgeon moves around. It also explains that the images from the two cameras have to be aligned to avoid double vision, presumably by rotating the cameras, but no explanation or details are given about how this is done. In any case, embodiments that use position or image feature tracking count on the ability to derive robust, precise, and reliable estimates of distance to the subject, which these methods cannot give. For example, image feature tracking relies on the presence of distinct features in an image, which cannot always be assumed due to the existence of relatively featureless or textureless subjects.

A second challenge of digital loupes in the prior art that the present disclosure overcomes relates to the incorporation of multiple optical imaging modalities. Some modalities, such as hyperspectral imaging, depend on the measurement of multiple channels for a given image point. There are various examples in the prior art of digital loupes incorporating advanced imaging modalities; however, it is known that multi-channel modalities like hyperspectral imaging may be hard to integrate in digital loupes due to the bulk of the instruments and/or to tradeoffs involving spatial or temporal resolution, etc. An aspect of the present disclosure is to form a hyperspectral imager or other multi-channel imager (e.g., Stokes imaging polarimeter) that is small enough to include in a digital loupe, yet without sacrificing light throughput or temporal or spatial resolution, by inclusion of an imaging depth sensor and a calibrated array of single-channel imagers. A processor uses a depth image from the imaging depth sensor to remove parallax from images from the single-channel imagers such that they appear to have been captured from the same viewpoint, just like in more conventional multi-channel yet single-viewpoint imagers. Within the present disclosure, "channel" may refer to an individual wavelength band, an individual polarization component, or a corresponding notion; or, it may refer to an image acquired from light corresponding to one of these notions of channel. Thus, multispectral and hyperspectral imagers are multi-channel imagers because they image multiple wavelength bands, and a Stokes imaging polarimeter is a multi-channel imager because it images multiple polarization components.

Previous embodiments of digital loupes have incorporated multiple optical imaging modalities. For example, U.S. Pat. No. 6,032,070 teaches reflecting light off tissue and imaging, using various optical methods (different wavelength bands, polarizations, etc.) and digital processing to enhance contrast of tissue structures beyond what is visible with the naked eye. This is done in conjunction with a helmet or head mounted device, such that the enhanced contrast image is displayed stereoscopically along the line of sight of the user. WO 2011002209 A2 teaches a digital loupe that combines magnification and illumination in various spectral bands, and has a manually-adjustable convergence of the cameras. WO 2018235088 A1 teaches a digital loupe with an array of cameras for each eye with the same working distance, e.g., on a headband. The different cameras within an array for a given eye may have different magnifications, or may comprise a color camera and an infrared camera, in such a way that at least two corresponding cameras from left and right eyes are used to provide a stereoscopic view. A manual controller is used to select a low magnification stereoscopic image, or a high magnification stereoscopic image, or an infrared stereoscopic image, etc. Note that while this publication discloses an array of cameras, it does not teach fusing the images from the array into a single viewpoint multi-channel image using spatially resolved distance information as does the present disclosure. For the purposes of the present disclosure, a multi-channel imager may comprise single channels at different magnifications.

U.S. Ser. No. 10/230,943 B2 teaches a type of digital loupe with integrated fluorescence imaging such that within one sensor, both NIR (fluorescence) and visible light are recorded, with a modified Bayer pattern where pixels in both visible and infrared bands can be tiled on the same sensor. This simplifies co-registration of color RGB and NIR fluorescence images because they are obtained from the same viewpoint. However, with current image sensor technology this technique is somewhat impractical due to the significantly different optimal imaging conditions desired for each modality. Each modality may have different optimal exposure times, gains, resolutions, pixel sizes, etc., but because the modalities are being recorded on the same sensor, they must be recorded with the same conditions if they are to be recorded simultaneously. There is also a loss of spatial resolution for each modality due to the sharing of the image sensor's pixels across modalities.

US 2018/0270474 A1 teaches registration of optical imaging with other preoperative imaging modalities and topographical/depth information from a 3D scanning module. It also teaches that the depth information can be used to register images between multiple intraoperative optical imaging modalities, such as NIR fluorescence, color RGB, or hyperspectral (using a tunable liquid-crystal filter or a filter wheel), but not between individual channels of a multi-channel imaging system. While hyperspectral imaging (or other modalities such as imaging polarimetry) can be a potentially valuable source of information in a digital loupe system, the methods suggested in the prior art do not allow for the effective combination of miniaturization, temporal resolution, spatial resolution, and light throughput that would be desired for an optimal system.

A third challenge that the present disclosure overcomes is related to ergonomics. A traditional or analog surgical loupe comprises a pair of non-inverting telescopes that are suspended in front of a user's eyes, the optical axes of the left and right telescopes aligned correspondingly with the optical axes of the user's left and right eyes. There are three prototypical solutions for suspension of these telescopes, or oculars, in front of the user's eyes, within the prior art. Each has advantages and disadvantages with respect to functional attributes of the loupe system, including weight, comfort, field of view, view occlusion and peripheral vision, customization of fit, stability, and adjustability.

For the purposes of this disclosure, "weight" includes notions such as the overall mass of the analog or digital surgical loupe or other visual aid, as well as the distribution of that mass on the head of the surgeon. These both have implications for the comfort of the surgeon. For example, if the mass of such a system is distributed such that in operation, it shifts the combined center of gravity of the system and the surgeon's head significantly forward of the center of gravity of the surgeon's head alone, this will increase strain on the surgeon's neck relative to the unaided surgeon. Such strain contributes to the discomfort of the surgeon especially in cases of prolonged use. Furthermore, distributing the weight of the system across a larger area of the surgeon's head generally provides greater comfort than distributing the weight across a smaller area of the surgeon's head, although certain areas of the head are more sensitive to pressure than other areas, e.g., the temples and supraorbital regions being affected by tight headbands, as well as the nose when used to support loupes via nose pads.

Field of view and view occlusion or peripheral vision are also important functional attributes that are useful for comparing loupe systems. Here, by field of view we are referring to the apparent field of view, which is the angular extent of the magnified field as presented to the user. This is to be distinguished from the true field of view, which is the angular extent of the unmagnified field. An eyepiece with a given clear aperture of the front lens surface supports a greater apparent field of view when it is closer to the user's eye, or when the eye relief is smaller, than when it is further away. However, the closer the eyepiece is to the eye, the more the peripheral vision of the user is occluded. An ideal system would not occlude any parts of the user's field of vision outside of the apparent field of the loupe system. In practice this is not possible as the eyepiece must be stably mechanically supported and aligned with and in front of the optical axis of the user's eye. Careful consideration of the support mechanisms, as in the present disclosure, can be used to minimize the perturbation of the user's field of vision from these support mechanisms and thus preserve the sensation of an open view of the user's surroundings.

Finally, the interrelated attributes of customization of fit, stability, and adjustability are significant for determining the overall performance of the loupe system. As a general rule, the more adjustable the fit of a system is, the less it has to be customized to the user. However, to create a mechanism that is both adjustable and stable generally requires more material, and thus more mass, than a system that is stable but not adjustable. This excess material has the potential to increase the weight and view occlusion of the system, negatively impacting comfort and visual performance.

We now turn to a description of the design solutions presently in use for analog surgical loupes. The first solution, which we shall call the "through-the-lens" mount, is the lowest profile, but also the least flexible of the three. A pair of spectacles is custom-fit for the surgeon through an involved fitting process. The working distance, interpupillary distance, declension angle, prescription, frame size, and precise drilling positions must all be carefully measured and incorporated at the time of manufacture, and subsequently cannot be changed. A hole is drilled into each of the left and right lenses of the spectacles, and these holes are used to support the oculars in a position precisely aligned with the optical axes of the user's eyes in a near-vision position. This level of customization and lack of adjustability is feasible because like eyeglasses, surgical loupes are not traditionally shared. Also, custom loupes incorporate the surgeon's optical prescription both within the spectacles and the telescopes, so the peripheral field viewed through the spectacles remains in focus. This solution has the lowest weight as no framing is required beyond the eyeglasses. However, the bulk of the weight is supported by the nose pads resting on the surgeon's nose, thus this style becomes uncomfortable at higher magnifications due to the weight of the large objectives needing to be supported by these nose pads. Furthermore, placement of the loupes (and thus the maximum declension angle of the oculars) is somewhat constrained by the surgeon's anatomy, e.g., the height of the surgeon's nose relative to the eyes. The through-the-lens placement enables smaller oculars for the same apparent field of view because the oculars can be placed very close to the surgeon's eyes. But if changes in prescription are needed, the loupe system needs to be remanufactured. Furthermore, laser safety eyewear is not easily integrated with such a loupe.

A next style of loupe is the flip-up mount or front lens mount, which is clipped onto the front of the spectacles. The oculars are supported completely in front of the spectacles via an adjustable support arm. This allows for more adjustment of lens position, declension, etc., and less need for customization. However, the weight of the system, supported primarily by the nose pads, increases significantly: bigger lenses are needed to maintain the same apparent field of view because the lenses now sit further away from the surgeon's eyes; more framing is needed to support the lenses in an adjustable way; and finally, due to the forward center of gravity relative to through-the-lens loupes, more force is placed on the surgeon's nose, and there is more strain on the surgeon's neck. The presence of the support system in front of and above the surgeon's nose partially occludes the surgeon's field of vision near the center, and gives a somewhat uncomfortable experience relative to not having anything there. Flexibility is enhanced as the spectacle lenses can be changed to enable changes in prescription or addition of laser or other optical filters. While adjustment of ocular positioning is enabled by this mount, it is only possible over a relatively small range due to the need to keep the ocular support system small to minimize view occlusion, as well as due to the relatively short length of the ocular support arm. The adjustable declension is useful in that it allows the surgeon to assume various cervical spine extension angles while viewing the same magnified work area, but as the lenses stick out more than in the through-the-lens style of loupe, there is a greater chance of interference with conventional face shields.

A third style of loupe is the flip up mount but with the support on a headband rather than on the front of the spectacles. This relieves the nose from supporting the weight of the oculars and thus is suited to higher magnifications and/or prismatic loupes that utilize a Keplerian rather than Galilean structure, with a prism to undo the image inversion caused by the Keplerian telescope. A larger support structure/longer support arm is needed to hold the oculars in front of the eyes of the surgeon, necessitating even more weight, but this weight can be distributed across the head using the headband structure. The longer support arm may therefore appear even more prominently in the surgeon's peripheral vision, especially at greater ocular declension angles, an undesirable feature of this configuration. While a longer or larger support structure generally enables longer translational ranges and greater distances between pivot points and supported objects, thus enabling greater adjustment freedom, this comes at the expense of stability, as rotational head motions are amplified by the longer lever arm. But personal eyewear, including laser safety eyewear, is independent of the loupe system and therefore easily used in combination with it. Such a loupe system can be easily shared among surgeons.

Many of the considerations and tradeoffs that arise in the field of surgical loupes also arise in the field of near-eye displays or head-mounted displays, especially those that provide for visual augmentation. These include weight and comfort, stability and adjustability of fit, and preservation (or not) of peripheral vision. US Patent Publication US20040113867A1 teaches a head-mountable display system that is designed to minimize the view occlusion of the user while maintaining the ability to see above and/or below the displays. The view angle of the displays relative to the horizontal, commensurate with the declension angle of the loupes, is adjustable, as are various fitting parameters of the system, to enable a more comfortable fit and better viewing experience in terms of reducing strain and preserving contextual awareness. U.S. Pat. No. 7,319,437 teaches a lightweight binocular near-eye display that preserves the forward-looking peripheral vision of the user, though it does not specifically describe the mechanisms for how to accomplish this in a way that could be flexible enough for a large range of head sizes and shapes.

The telescopes of an analog surgical loupe are sometimes called oculars, though the words "ocular" and "eyepiece" can also be used interchangeably to describe the lens system or lens element closest to the user's eye in an optical system designed for a human user. The word "objective" is often used to describe the front-most lens of a telescope facing the object or work area. For an analog loupe, absent any folding of the optical path using reflective or refractive means (which again adds bulk and weight), the optical axes of the objective and the eyepiece are collinear. As stated previously, an advantage of a digital loupe is the bifurcation of the imaging side, comprising a stereo camera pair, and the display side, comprising a binocular near-eye display, into two distinct entities. Information transfers electronically between them, and there is no requirement for their optical axes to be collinear or even aligned. This is advantageous because the means of support for both entities can be optimized independently with respect to factors of adjustability, stability, peripheral vision, and ergonomics. For example, by introducing parallax between or displacing the relative viewpoints of the stereo camera pair and the user's eyes, it is possible to have concurrent direct and augmented views of an object. Also, telescopes are generally understood as afocal optical systems (incoming and outgoing light beams are approximately collimated) that provide angular magnification. An angular shift of the telescope therefore causes a magnified shift in the image viewed through the telescope. However, with bifurcated objective and eyepiece, we must consider how angular shifts of each of these subsystems affect the viewed image: an angular shift of the objective is magnified when viewed at the eyepiece, whereas an angular shift of the eyepiece is not magnified. Therefore, the stability requirements of the objective are greater than those of the eyepiece by the magnification factor.

Furthermore, the magnification factor of a telescope generally comes from the longer focal length of the objective relative to the eyepiece; therefore, the objective is correspondingly larger and heavier than the eyepiece. To minimize the forward pull of the center of gravity beyond that of the surgeon's head alone, it is advantageous to mount the stereo camera pair (objective) of a digital loupe behind the displays (oculars/eyepieces), moving the center of gravity backward in a way that is not possible with conventional analog loupes. Also, the only adjustment on the objective end that is needed is the declension angle, as opposed to the oculars/eyepieces, which need to be precisely aligned with the optical axes of the user's eyes.

Accordingly, there is a need for a new kind of ocular support system, that could be used with analog loupes, digital loupes, head-mounted displays, or any head-worn optical system that includes an ocular, that preserves peripheral vision and thus preserves the user's contextual awareness and a sense of an open view, and that is lightweight, easily adjustable, and stable. The present disclosure aims to provide such an ocular support system that is especially suited to a digital loupe system, where the supports for the oculars and the stereo camera pair can be separately optimized and adjusted, enabling concurrence of direct and augmented vision.

While the devices and methods of the prior art lay a strong foundation for a powerful visual aid for surgery, key gaps remain with regard to the physical and visual ergonomics of such a system, specifically with regard to: minimizing double-vision with stable automatic convergence; preserving peripheral field and a comfortable concurrence of vision between the magnified or augmented view of an object and a direct view to that object, in a form that is comfortable, stable, and easily adjustable; and the incorporation of advanced optical imaging modalities such as hyperspectral and multi-channel fluorescence imaging without compromising image quality or spatial or temporal resolution. It is the aim of the present disclosure to fill these gaps as well as to provide several key enhancements that make the digital loupe an attractive and viable tool for augmenting a surgeon's vision.

SUMMARY OF THE DISCLOSURE

Aspects of the present disclosure provide a digital loupe that combines freedom of movement and flexible working distance, ergonomic comfort, open peripheral vision, concurrence between magnified (or augmented) vision and normal unobstructed vision, magnification with high image quality, and optionally, advanced optical imaging modalities to augment a surgeon's vision in real time. These aspects achieve such advantages via a specific means of supporting oculars in front of the eyes of the surgeon in addition to a specific arrangement of distance sensing, camera calibration, and image transformations that present a stereoscopic augmented view of a surgical wound to a surgeon in an optimal way. Unlike with a surgical microscope, the freedom of movement and flexible working distance enabled by aspects of the present disclosure allow the surgeon to quickly and naturally integrate views of the surgical wound from multiple viewpoints. And unlike with traditional analog loupes, the open peripheral view and concurrence of direct and augmented views allow the surgeon to maintain maximal contextual awareness of the surgical operation, ensuring a smoother outcome.

In one embodiment, the digital loupe comprises a stereo camera pair mounted to the head of a user, including a depth sensing element that has a sensing direction which nominally bisects the lines of sight or optical axes of the cameras of the stereo pair. The depth sensing element may give a single non-spatially-resolved measurement or a spatially-resolved measurement. It may have a defined field of view that may depend on a magnification of the digital loupe. The digital loupe may include illumination also nominally directed along a line that bisects the lines of sight of the cameras, parameters of which may adjust in response to the distance to the subject or object under observation. It may also include a binocular head-mounted display, and a processor that is in operative communication with the stereo camera pair, the depth sensing element, and the binocular head-mounted display. The processor may be in operative communication with an illumination controller that controls an illumination source to adjust parameters of the illumination, such as the illumination intensity and spatial distribution or extent of intensity, as a function of distance measured by the distance sensor. The illumination may be pulsed, potentially in a manner synchronized with the exposure intervals of the stereo camera pair.

The lines of sight of the stereo camera pair may intersect at a nominal working distance of a user, which could be, for example, the average distance between the eyes and hands of a surgeon in an operating posture, or the average of such distances across a set of surgeons. The difference between the system's predefined nominal working distance and the actual working distance between a user's eyes and hands should be small. Furthermore, the eyepieces of the binocular head-mounted display may have a similar convergence angle such that the optical axes of the left and right displays intersect at a similar nominal working distance. The head-mounted display may have a virtual image distance, or distance between the user's eyes and the virtual image plane formed by the head-mounted display optics, similar to a nominal working distance, and it may be designed so as to preserve the peripheral or "far" vision of the user. For example, the oculars of the head-mounted display can be placed in a near-vision position familiar to users of traditional through-the-lens loupes, with ocular supports that only minimally obscure peripheral vision. This allows the user to switch back and forth between normal vision, or direct vision of the surgical wound above or below the oculars, and magnified or augmented vision through the oculars of the head-mounted display, with only an eye rotation (i.e., with no head movement) and with minimal change in visual accommodation and vergence, thus maximizing visual and ergonomic comfort and reducing eye-strain. The direct view and augmented view are therefore "concurrent." In order to further accommodate seamless transitions between direct and augmented vision, the digital loupe system can vary one or more of a virtual convergence angle of images within the oculars, a real convergence angle of the oculars themselves, and a virtual image distance, in response to information derived from the distance sensor, preferably to minimize changes in visual accommodation and vergence when switching between direct and augmented views of an object.

The processor can be used to store and update calibration information that models the precise alignment of the cameras of the stereo pair (e.g., intrinsic and extrinsic camera matrices as used in the pinhole camera model) or other subsystems, including relative position and orientation of all cameras, distance or other sensors, sources of illumination, and displays or oculars. Depending on ergonomic or mechanical degrees of freedom and relative placement of these different subsystems in the digital loupe, it may be necessary to track the state of these degrees of freedom in order to have a complete picture of the relative position and orientation of each of these subsystems. However, such a complete picture is only needed for some embodiments of the present disclosure.

Minimally it is important to calibrate the cameras of the stereo camera pair, as there will always be slight differences between camera parameters (position, orientation, sensor position relative to lens optical axis, focal length, and pixel size) as designed, and as realized in practice. These slight differences, in addition to the convergence angle of the stereo camera pair as designed, manifest in image shifts that vary with distance to the subject under observation, which may, especially at high magnifications, sufficiently displace left and right images of the stereo camera pair such that they cannot be viewed directly through a binocular head-mounted display without further transformation. With knowledge of the camera calibration information, combined with knowledge of the distance to the subject from a distance sensor, it is possible for a processor to precisely correct for the effects of slight camera misalignments as a function of distance. The processor can translate or transform the images before displaying them such that they appear to have come from a stereo camera pair with optical axes that converge to a point along the optical axis of the distance sensor and at the distance measured by the distance sensor. That is, it appears to the user as if the cameras were both directed precisely toward the subject, directly in front of the stereo camera pair at a distance given by the distance sensor. Because the images are subsequently viewed by the user in the head-mounted display, with optical axes of the left and right eyepieces converging to a nominal working distance, the magnified view of the subject will appear at the center of each display, and thus also at the nominal working distance. Thus, because the nominal working distance is the same as, or close to, the actual working distance between the user's eyes and the subject, a user can switch between looking at the subject directly and looking at the subject through the eyepieces with minimal change in the vergence state of their eyes. The processor can optionally perform a second transformation of the images before display, based on the measured distance, such that the displayed subject appears at the actual, rather than nominal, working distance. This second transformation would be equivalent to virtually adjusting the relative convergence angle of the two oculars, such that the left and right eyes converge at the actual working distance (e.g., as measured by the distance sensor) when viewing the left and right images of the subject with single vision. Furthermore, if variable focus oculars are used, the processor can modify the virtual image distance to match the actual working distance. Thus, in this optional approach, no change in visual accommodation or vergence would be necessary to switch between a magnified or augmented view of the subject and a direct view of the subject above or below the oculars.

If an imaging distance or depth sensor is used, or the geometry of the scene is estimated (for example by disparity calculations from the stereo pair, perhaps made more accurate with the point depth sensor, or via structure from motion algorithms), it would be possible to fully adjust scene parallax. One example scenario where this ability would be useful is to transform the viewpoints of the cameras of the stereo pair to match the viewpoints of the user's eyes. It is advantageous to mount the cameras as close to the head as possible to minimize the lever arm with respect to the head, as this makes the most stable image; a preferred mounting position is therefore on the crown of the user's head. The vertical displacement of the stereo camera pair relative to the user's eyes introduces vertical parallax to the viewed image that can be mitigated via the appropriate transformation. While spatially resolved depth information would enable a full correction of scene parallax, it is also possible to correct for the average scene parallax with only a point distance sensor. If the relative geometry of the eyepieces and the stereo camera pair is known, then the average scene parallax can be adjusted as a function of measured distance, by transforming or shifting the image of the subject such that it appears as if the stereo camera pair were always directed toward the subject.

Additional cameras can be used to include other modalities, such as fluorescence imaging, polarization imaging, hyperspectral imaging, etc. With an imaging depth sensor, it is possible to mount, for example, an NIR fluorescence imager, a polarization imager, and a color RGB stereo pair side by side, and use the spatially resolved depth information to correct for parallax and map fluorescence or other information onto the viewpoints of the stereo camera pair, or onto the viewpoints of the user's eyes. The processor can include extrinsic and intrinsic camera calibration matrices or other camera models in order to properly map between the different viewpoints with minimal registration error and without requiring computationally costly and error-prone iterative registration algorithms.

It is an aspect of the present disclosure to provide a novel form of multi-channel imager that is more amenable to a digital loupe than those of the prior art. Here, multi-channel imager refers to imaging modalities that are traditionally thought of as using a single device, such as a hyperspectral imager or imaging polarimeter, that outputs an "image cube", which is a stack of individual 2D images corresponding to single channels such as wavelength bands or polarization components, etc. Such imaging technologies may be large and bulky and thus not amenable to integration in a digital loupe; also, depending on the technology, they may not have adequate spatial and/or temporal resolution or light throughput. Rather, by using a calibrated array of miniature cameras, each one recording one slice or channel of an image cube corresponding to a given modality, one can use information from an imaging depth sensor to remove parallax from each camera of the array and synthesize a full image cube as if it were recorded simultaneously from a single viewpoint. This technique of the present disclosure has an advantage over sensors that tile various spectral or polarization filters at the pixel level as it preserves spatial resolution and allows for flexibility of integration, choice of filters, and independent sensor and exposure parameters. Also, it has an advantage over temporally scanning sensors as there is no temporal scanning involved. Thus, the multi-channel imaging technique of the present disclosure enables real-time integration of images from multiple disparate optical imaging modalities within a digital loupe system.

The present disclosure is also directed toward ocular support structures especially suited for use in digital loupe systems. Throughout this disclosure, the word "ocular" can be used to describe any optical element or system of elements mounted in front of the eye for purposes of viewing or visualization by the eye, such as a telescope in the case of analog loupes, or an eyepiece, with or without an adjacent microdisplay, in the case of a head-mounted display or near-eye display. Many embodiments of the disclosure concern novel means of supporting and aligning an ocular in front of the eye of a user while improving upon the prior art in terms of better overall ergonomics, including peripheral vision, comfort, stability and adjustability, etc. One embodiment of this disclosure may occur within the context of a digital loupe system, such that the visual output of such a system can be displayed in a manner that allows for comfortable, stable use over the multiple hours of a surgical operation, allowing the surgeon to select the most ergonomic operating positions while minimizing the occlusion to the surgeon's peripheral vision.

Embodiments of this disclosure comprise judicious placement of the support arm or support arms of an ocular with respect to the anatomy of a human head. In some embodiments, ocular support arms or systems described herein do not include the lens barrel or immediate enclosure of a lens or ocular. Rather, they comprise the linkage that mechanically connects the ocular to the user, or any number of mechanical linkages away from the ocular, starting with the most adjacent one. Embodiments of the present disclosure may comprise ocular support arms, structures, or systems, that keep weight off the nose and other sensitive parts of the head and face while maintaining as much peripheral vision, or as much of an open view, as possible. Some embodiments are directed toward ocular support systems comprising multiple articulation points that enable full positioning adjustment of the oculars, or components of such systems, such as headbands, that better enable such systems to perform as desired. Other embodiments are directed toward placement of ocular support arms with respect to the wearer's head, or with respect to the user's field of vision. Further embodiments take into account relative placement of the stereo camera pair, such that the declension of the stereo camera pair can be separately adjusted from that of the ocular, enabling both a more vertical operating posture as well as concurrence of a view of a subject through the ocular as captured by the stereo camera pair and a view of the same subject above or below the ocular.

A digital loupe system is provided, comprising a stereo camera pair adapted and configured to generate image signals of an object or work area, a distance sensor adapted and configured to obtain a measurement of distance to the object or work area; and a processor operably connected to the stereo camera pair and the distance sensor, wherein the processor comprises a memory configured to store camera calibration information relating to the stereo camera pair and to perform a transformation to image signals from the stereo camera pair based on a distance measurement from the distance sensor and the camera calibration information.

In some implementations, the transformation causes the image signal to appear as if generated from a stereo camera pair with optical axes that converge at a distance corresponding to the distance measurement.

In other implementations, the distance sensor has a field of view that is adjustable. In some examples, the field of view of the distance sensor is adjustable based on a magnification of the digital loupe system. In other implementations, the optical axis of the distance sensor approximately bisects the angle formed by the optical axes of the stereo camera pair. In another implementation, the distance sensor is an imaging distance sensor. In another implementation, the distance sensor has a narrow, collimated beam.

In one embodiment, the stereo camera pair is adapted to be mounted on the crown or forehead of a user's head.

In some implementations, a declination angle of the stereo camera pair is adjustable.

In other implementations, each camera of the camera pair has an optical axis, the optical axes of the stereo camera pair being configured to converge at a distance approximately equal to an intended working distance of a user.

In some examples, the digital loupe system further comprises a binocular head-mounted display comprising first and second displays operably connected to the processor to receive the image signals from the processor generated by the stereo camera pair and to display images from the image signals. In some examples, the transformation causes the images to appear as if the stereo camera pair had optical axes that converge at a distance corresponding to the distance measurement. In other implementations, the head-mounted display is configured to have a virtual image distance corresponding approximately to a working distance of a user. In some implementations, the displays are mounted in a near-vision position. In another implementation, the processor is further configured to display the image signals in the displays with a spatially-varying magnification. the binocular head-mounted display can further comprise an ambient light sensor, the processor being further configured to use a signal from the ambient light sensor to adjust a display characteristic of the head-mounted display. In some examples, the optical axes of the head-mounted display converge at a distance approximately equal to a working distance of a user.

In some implementations, the processor of the digital loupe system is further configured to use distance information from the distance sensor to shift a viewpoint of the image signals.

In another implementation, the stereo camera pair comprises a color camera that provides color image signals to the processor. In some implementations, the processor is further configured to process the color image signals using a 3-dimensional look-up table. In other examples, the processor is further configured to process the color image signals to substitute colors from a region in a color space where a user is less sensitive to changes in color to a second region in the color space where a user is more sensitive to changes in color.

In some embodiments, the system is configured to perform image stabilization through optical image stabilization at the stereo camera pair or through electronic image stabilization at the processor.

In other embodiments, the cameras are configured to automatically maintain focus.

In one implementation, the system further comprises a source of illumination adapted to illuminate the object or work area. In some examples, the source of illumination is controlled by an illumination controller that adjusts a parameter of the illumination based upon measurements of distance from the distance sensor. In other examples, the illumination may be pulsed in a manner synchronized with an exposure interval of the stereo camera pair.

In some examples, at least one image sensor in the stereo camera pair is an RGB-IR sensor. In another implementation, the at least one image sensor has a high dynamic range capability.

In some examples, the system further comprises an additional imaging modality different from the one that the stereo pair comprises. For example, the additional imaging modality can comprise a multi-channel imaging system.

A multi-channel imaging system is further provided, comprising an array of at least two cameras, wherein at least two channels are distributed across the at least two cameras, an imaging distance sensor adapted and configured to image a field of view similar to a field of view imaged by the at least two cameras, and a processor configured to store camera calibration information regarding the at least two cameras, wherein the camera calibration information is defined in a coordinate system relative to the imaging distance sensor, wherein the processor is configured to receive image signals from the at least two cameras and depth information from the imaging distance sensor and to use the depth information and the camera calibration information to correct for parallax between the at least two cameras, thus providing a multi-channel image that appears to originate from a single viewpoint.

In some implementations, the system is a multispectral imaging system, the channels correspond to spectral bands, and the multi-channel image comprises a hyperspectral image.

In another implementation, the system is an imaging polarimeter, the channels correspond to polarization combinations, and the multi-channel image comprises a polarimetry image.

A method of obtaining a stereoscopic image of an object is also provided, the method comprising obtaining first and second images of an object with first and second cameras, obtaining a measurement of distance to the object with a distance sensor, and applying a transformation to the first and second images using the measurement of distance and using calibration information of the first and second cameras.

In some examples, the method further comprises displaying the transformed first and second images on first and second displays, respectively. Additionally, the method can comprise supporting the first and second displays in a field of vision of a user. In some implementations, optical axes of the first and second displays converge at a distance approximately equal to a working distance between the user and the object. In one example, the step of applying the transformation comprises virtually adjusting the convergence angle of the first and second displays. In another example, the step of applying a transformation comprises causing the first and second images to appear on the first and second displays as if the first and second cameras had optical axes that converge at a distance corresponding to the measurement of distance.

In some embodiments, the applying step comprises adjusting a field of view of the first and second images using the measurement of distance.

In other embodiment, the method further comprises using the measurement of distance to shift a viewpoint of the first and second images.

In some implementations, the method further comprises changing a magnification of the first and second images and adjusting a field of view of the distance sensor with the change of magnification.

In another embodiment, the method further comprises changing the distance between the object and the first and second cameras and adjusting the transformation with the change in distance.

The method can additionally include illuminating the object. In some examples, the illuminating step comprises determining an illumination parameter based upon the measurement of distance and illuminating the object based on the illumination parameter. In another example, the illuminating step comprises pulsing an illumination source in a manner synchronized with exposure intervals of the first and second cameras.

A method of viewing an object is also provided, comprising engaging a head engagement member with a user's head, the head engagement member supporting two cameras above the user's head, placing each of a first display and a second display in a line of sight with an eye of the user, obtaining first and second images of the object with first and second cameras, obtaining a measurement of distance to the object with a distance sensor supported by the head engagement member, applying a transformation to the first and second images using the measurement of distance and using calibration information of the first and second cameras, and displaying the transformed first and second images on first and second displays, respectively.

In some implementations, the method further comprises supporting the first and second displays with the head engagement member.

In one example, optical axes of the first and second displays converge at a distance approximately equal to a working distance between the user and the object.

In one implementation, the step of applying the transformation comprises virtually adjusting the convergence angle of the first and second displays.

In another example, the step of applying a transformation comprises causing the first and second images to appear on the first and second displays as if the first and second cameras had optical axes that converge at a distance corresponding to the measurement of distance.

In some embodiments, the applying step comprises adjusting a field of view of the first and second images using the measurement of distance.

In other embodiments, the method further comprises using the measurement of distance to shift a viewpoint of the first and second images.

In another embodiment, the method further comprises changing a magnification of the first and second images and adjusting a field of view of the distance sensor with the change of magnification.

In some examples, the method further comprises changing the distance between the object and the first and second cameras and adjusting the transformation with the change in distance.

In one embodiment, the method further comprises illuminating the object with an illumination source supported by the head engagement member. In some examples, the illuminating step comprises determining an illumination parameter based upon the measurement of distance and illuminating the object based on the illumination parameter. In other examples, the illuminating step comprises pulsing an illumination source in a manner synchronized with an exposure interval of the first and second cameras.

A method of obtaining a multi-channel image is also provided, the method comprising obtaining at least first and second images of an object from at least first and second cameras, obtaining a depth image of an object using an imaging depth sensor, and applying a transformation to the at least first and second images based on the depth image and calibration information of the at least first and second cameras, wherein the at least first and second images correspond to single channels of a multi-channel imaging modality, and the transformation removes parallax between the at least first and second images.

In some examples, the channels correspond to spectral bands, and the multi-channel image comprises a multispectral image. In other examples, the channels correspond to polarization combinations, and the multi-channel image comprises a polarimetry image.

A head mounting system for supporting a pair of oculars within a line of sight of a human user is also provided, the head mounting system being adapted to be worn by the user, the system comprising a head engagement member adapted to engage the user's head, and first and second support arms each having a proximal portion supported by the head engagement member, a distal portion disposed so as to support an ocular in the user's line of sight, and a central portion disposed between the proximal portion and the distal portion, the head mounting system being configured such that when the head engagement member is engaged with the user's head, the central portion of each support arm is configured to extend laterally and superiorly from the distal portion toward the proximal portion without extending through a region of the user's face medial and superior to the user's eyes and inferior to the user's glabella, and the proximal portion of each support arm is arranged and configured to be disposed medial to the central portion.

In some implementations, the proximal portion of each support arm is further configured to be disposed medial to the user's frontotemporales when the head engagement member is engaged with the user's head.

In one embodiment, the central portion of each support arm is further configured to extend posteriorly from the distal portion toward the proximal portion without extending through a region of the user's face medial and superior to the user's eyes and inferior to the user's glabella when the head engagement member is engaged with the user's head.

In some examples, the proximal portions of the first and second support arms are each connected to the head engagement member by a hinge adapted to allow an angle between the support arms and the head engagement member to be changed. In one implementation, the hinge is adapted to allow the proximal, central, and distal portions of the support arms to be moved above the user's eyes when the head engagement member is engaged with the user's head.

In some examples, the first and second support arms are each supported by a sliding connector allowing a height of the support arms with respect to the head engagement member to be changed.

In another embodiment, each of the first and second support arms comprises multiple segments. In one embodiment, the system further comprises a connector connecting adjacent segments of each support arm. In some implementations, the connector is adapted and configured to allow an effective length of a segment of the support arm to be adjusted.

In one example, the distal portion of each of the first and second support arms comprises a display bar adapted to be connected to an ocular of the pair of oculars. In one embodiment, the first support arm display bar is integral with the second support arm display bar. In another embodiment, the first support arm display bar and the second support arm display bar are not connected. In another embodiment, the system further comprises first and second hinges connecting the display bar to the central portions of the first and second support arms, respectively. In one example, the hinges are adapted and configured to allow a declension angle of oculars attached to the display bar to be changed. In another example, the hinges are adapted and configured to allow the first and second support arms to be moved toward or away from the user's head.

In some embodiments, the head engagement member comprises a headband. In some examples, the headband is adjustable to fit different user head sizes.

In one embodiment, the head engagement member comprises a plurality of pieces adapted to engage the user's head, the plurality of pieces being connected by a flexible connector.

In another embodiment, the head engagement member comprises a connector adapted to connect to a head strap.

In some embodiments, the first and second support arms are two ends of a unitary support arm. In one example, the unitary support arm has a ram's horn shape. In another example, the unitary support arm has a partial rectangle shape.

In some embodiments, the system further comprises a transparent window attached to the ocular supports and adapted to protect the user's face.

In other embodiments, the system comprises a sensor configured to report a state of an articulation of the head mounting system.

In one example, an articulation of the head mounting system is adapted to be automatically actuated.

In one implementation, the system further comprises a linkage between the first and second support arms, the linkage being configured to actuate a portion of one of the support arms in response to an actuation of a corresponding portion of the other support arm.

An imaging system adapted to be worn by a human user to provide a view of a work area is further provided, the system comprising a head mounting subsystem for supporting a pair of oculars within a line of sight of a human user, the head mounting system being adapted to be worn by the user, the head mounting subsystem comprising a head engagement member adapted to engage the user's head, and first and second support arms each having a proximal portion supported by the head engagement member, a distal portion disposed so as to support an ocular in the user's line of sight, and a central portion disposed between the proximal portion and the distal portion, the head mounting system being configured such that when the head engagement member is engaged with the user's head, the central portion of each support arm is configured to extend laterally and superiorly from the distal portion toward the proximal portion without extending through a region of the user's face medial and superior to the user's eyes and inferior to the user's glabella, and the proximal portion of each support arm is arranged and configured to be disposed medial to the central portion, two cameras supported by the head engagement member, first and second oculars supported by the distal portions of the first and second support arms, respectively, so as to be positionable in the user's line of sight when the head engagement member is engaged with the user's head, and a processor adapted and configured to display in displays of the oculars images obtained by the two cameras.

In some embodiments, the proximal portion of each support arm is further configured to be disposed medial to the user's frontotemporales when the head engagement member is engaged with the user's head.

In one embodiment, the central portion of each support arm is further configured to extend posteriorly from the distal portion toward the proximal portion without extending through a region of the user's face medial and superior to the user's eyes and inferior to the user's glabella when the head engagement member is engaged with the user's head.

In another embodiment, the proximal portions of the first and second support arms are each connected to the head engagement member by a hinge adapted to allow an angle between the support arms and the head engagement member to be changed. In some examples, the hinge is adapted to allow the proximal, central, and distal portions of the support arms to be moved above the user's eyes when the head engagement member is engaged with the user's head.

In one embodiment, the first and second support arms are each supported by a sliding connector allowing a height of the support arms with respect to the head engagement member to be changed.

In some implementations, each of the first and second support arms comprises multiple segments. In one example, the system further comprises a connector connecting adjacent segments of each support arm. In other embodiments, the connector is adapted and configured to allow an effective length of a segment of the support arm to be adjusted.

In one implementation, the system further comprises first and second ocular supports adapted to change a distance between the oculars.

In some examples, the head mounting subsystem is configured to permit a declension angle of the oculars with respect to the user's line of sight to be changed.

In another implementation, the distal portion of each of the first and second support arms comprises a display bar supporting the first and second oculars. In one example, the first support arm display bar is integral with the second support arm display bar. In another example, the first support arm display bar and the second support arm display bar are not connected. In one embodiment, the system further comprises first and second hinges connecting the display bar to the central portions of the first and second support arms, respectively. In one embodiment, the hinges are adapted and configured to allow a declension angle of the oculars to be changed. In another embodiment, the hinges are adapted and configured to allow the first and second arms to be moved toward or away from the user's head.

In some examples, the head engagement member comprises a plurality of pieces adapted to engage the user's head, the plurality of pieces being connected by a flexible connector.

In other examples, the first and second support arms are two ends of a unitary support arm.

In some embodiments, each of the first and second support arms has a ram's horn shape.

In another embodiment, each of the first and second support arms has a partial rectangle shape.

In one embodiment, the system further comprises a transparent window attached to the ocular supports and adapted to protect the user's face.

In another example, the system further includes a distance sensor supported by the head engagement member.

The system can comprise a camera mount movable with respect to the head engagement member to change a view angle of one or both of the cameras.

In one implementation, the system further comprises a transparent window extending in front of the displays and adapted to protect the user's face.

In some embodiments, the system further includes a source of illumination supported by the head engagement member.

In another implementation, the system includes a sensor configured to report a state of an articulation of the head mounting system.

In some implementations, an articulation of the head mounting system is adapted to be automatically actuated.

In another example, the system includes a linkage between the first and second support arms, the linkage being configured to actuate a portion of one of the support arms in response to an actuation of a corresponding portion of the other support arm. In one example, the linkage comprises a sensor configured to sense an actuation state of the portion of one of the support arms and report the actuation state to the processor and an actuator configured to actuate the corresponding portion of the other support arm and to receive commands generated by the processor, the processor configured to generate commands to the actuator in response to a report received from the sensor.

In one embodiment, the head engagement member comprises a headband. In some examples, the headband is adjustable to fit different user head sizes.

In another embodiment, the head engagement member comprises a connector adapted to connect to a head strap.

A method of viewing a work area is also provided, comprising engaging a head engagement member with a user's head, the head engagement member supporting two cameras above the user's head, placing each of two oculars in a line of sight with an eye of the user, the first and second oculars supported by first and second supports arms, respectively, positioned such that a central portion of each support arm extends laterally and superiorly from the oculars toward the head engagement member without extending through a region of the user's face medial and superior to the user's eyes and inferior to the user's glabella, supporting each of the first and second support arms at a position of the head engagement member medial to the central portion of the first and second support arms, respectively; and displaying in the oculars images of the work area obtained by the cameras.

In some examples, the supporting step comprises supporting each of the first and second support arms at a position of the head engagement member medial to the user's frontotemporales.

In one embodiment, the central portion of each support arm also extends posteriorly from the distal from the oculars toward the head engagement member without extending through a region of the user's face medial and superior to the user's eyes and inferior to the user's glabella when the head engagement member is engaged with the user's head.

In some examples, the method further includes viewing the work area along a line of sight extending over the oculars.

In another implementation, the method further includes viewing the work area along a line of sight extending under the oculars.

In one embodiment, the method further includes viewing the work area simultaneously through the oculars and around the oculars.

In another example, the method includes moving the oculars upward with respect to the user's eyes.

In some implementations, the method comprises moving the oculars downward with respect to the user's eyes.

In another example, the method comprises changing a distance between the oculars.

In some embodiments, the method further includes adjusting a shape of the head engagement member to fit the user's head.

In some examples, the method includes moving at least one of the first support arm and the second support arm medially or laterally.

In another example, the method includes moving the first and second support arms above the user's eyes.

In some implementations, the method further comprises obtaining a measurement of distance from the cameras to the work area and applying a transformation to images obtained by the cameras to create transformed images, the displaying step comprising displaying the transformed images on the oculars. In one example, the step of obtaining a measurement of distance from the cameras to the work area is performed by using a distance sensor supported by the head engagement member. In another example, the step of applying the transformation comprises virtually adjusting the convergence angle of the first and second oculars. In one implementation, the step of applying a transformation comprises causing the first and second images to appear on the first and second oculars as if the first and second cameras had optical axes that converge at a distance corresponding to the measurement of distance.

In one example, the method further comprises illuminating the object. In one example, the illuminating step comprises determining an illumination parameter based upon the measurement of distance and illuminating the object based on the illumination parameter. In another example, the illuminating step comprises pulsing an illumination source in a manner synchronized with exposure intervals of the first and second cameras.

In another embodiment, the method further comprises moving at least one of the first and second support arms automatically.

In some embodiments, the method includes automatically moving at least part of the second support arm in response to movement of a corresponding part of the first support arm.

In one example, the method includes sensing an actuation state of one of the support arms.

A head mounting system for supporting an ocular within a line of sight of a human user is provided, the head mounting system being adapted to be worn by the user, the system comprising head engagement member adapted to engage the user's head, and a support arm having a proximal portion supported by the head engagement member, a distal portion disposed so as to support an ocular in the user's line of sight, and a central portion disposed between the proximal portion and the distal portion, the head mounting system being configured such that when the head engagement member is engaged with the user's head, the central portion of the support arm is configured to extend laterally and superiorly from the distal portion toward the proximal portion without extending through a region of the user's face medial and superior to the user's eyes and inferior to the user's glabella, and the proximal portion of the support arm is arranged and configured to be disposed medial to the central portion.

In some embodiments, the proximal portion of the support arm is further configured to be disposed medial to the user's frontotemporales when the head engagement member is engaged with the user's head.

In another embodiment, the central portion of the support arm is further configured to extend posteriorly from the distal portion toward the proximal portion without extending through a region of the user's face medial and superior to the user's eyes and inferior to the user's glabella when the head engagement member is engaged with the user's head.

In some examples, the proximal portion of the support arm is connected to the head engagement member by a hinge adapted to allow an angle between the support arm and the head engagement member to be changed. In one embodiment, the hinge is adapted to allow the proximal, central, and distal portions of the support arms to be moved above the user's eyes when the head engagement member is engaged with the user's head.

In some implementations, the support arm is supported by a sliding connector allowing a height of the support arm with respect to the head engagement member to be changed.

In another example, the support arm comprises multiple segments. In some examples, the system further comprises a connector connecting adjacent segments of the support arm. In one example, the connector is adapted and configured to allow an effective length of a segment of the support arm to be adjusted.

In some embodiments, the distal portion of the support arm comprises a display bar adapted to be connected to an ocular of the pair of oculars. In one example, the system further comprises a hinge connecting the display bar to the central portion of the support arm.

In some embodiments, the hinge is adapted and configured to allow a declension angle of an ocular attached to the display bar to be changed. In one example, the hinge is adapted and configured to allow the support arm to be moved toward or away from the user's head.

In one embodiment, the head engagement member comprises a headband. In some examples, the headband is adjustable to fit different user head sizes.

In another implementation, the head engagement member comprises a plurality of pieces adapted to engage the user's head, the plurality of pieces being connected by a flexible connector.

In some examples, the head engagement member comprises a connector adapted to connect to a head strap.

In another embodiment, the support arm has a ram's horn shape. In another example, the support arm has a partial rectangle shape.

In some implementations, the system includes a transparent window attached to the ocular support and adapted to protect the user's face.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIGS. 12A-12D depict different views and articulation states of another ocular support structure.

FIGS. 13A-13D depict different views and articulation states of yet another ocular support structure.

DETAILED DESCRIPTION

Figure 1:
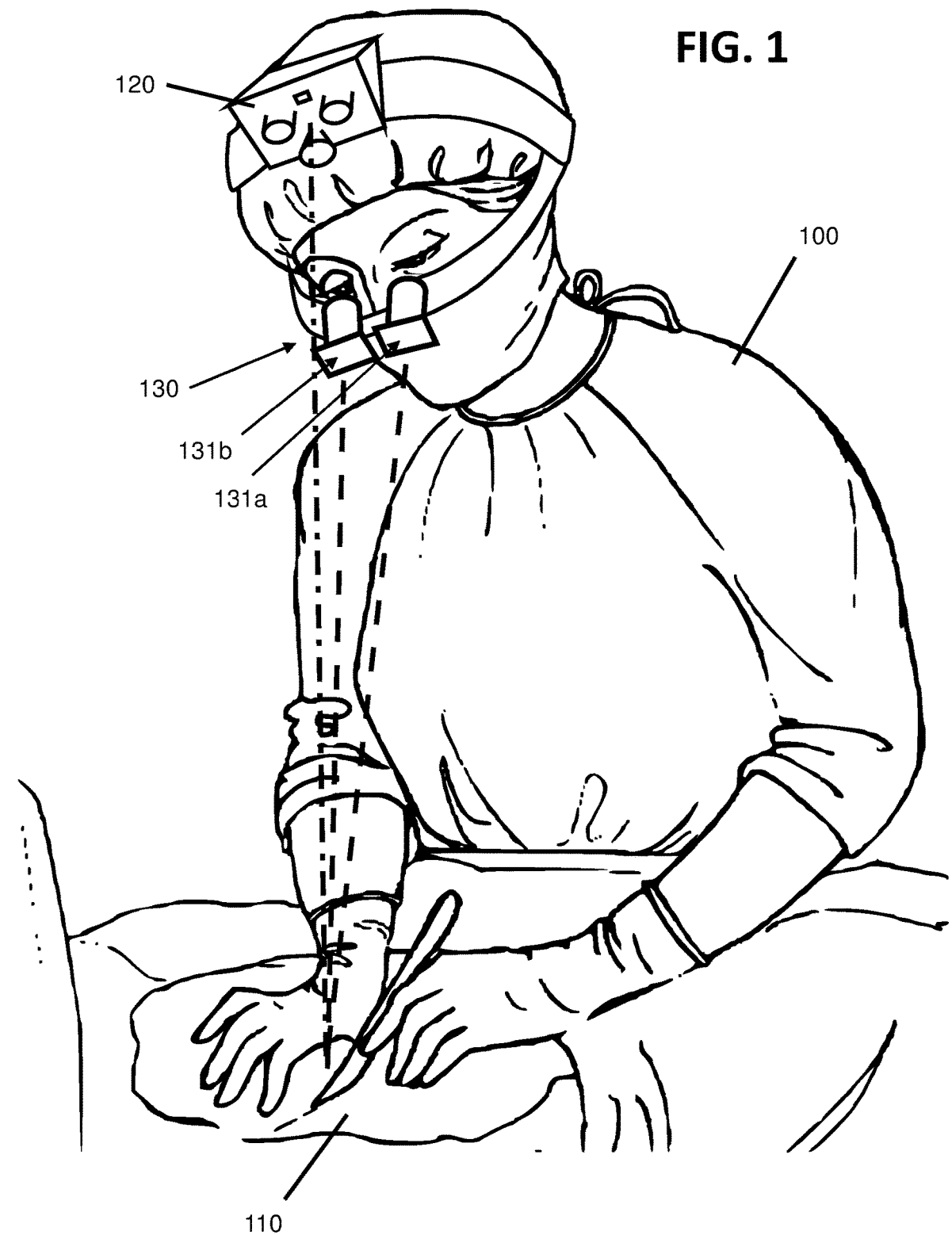
FIG. 1 shows a surgeon operating with an example embodiment of the present disclosure.

FIG. 1 depicts a surgeon 100 operating on a wound 110 (i.e., a target tissue site or a surgical work area) and wearing an example embodiment of the present disclosure, comprising a sensing/illumination unit 120 and a binocular head-mounted display (HMD) 130. The sensing unit 120 and HMD 130 are both operably connected to a processor, not shown. The sensing unit 120 comprises a stereo camera pair that receives a stereo image of the wound 110 and transmits the stereo image to the HMD 130. The HMD 130 has eyepieces or oculars 131a,b that are mounted in a "near" vision position familiar to those who wear traditional surgical loupes and also bifocals, in order to preserve "normal" or "far" vision. The surgeon 100 can either look directly at the wound 110, e.g., in the "far" vision position above the eyepieces of the HMD 130, or through the HMD 130 to see a magnified version of the wound 110. The virtual image distance of the HMD 130 is approximately the same as the working distance from the surgeon's eyes to the wound 110. Also, the optical axes of the HMD 130 converge to a nominal position of the surgical wound 110 relative to the surgeon 100. Therefore, when the surgeon 100 switches between looking directly at the wound 110 or through the HMD 130, there is minimal change in the accommodation or convergence of her eyesight. As will be explained further below with regard to system ergonomics, the sensing unit 120 is mounted on top of the surgeon's head in order to have a stable mounting platform, as the potentially high magnifications enabled by this system benefit from a stable mounting platform for the cameras. Also, the displacement of the sensing unit 120 with respect to the HMD 130, in a direction transverse to the optical axes of the HMD 130, is what enables the simultaneous and concurrent presence of the direct and magnified views of the surgical wound 110 in the surgeon 100's field of vision. The surgeon 100 can switch between centering the direct view or the magnified view of the wound 110 in the center of her field of vision with only an eye rotation and without the need to move her head. The direct view around the HMD and the augmented view in the HMD are therefore "concurrent." The placement and support of the oculars of the HMD 130 is such that an open view of the surgical wound 110 as well as the surgeon 100's surroundings is maintained for maximum contextual awareness during the surgical operation.

Note that as used herein, a stereo camera pair may comprise any electronic imaging device that outputs a signal that can be viewed stereoscopically with a suitable display. For example, it could comprise two color RGB cameras with a baseline separation, similar to the separation of two eyes on a person, that afford for slightly different viewpoints, thus providing a stereoscopic view when rendered on a binocular head-mounted display. Alternatively, it could comprise two infrared cameras, or other types of cameras or focal plane arrays. As another alternative, it could comprise a single plenoptic (lightfield) camera, where signals for left and right displays are virtually rendered by calculating the images derived from a shift in viewpoint. As yet another alternative, it could comprise a single camera and a depth imager, where the information combined from single camera and depth imager is used to simulate a second viewpoint for stereopsis.

Figure 2:
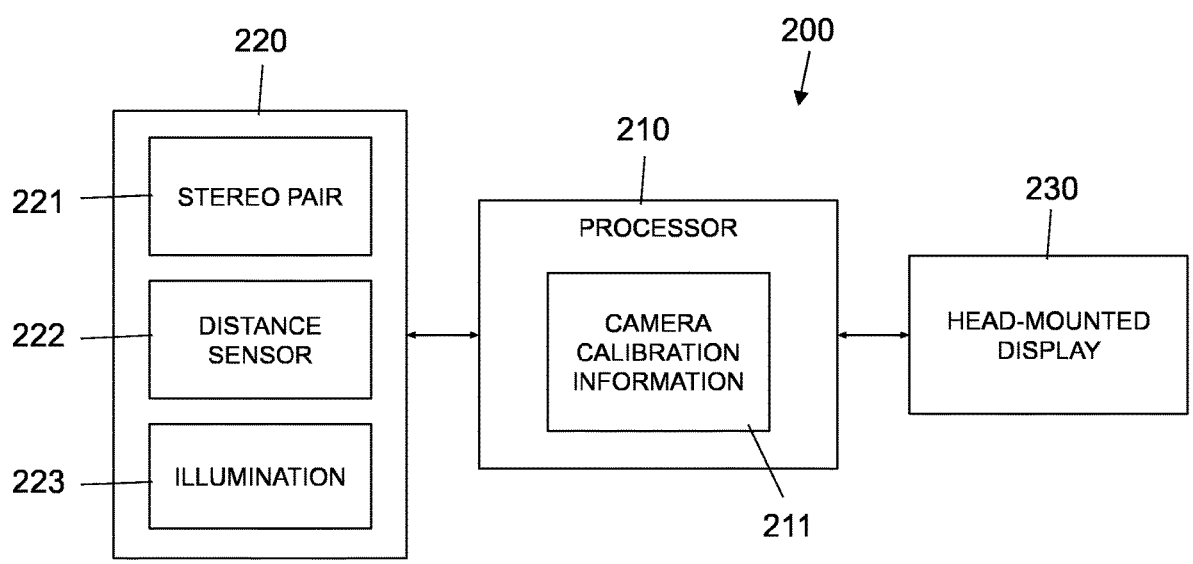
FIG. 2 shows a schematic diagram of an embodiment of the present disclosure.

FIG. 2 shows a schematic diagram 200 of an embodiment of the present disclosure. This embodiment comprises three main components: a processor 210, a sensing unit 220, and a head-mounted display (HMD) 230. The sensing unit 220 may comprise a stereo camera pair 221, a distance sensor 222, and an illumination source 223. The processor 210 may comprise camera calibration information in a memory module 211, and it may be used to control a magnification setting of embodiments of the present disclosure, based on input from the user such as voice commands, button presses, or gestures, or other means of capturing the user's intention. The processor 210 may receive information in the form of left and right images from the stereo camera pair 221 as well as distance measurements from the distance sensor 222. The processor 210 may be used to perform a transformation of the left and right images from the stereo camera pair 221 based on the camera calibration information and the distance measurements, especially to make the images appear to the user in a way that when displayed, they cause the eyes to converge to a nominal or actual working distance, and it may send the transformed images for display to HMD 230. The processor 210 may filter distance measurements over time, and it may adjust settings of the distance sensor 222, stereo camera pair 221, illumination source 223, or HMD 230. For example, it may adjust an integration time or field of view of the distance sensor 222 or an exposure time of the stereo camera pair 221 or illumination levels or spatial distribution of illumination source 223 based on image information from the stereo camera pair 221 or distance measurements from the distance sensor 222 or other sources of information, such as an ambient light sensor. The processor 210 may adjust a focus setting of one or both cameras of the stereo camera pair 221, and/or one or both the eyepieces of the HMD 230, and/or it may receive focus distance information from the stereo camera pair 221 and compare it with distance measurements of the distance sensor 222. Furthermore, the processor 210 may be used to control and/or perform optical and/or electronic image stabilization. Distance sensor 222 may comprise, for example, a time-of-flight sensor based on light or sound, or a sensor based on triangulation or capacitance, or any other known means of measuring a distance. The function of distance sensor 222 may be carried out by a stereo camera pair such as the stereo camera pair 221 and processor 210 in the sense that distance information can be calculated from the stereo disparity between images obtained from a calibrated stereo camera pair.

The illumination source 223 may comprise one or more different kinds of illumination sources, such as white LEDs designed with phosphors to cover a substantial portion of the visible spectrum, or LEDs or lasers used for fluorescence excitation, or multiple LEDs combined to form a wavelength tunable illumination source, or incandescent or plasma sources, such as a xenon arc lamp, either present on the sensing unit 220, or placed remotely but guided to the sensing unit 220 via a light guide, or placed remotely and guided via free-space propagation to the surgical wound. The processor 210 may pulse the illumination source 223 in synchronization with the exposure interval of the stereo camera pair 221 in order to achieve a shorter exposure time than would be possible with the same average illumination intensity but without pulsing; such pulsing is a useful strategy to mitigate motion blur at higher magnifications. The processor 210 can control the angular extent or angular/spatial distribution of the illumination beam exiting illumination source 223, potentially as a function of distance measured by the distance sensor 222, to match a field of view of the stereo camera pair 221, potentially as a function of the magnification of the digital loupe system. Variation of the angular and/or spatial extent and/or distribution of the illumination can be accomplished in multiple ways: by using a zoom optic in front of an LED; by using an array of individually addressable LEDs in front of a lens such that the illumination intensity profile at the surgical wound is controlled by the intensity setting of each LED; or, by employing other forms of tunable beam shaping, for example, those developed by LensVector™. The illumination source 223 can comprise multiple individually addressable LEDs of different wavelengths, with light mixed together and directed in a beam toward the subject. With such an arrangement, it is possible to capture multispectral images of the subject by time-sequential illumination with the different wavelengths, or even better for video-rate imaging, by time-multiplexing combinations of wavelengths, as in Park, Jong-Il, et al. "Multispectral imaging using multiplexed illumination." 2007 *IEEE* 11*th International Conference on Computer Vision*. IEEE, 2007.

Figure 3:
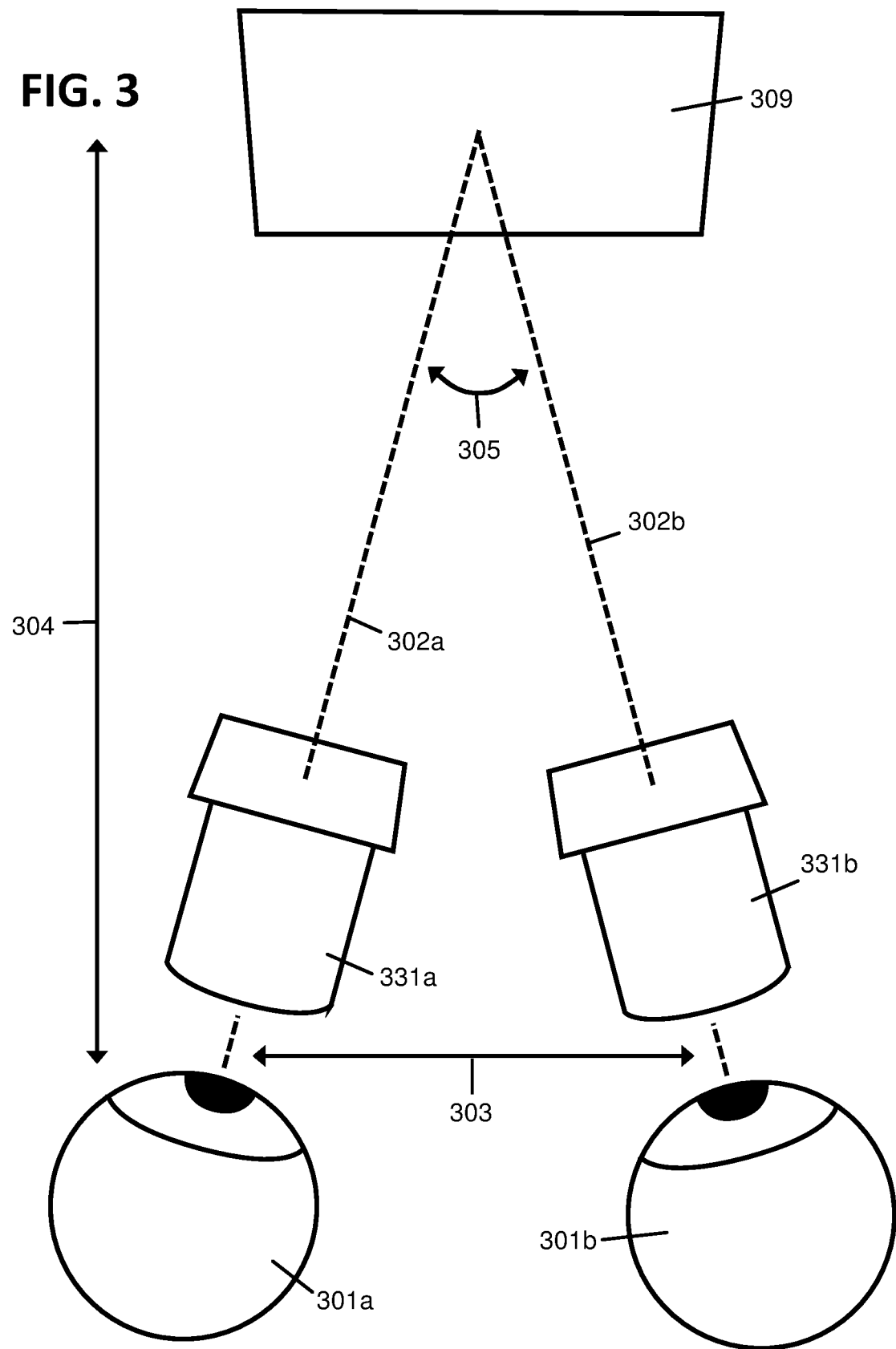
FIG. 3 shows a schematic diagram of an example binocular head-mounted display of the present disclosure, including a working distance and a convergence angle that are associated with a virtual image plane.

FIG. 3 depicts portions of a binocular head-mounted display of an embodiment of the present disclosure. A user's left and right eyes 301a,b look into corresponding near-eye displays/eyepieces 331a,b, of the head-mounted display with a fixed convergence angle 305. The head-mounting and support structure of the near-eye displays 331a,b (such as, e.g., one or more of the head-mount embodiments described below) permits the interpupillary distance (IPD) 303 of the displays to be adjusted so the optical axes of the near-eye displays/eyepieces 331a,b (and the centers of the displays) line up with the optical axes 302a,b of the user's eyes 301a,b, thus projecting the center of each display on the center of each corresponding eye's retina. A virtual image 309 of the near-eye displays 331a,b is set at a virtual image distance 304 corresponding to a nominal working distance of a user, by setting a proper focusing distance between the eyepieces and displays of near-eye displays/eyepieces 331a,b. The virtual image 309 at virtual image distance 304 is also where the optical axes 302a,b nominally intersect when aligned with optical axes of the near-eye displays/eyepieces 331a,b. Therefore, whether the user is looking through the near-eye displays/eyepieces 331a,b, or directly at an object or work area at the nominal working distance, there is little or no change in ocular accommodation or convergence, facilitating a seamless, comfortable transition between the two views. Furthermore, as will be explained later, the ergonomics of the digital loupe contemplated in the present disclosure are such that both the object or work area and the near-eye displays can be put into the user's field of vision simultaneously, a condition enabled by the transverse displacement of the stereo camera pair with respect to the optical axes of the near-eye displays.

Figure 4:
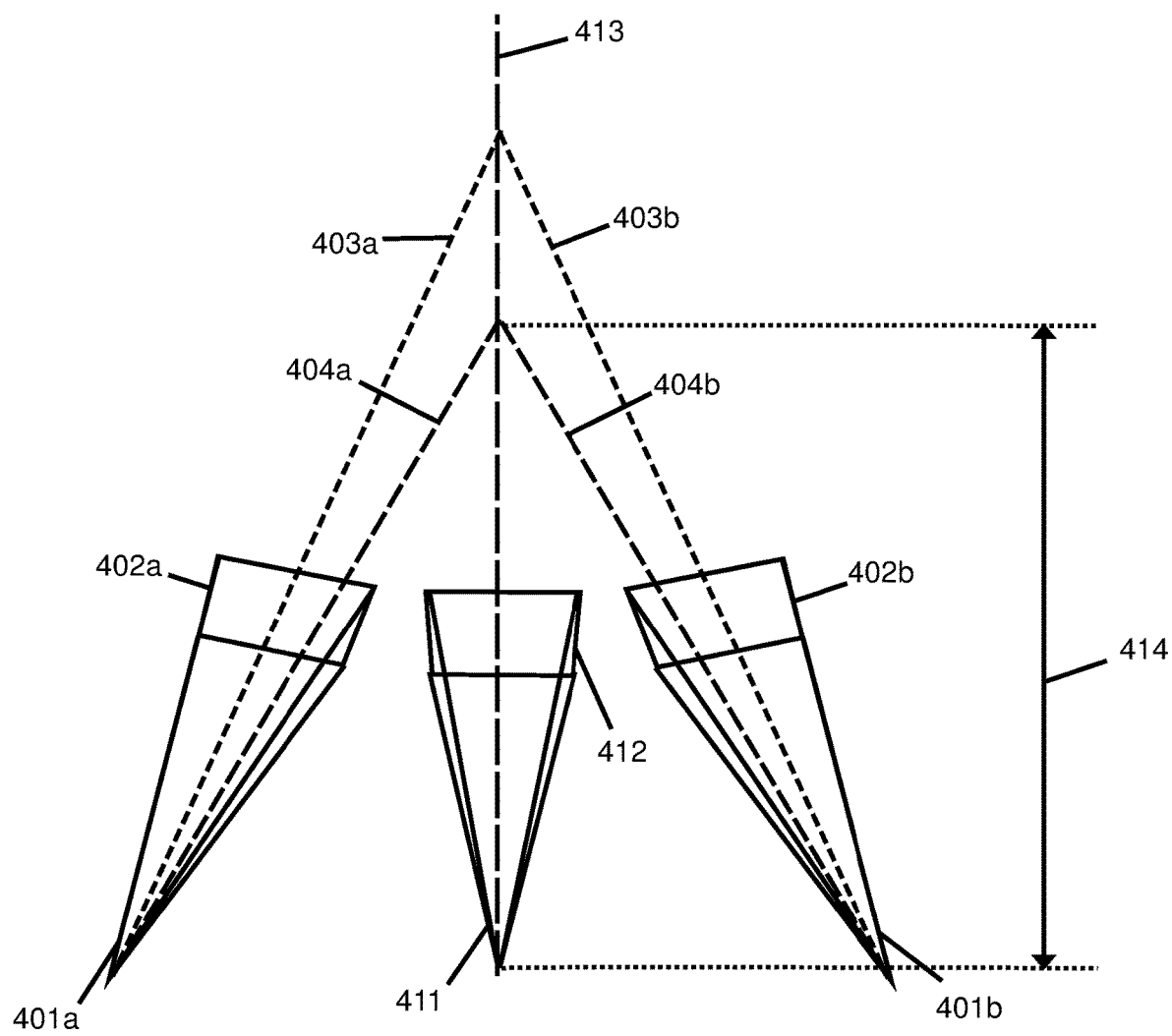
FIG. 4 is a schematic of a pair of cameras along with a distance sensor whose optical axis nominally bisects the optical axes of the pair of cameras.

As described above with respect to the digital loupe system of FIG. 1, some head-mounted display systems employ a distance sensor and a stereo camera pair to obtain images for display on near-eye displays. FIG. 4 depicts viewpoint frustums 401a,b indicating orientations and angular fields of view of a stereo camera pair of a head-mounted digital loupe system, with viewpoint frustum 411 of a distance sensor having an optical axis 413 that nominally bisects the angle between optical axes 403a,b of the stereo camera pair. Optical axes 403a,b correspond to the centers of the fields of view of frustums 401a,b. Optical axes 403a,b converge toward a point near the nominal working distance of the digital loupe's user, such that an object at their nominal convergence point is also at or near the nominal convergence point of the optical axes of the user's eyes (i.e., the convergence point of optical axes 302a,b in FIG. 3). For example, with reference to FIG. 3, interpupillary distance 303 may be 60 mm, and angle 305 may be 0.1 rad, so distance 304 may be approximately 600 mm, corresponding to a nominal working distance. Thus, an object point depicted at the center of each near-eye display 331a,b appears to be located at a distance of 600 mm from the user's eyes. With reference to FIG. 4, ideally optical axes 403a,b of stereo camera pair frustums 401a,b nominally converge at this same point 600 mm from the user's eyes. In practice, there may be slight angular misalignments of these optical axes from their ideal positions that will be dealt with subsequently.

The camera frustums 401a,b of the stereo pair may each have a field of view 402a,b that is larger than a field of view of near-eye displays 331a,b. Nominally, near-eye displays 331a,b depict a magnified view compared to what would be seen by the unaided eye. For example, angular magnifications in the range of 2× to 10× may be used. In some embodiments, the magnification may be approximately 1×, e.g., nominally unmagnified. One way to effect this magnification is to select a portion of the fields of view 402a,b of each camera for depiction on each display 331a,b at an enlarged size (e.g., cropping and zooming). Assume we select a portion of each field of view 402a,b around the optical axes 403a,b for display. As the magnification of the digital loupe system increases, the displayed portion of each field of view 402a,b shrinks around respective optical axis 403a,b. At high magnification, an object may disappear from displayed portions of the fields of view 402a,b if the object is not located near the nominal intersection point of optical axes 403a,b. Also, if there are slight misalignments in the optical axes 403a,b, e.g., if they do not intersect, it may not be possible to view a magnified object with single vision, as the magnified object will be displaced differently when viewed by each eye 301a,b based on the exact misalignments of each optical axis 403a,b.

The solution to both of these problems is to use information from the distance sensor represented by frustum 411, with potentially adjustable field of view 412, and optical axis 413, along with camera calibration information regarding cameras represented by frustums 401a,b, in order to compute a transformation of the images from cameras represented by frustums 401a,b prior to cropping and zooming. For example, suppose an object is located at distance 414 along the optical axis 413 of the distance sensor. If cameras represented by frustums 401a,b had optical axes directed toward this object, e.g., directed along axes 404a,b, they would record this object in the center of their fields of view 402a,b and therefore it would be displayed at the center of each display 331a,b, providing comfortable single vision without issue. However, because the object does not appear in the center of the fields of view 402a,b, it may not be possible to comfortably view the magnified object without diplopia or even at all through near-eye displays 331a,b.

In order to remedy this, the system can compute a transformation of images from cameras represented by frustums 401a,b that depends on distance measurements from distance sensor represented by frustum 411 and camera calibration information (stored, e.g., in the system's memory module 211 in FIG. 2) to make the images appear as if the detected object at distance 414 were measured at the center of the fields of view 402$a,b$, that is, as if the axes 404$a,b$ were also the optical axes of the cameras represented by frustums 401$a,b$. To do this we make extensive use of the pinhole camera model, a useful mathematical abstraction for relating the position of points in a 3-dimensional (3D) object space, corresponding to the real world, to positions in a 2-dimensional (2D) image space, corresponding to pixel coordinates within an image. The operations referenced herein, including camera calibration to obtain camera matrices and affine transformations to transform images between viewpoints based on camera calibration information, are available as software routines in most computer vision software packages such as OpenCV. A convention routinely seen in such software packages for the operations referenced herein is the use of homogeneous coordinates and the mathematics of projective geometry. A 3D object point X can be written in 4D homogeneous coordinates, and a 2D image point y can be written in 3D homogeneous coordinates. Neglecting image distortion (as it is known in the art how to deal with image distortion in this process), the mapping between object and image space can be performed by multiplying the object point X by a (3×4) camera matrix in order to obtain the image point y. The camera matrix comprises both extrinsic parameters relating to camera position and orientation, and intrinsic parameters relating to focal length, optical center of the image, and pixel size. It is known in the art how to obtain the parameters of such a camera matrix of both single- and multi-camera systems, through a procedure known as camera calibration, for example using routines available in OpenCV. Camera calibration information may also be obtained using, e.g., the process described in Zhang, Z., "A Flexible New Technique for Camera Calibration," Microsoft Corporation Technical Report MSR-TR-98-71 (Dec. 2, 1998). Both the camera matrix and a matrix representing the inverse transform—mapping from coordinates in a given image to coordinates in the real world, up to a scale factor—can be obtained. The inverse transform is known only up to a scale factor corresponding to the depth or distance of the object point away from the camera. However, if this distance is known, then the object point corresponding to an image point of the camera can be unambiguously determined, aiding in the registration of image points recorded from different camera viewpoints yet corresponding to the same object point.

A camera matrix can be decomposed into a matrix of its intrinsic parameters and a matrix of its extrinsic parameters, with the full camera matrix a product of these two. The matrix of extrinsic parameters corresponds to a rigid transformation potentially comprising both rotation and translation. Let us call the camera matrix for each camera i of the stereo pair represented by frustums 401$a,b$ $W_i$, which can be decomposed into intrinsic components $C_i$ and extrinsic components $H_i$ such that $W_i = C_i H_i$. The optical axes 403$a,b$ of cameras represented by frustums 401$a,b$ nominally intersect at a certain working distance, perhaps with slight misalignments relative to their designed directions, as well as slight misalignments with respect to the center of each corresponding image sensor. Assume that distance sensor represented by frustum 411 is at the origin of a 3D Cartesian coordinate system, and a distance measurement to an object under observation is reported as a point along optical axis 413 with homogeneous coordinates $X=(0,0,z,1)^T$. This point can be transformed to an image point with camera matrix $W_i$, e.g., $y_i = W_i X$. Image point $y_i$ is now taken to be the center of the image from camera i, thus cropping and zooming of this image takes place around this new image center. After cropping and zooming and display of the image in the corresponding near-eye display 331$a,b$, the object point corresponding to the intersection of distance sensor optical axis 413 with the object under observation would appear at the center of each near-eye display 331$a,b$.

Another way to transform the images from cameras represented by frustums 401$a,b$ would be to assume that the entire object under observation is planar and perpendicular to optical axis 413 at measured distance z from the distance sensor represented by frustum 411. Each image point $(a, b, 1)^T$ of an image from camera i, expressed in homogeneous coordinates, is associated via the intrinsic camera matrix with a ray that emerges from the origin of that camera and passes through a point expressed in the camera's object-space coordinate system. This ray can be written $(x'w, y'w, w)^T$, where the prime indicates we are in the camera's coordinate system. This coordinate system can be transformed to the reference coordinate system of the distance sensor represented by frustum 411 using the inverse of the extrinsic camera matrix. If we assume the object lies in the plane perpendicular to optical axis 413 at measured distance z, we can solve for parameter w at each image point to get the coordinates of the assumed object point corresponding to each image point. This procedure is equivalent to calculating the intersection of a ray, associated with an image point, and the assumed planar object detected by distance sensor represented by frustum 411. For each camera i we can assign an ideal extrinsic camera matrix that aims the center of the camera toward the point X at measured distance z along optical axis 413; in FIG. 4, this would correspond to the redirection of camera frustums 401$a,b$ along axes 404$a,b$ if distance z were given by 414. We can transform image points to new image points, as if the camera were aimed at point X and assuming a planar object, by multiplying object point coordinates corresponding to each image point with this ideal extrinsic camera matrix and then with the intrinsic camera matrix. Although similar to the previous simpler procedure that translated a given image so its center lined up with a point along optical axis 413, this latter procedure is more general as it can capture the full homography between the observed image from camera i and an image with the camera in an ideal orientation (e.g., aimed at point X). However, assuming the ideal camera position and orientation is sufficiently close to the actual camera position, there is not a significant difference between the two procedures.

After completing the transformations enumerated in the above procedure, left and right images of an object or work area are displayed in, and centered with respect to, the left and right eyepieces of a head-mounted display, such as near-eye displays 331$a,b$ of FIG. 3. As the optical axes 302$a,b$ of these displays converge with angle 305 to a point at nominal working distance 304, which may be similar to the actual working distance, for example distance 414 of FIG. 4, the eyes 301$a,b$ will not have to significantly change convergence to look directly at the object or work area versus viewing the object or work area through near-eye displays 331$a,b$. Furthermore, it is possible for the processor 210 to virtually (by translation of displayed images to the left and right) or physically (by rotation of the near-eye displays 331$a,b$) adjust the convergence angle 305 of near-eye displays 331$a,b$, such that when left and right eyes 301$a,b$ look through near-eye displays 331$a,b$, they converge to the actual working distance corresponding to a measurement from the distance sensor 222 represented by frustum 411. It is also possible for the processor 210 to virtually or physically change the convergence angle 305 in proportion to the change in measured distance to the object or work area under observation. Finally, it is possible for the processor 210 to change the focus state of near-eye displays 331a,b to cause the virtual image plane 309 to match or track the actual working distance corresponding to measurements from the distance sensor 222. In this way, no or minimal change in visual accommodation and/or vergence state of eyes 301a,b would be needed to switch between viewing a subject directly, e.g., above or below near-eye displays 331a,b, and through the near-eye displays 331a,b.

It is a feature of the present disclosure that the distance sensor represented by frustum 411 may have a defined field of view 412 that may be adjustable. Distance measurements may come from those objects that are within the field of view 412 only. If this field of view is tied to the magnification of the digital loupe system, then as the magnification of the digital loupe increases, the field of view 412 of the distance sensor represented by frustum 411 can decrease. This is to ensure that the field of view 412 of the distance sensor represented by frustum 411 matches (or corresponds to) the field of view displayed to the user through near-eye displays 331a,b. The VL53L1X distance sensor from STMicroelectronics, Inc., a LiDAR time-of-flight sensor, affords such a feature of adjustable field of view. However, changing the field of view affects the amount of light collected in a given distance measurement, affecting measurement precision, and individual measurements may not be sufficiently precise to begin with, so some form of temporal filtering of the distance measurements is desired. The distance sensor represented by frustum 411 can be calibrated to ensure accuracy of its distance measurements under working conditions. Also, camera calibration information (e.g., orientation and position) can be referenced to calibration information of the distance sensor represented by frustum 411, e.g., the coordinate system defined by the position and orientation of the distance sensor represented by frustum 411.

In some embodiments, it may be preferable to have a distance sensor with a narrow, collimated beam, such as a laser-based time-of-flight distance sensor like the TF-Luna distance sensor from Benewake Co., Ltd., so there is minimal ambiguity about the actual distance measured within the field of view. Generally, time-of-flight sensors report the measured distance based on a statistic such as the mean time-of-flight of all collected photons. If the collected photons form a histogram of photon counts vs. distance that is bimodal (for example, if the active area of the distance measurement includes a distinct edge with a foreground object and a background object), the mean will be between the two peaks and thus the distance reported will not correspond to the center of either peak. Therefore, the optics of the distance sensor can be configured to have a narrow beam, minimizing the probability of encountering an ambiguous distance measurement scenario.

Additional possibilities are enabled if the distance sensor represented by frustum 411 is an imaging distance sensor that provides a spatially resolved map of points, or a point cloud, across its field of view. Consider the previous case concerning an assumed planar object at measured distance z along optical axis 413 and perpendicular to that axis. With spatially-resolved distance information, we can relax the assumption that the object is planar. The point cloud reported by the imaging distance sensor represents points on the surface of the object, and these points can be mapped to the camera coordinate system to associate each image point with an object surface point. The implication is that for each point in the image, we can find the precise object point in our reference coordinate system. Thus, we can reproject the object points of a given image using a new, virtual camera matrix, to view them as if they were imaged through a virtual camera that may have a different position, orientation, focal length, etc. For example, the sensing unit 120 is worn on the forehead of surgeon 100, but the headset 130 is worn naturally in front of the eyes. We can reproject the images derived from sensing unit 120 as if they were imaged by cameras at the positions of the eyes of the surgeon 100, especially if the relative position and orientation of the cameras and the surgeon's eyes is known at least approximately. This way, the effective viewpoint of the sensing unit 120 is the same as for the surgeon 100, reducing or eliminating parallax with respect to the viewpoint of the surgeon 100. Even without an imaging distance sensor, it may still be useful to perform this operation to remove the average parallax across the image, which could be done by once again assuming the object is planar at a distance z along the optical axis 413, and then reprojecting those assumed object points onto the viewpoint of the surgeon 100.

Returning to FIG. 2, note that processor 210 may be configured to update camera calibration information stored in memory 211 during operation of a digital loupe system, for example by going through a camera calibration routine as described in the above-referenced publication by Zhang. Alternatively, the processor 210 can identify similar features between the cameras of the stereo pair 221 and adjust camera calibration information 211 such that when the processor 210 transforms images of the stereo pair 221 using either a translation or a full homography, these similar features show up in similar locations for each eye of the binocular head-mounted display 230. This could be done using a self-calibration technique as described in Dang, T., et al., "Continuous Stereo Self-Calibration by Camera Parameter Tracking," IEEE Trans. Image Proc., Vol. 18, No. 7 (July 2009). This would be important for slight misalignments of the optical axes of the stereo pair 221 that might accrue over time during operation of the digital loupe system.

In another embodiment of the present disclosure, a multi-channel imager is provided that combines an array of multiple single-channel imagers and uses an imaging depth sensor to remove parallax from the multiple single-channel imagers, such that the multi-channel image appears to be derived from a single camera or viewpoint. The process of mapping one viewpoint to another may be identical to that used for the previously described embodiment of the present disclosure. For example, the multi-channel imager can include a processor configured to store camera calibration information relating to at least two cameras, wherein the calibration information is defined in a coordinate system relative to an imaging distance sensor of the system. A processor of the multi-channel imager may be configured to receive image signals from the cameras and depth information from the imaging distance sensor, and use the depth information and the camera calibration information in order to correct for parallax between the cameras, thus providing a multi-channel image that appears to originate from a single viewpoint. Some examples of multi-channel imagers are hyperspectral imagers or Stokes imaging polarimeters. Certainly, as in the prior art, an imaging depth sensor can be used to combine images from different modalities—for example, US 2018/0270474 A1 teaches that depth information can be used to register images acquired with diverse intraoperative optical imaging modalities, such as NIR fluorescence, color RGB, or hyperspectral imaging using a tunable liquid-crystal filter or a mechanical filter wheel. But so far no one has envisioned using depth information to enable a single-modality multi-channel imager. It is a conceptual leap from the prior art to consider that a multi-channel optical imager could be collectively formed out of an array of single-channel imagers arranged nominally in a plane transverse to their lines of sight, in conjunction with an imaging depth sensor that provides sufficient information to remove effects of parallax from the different positions of the imager array. The output of such a system would comprise a multi-channel image cube as if obtained from a conventional multi-channel imager, that is, from a single viewpoint.

Such a multichannel imager could be combined with the digital loupe system of the present disclosure to simultaneously provide other intraoperative optical imaging modalities within the magnified view of the digital loupe system. For example, the array of sensors of the envisioned multi-channel imaging system could comprise multiple individual spectral bands, such that taken together with parallax removed, the output would comprise a multispectral or hyperspectral image. This hyperspectral image can be analyzed and compared to prior information to determine regions of the surgical wound 110 comprising cancerous tissue to be resected. An image can be formed indicating the probability of cancerous tissue at each pixel location. This image can be combined, as an overlay or using known image fusion techniques, with the magnified image presented in the display 130 of the digital loupe system, so a surgeon 100 has a more precise map of where to resect tissue than from the magnified image alone.

Similarly, the channels of the multi-channel imager could each correspond to an independent Stokes polarization component. Thus, the multi-channel imager could comprise a Stokes imaging polarimeter. A Stokes imaging polarimeter would be a useful addition to a digital loupe because it could be used to provide images with reduced glare, either alone or by modifying the polarization of the illumination. If used in combination with circularly polarized illumination, the Stokes polarization image can potentially be used to visualize birefringent structures such as nerves, as described in Cha et al., "Real-time, label-free, intraoperative visualization of peripheral nerves and micro-vasculatures using multimodal optical imaging techniques", Biomedical Optics Express 9(3):1097.

Other embodiments of the digital loupe system capture enhancements with respect to the prior art. For example, as mentioned in the Background along with the associated drawbacks, U.S. Ser. No. 10/230,943 B2 teaches a type of digital loupe with integrated fluorescence imaging such that within one sensor, both NIR (fluorescence) and visible (RGB) light are recorded, with a modified Bayer pattern where pixels in both visible and infrared bands can be tiled on the same sensor. The stereo camera pair of the present disclosure could comprise one or more such sensors. A limitation of such a sensor is that the same exposure, gain, and other settings are used for the NIR and visible light as they are imaged simultaneously. However, certain modern image sensors have a high-dynamic-range (HDR) capability that successively takes multiple exposures with different exposure durations. One could take advantage of combining HDR with such an RGB-NIR sensor in order to separately optimize imaging conditions, e.g., exposure duration, for both visible and near-infrared light.

Some aspects of the present disclosure aim to enhance the user experience of a digital loupe system. For example, it may be desired to soften the edges of the displayed image in each eye, e.g., with digital vignetting, in order that the eye is not drawn to the sharp edges of the image.

The digital loupe system may include an ambient light sensor that detects the spectrum and/or intensity of the ambient light. It is well known that ambient light can affect a viewing experience, so a measurement of ambient light can be used to adjust, for example, the white point and the brightness setting of the head-mounted displays of the digital loupe system.

It may be useful to present the image in the digital loupes with a spatially variable magnification. For example, a center rectangular portion of the image in each near-eye display, perhaps covering an area extending 20% across each dimension of the field of view of each display, can be displayed with a magnification substantially higher than the surrounding portion. If this high magnification were used across the whole image, the user may lose context of portions of the object surrounding the displayed portion. However, with spatially variable magnification, it is possible to achieve both high magnification and persistence of context simultaneously.

The processor of a digital-loupe system can comprise the most general color-substitution algorithm, which is a 3-dimensional look-up table that substitutes a given color for another. It is known that the eye's response or sensitivity to different colors and intensities of light differs substantially from that of a standard color camera. For example, the eye is most sensitive to changes in light intensity at green wavelengths, and is less sensitive to changes in light intensity at red wavelengths and blue wavelengths. It is likely then that there is a loss of useful information between a color image as it is recorded and when it is displayed to a user. There are many red hues expected from imaging a surgical operation, primarily due to the presence of hemoglobin in blood, as well as other bodily pigments. Not only is the human eye less sensitive to red wavelengths, but typical electronic displays may have trouble reproducing the saturated reds that images of blood comprise, as they may be outside of the display gamut. In either case, it may be advantageous to shift red colors, especially saturated red colors, toward the green (e.g., make them yellow) in order that the eye can discriminate between more subtle variations in red-colored tissue. In effect, this increases the amount of perceptual information available to the user. This can easily be done with a 3-dimensional look-up table. Color substitution may also be dynamic or may be determined by an algorithm which may utilize machine learning.

Figure 5:
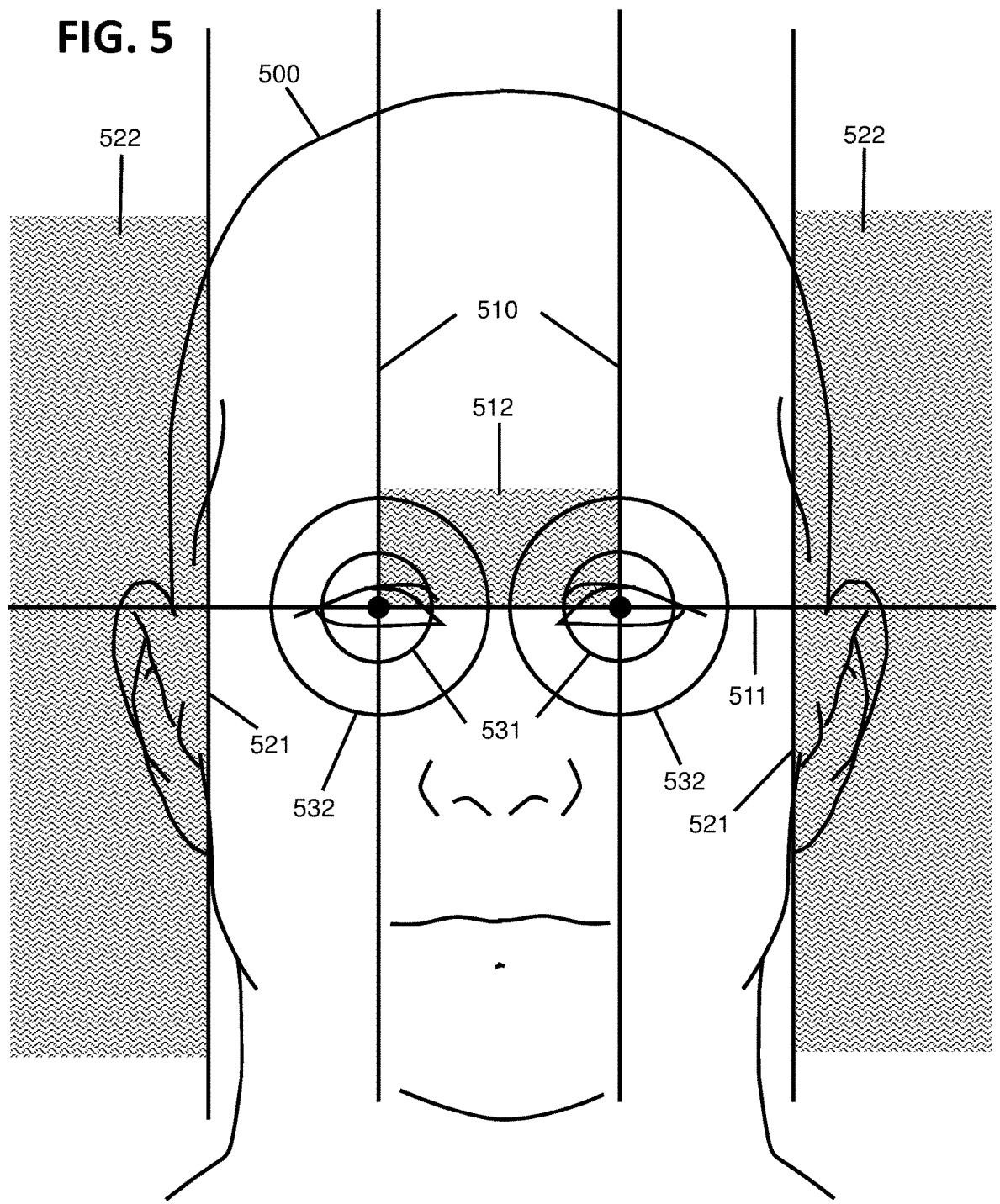
FIG. 5 depicts a front projection of a head delineating preferred regions for routing an ocular support arm.

Ergonomic enhancements are also provided in various embodiments of the present disclosure. FIG. 5 shows a frontal projection of a human head 500 with forward gaze. Note that this disclosure is not limited to a configuration that requires a forward gaze of a user; for example, a user might have a downward gaze. Vertical lines 510 intersect with horizontal line 511 at the pupil of each eye. Circles 531 and 532 are centered approximately with respect to the pupils such that an object within circle 531 will appear closer to the center of vision of the human depicted in FIG. 5 than an object within the circle 532 but not within the circle 531. Objects outside of the circles 532 will either appear within the human's peripheral vision (i.e., only at the edge of the human's vision) or will not be seen at all. Vertical lines 521 intersect the frontotemporales of the human head 500 to define regions 522 lateral to the frontotemporales. The frontotemporales are the most anterior points of the temporal ridges on either side of the frontal bone of the skull; the temporal ridges mark a sort of transition point between more vertically sloped portions of the skull on the lateral side, and more horizontally sloped portions on the medial side. Region 512 is medial and superior to the pupils, and extends vertically to about the top edge of the human's peripheral vision, approximately in line with the eyebrow ridge of head 500, or to the glabella, which is the point between the eyebrows.

Ocular supports of the prior art, when viewed in frontal projection upon the head 500, generally encroach upon, intersect with, or are mounted within region 512 and/or regions 522. For example, glasses-like supports utilize temple pieces that are supported by the ears within regions 522. Also, prior binocular head-worn magnifying loupes comprise a pair of simple magnifiers mounted in a visor that attaches to a headband on the sides of the head, lateral to the frontotemporales. Front-lens-mounted loupe systems or flip-up mounted systems typically have a support arm that descends from above within region 512 when viewed in frontal projection.

When viewed in a frontal projection upon head 500, ocular support systems or support arms of the present disclosure may support an ocular in a line of sight of the eye, then extend laterally, posteriorly, and superiorly (e.g., at least radially outward with respect to circles 531 and 532) while avoiding intersection with region 512, then extend to a head engagement member at positions that are medial to regions 522. Secondary support arms may intersect regions 512 and/or 522, for example to link together two oculars that are supported via primary support arms which follow the above-described pattern. A secondary support arm that links two oculars and crosses through region 512 can still be substantially outside of the peripheral vision of the user if it is routed in such a way that from the point of view of the user that it rests primarily behind the apparent field of view of the oculars. It is also beneficial if the image viewed through the oculars extends to the edge of the ocular. Although this approach makes the image edge blurry because the ocular edge is near to the eye and not in focus, the presence of this blurry image edge within the user's field of view obscures the ocular support arms even further, making the image appear as if it floats in front of the eye with minimal visible support. Also, the blurring at the edge of the image is useful to prevent the eye from being drawn to a sharp image edge, which could otherwise disturb binocular vision by providing conflicting binocular cues when two oculars are used in a binocular head-mounted display.

Specific head mounting systems for oculars employing ocular support arms that meet the general criteria as enumerated above are described in detail further below. They are preferable to ocular support systems with a primary support arm that descends through region 512 because they do not create the same uncomfortable sensation of having something immediately in front of the face. Extending the proximal ends of the ocular support arms to positions medial to the frontotemporales enables the head-mounted ocular support systems of this disclosure to accommodate different user head widths, which is easier to do if the proximal ends of the support arms extend to a head engagement member at or near the top of the head rather than to the sides of the head. In some embodiments, the two support arms are separate structures supported by the head engagement member. In other embodiments, the two support arms are part of a unitary structure supported centrally by the head engagement member and extending distally from the central support point to their respective oculars or ocular support structure.

Figure 6:
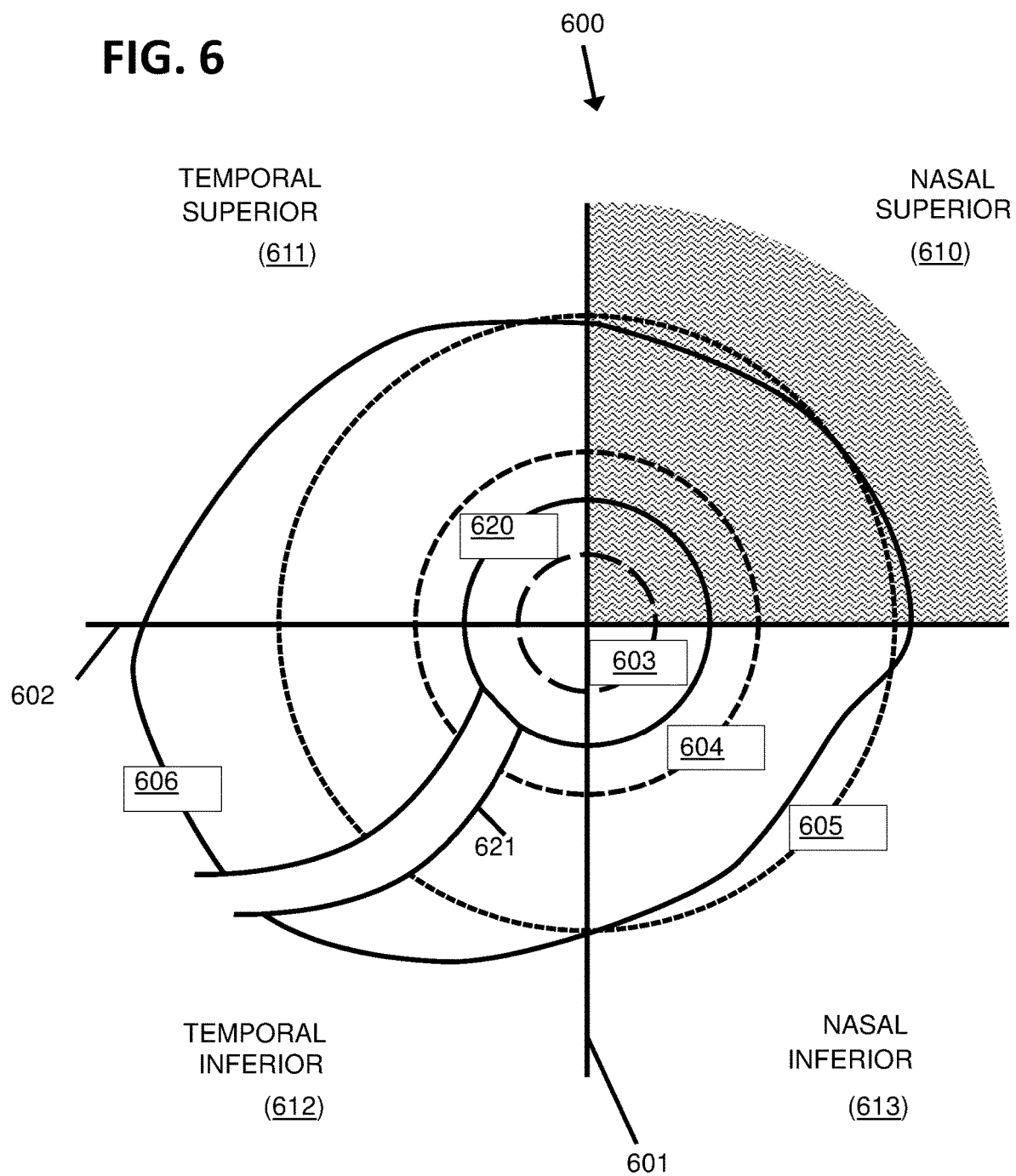
FIG. 6 shows a plot of the visual field of a user's left eye delineating preferred regions for routing an ocular support arm.

FIG. 6 shows a plot 600 of the extent of the field of vision 606 for a left eye of a subject. Vertical line 601 and horizontal line 602 intersect at the center of vision, corresponding to the fovea. Contours 603, 604, and 605 represent particular angular deviations away from the center of vision, each one a greater deviation from the center than the previous. For example, contour 603 represents a deviation of 10 degrees from the center of vision, contour 604 represents a 30 degree deviation, and contour 605 represents a 60 degree deviation. Regions of vision can be specified to lie within one of four quadrants. Those on the same side of vertical line 601 as the subject's nose are labeled "nasal", whereas those on the same side of vertical line 601 as the subject's left temple are labeled "temporal". Likewise, regions above horizontal line 602 are labeled "superior" whereas those below horizontal line 602 are labeled "inferior". The four regions are thus the nasal superior 610, temporal superior 611, temporal inferior 612, and nasal inferior 613. The outline of an ocular 620 is shown as centered upon the center of vision, though this is only a nominal position, and other positions near the center of vision are anticipated. Ocular 620 is supported by ocular support arm 621.

Embodiments of the present disclosure comprise an ocular, such as ocular 620, supported by an ocular support arm, such as support arm 621, that attaches to the ocular in such a way as to avoid occluding vision in the nasal superior region 610. The support arm has a more distal portion extending laterally beyond the ocular support location, a more proximal portion extending medially toward the head engagement member, and a central portion that extends between the distal and proximal portions beyond, or nearly beyond, the periphery of the user's vision. In some embodiments, the support arm may have multiple segments that are movable with respect to each other to change the position of the ocular it supports and to adjust the system to fit the user's head. Ocular support arms as described herein, from the point of view of the user, have the same advantages as those described with reference to FIG. 5: minimal obscuration of peripheral vision, especially in the sensitive area between and above the eyes, and the ability to adapt to a range of head widths.

Figure 7A:
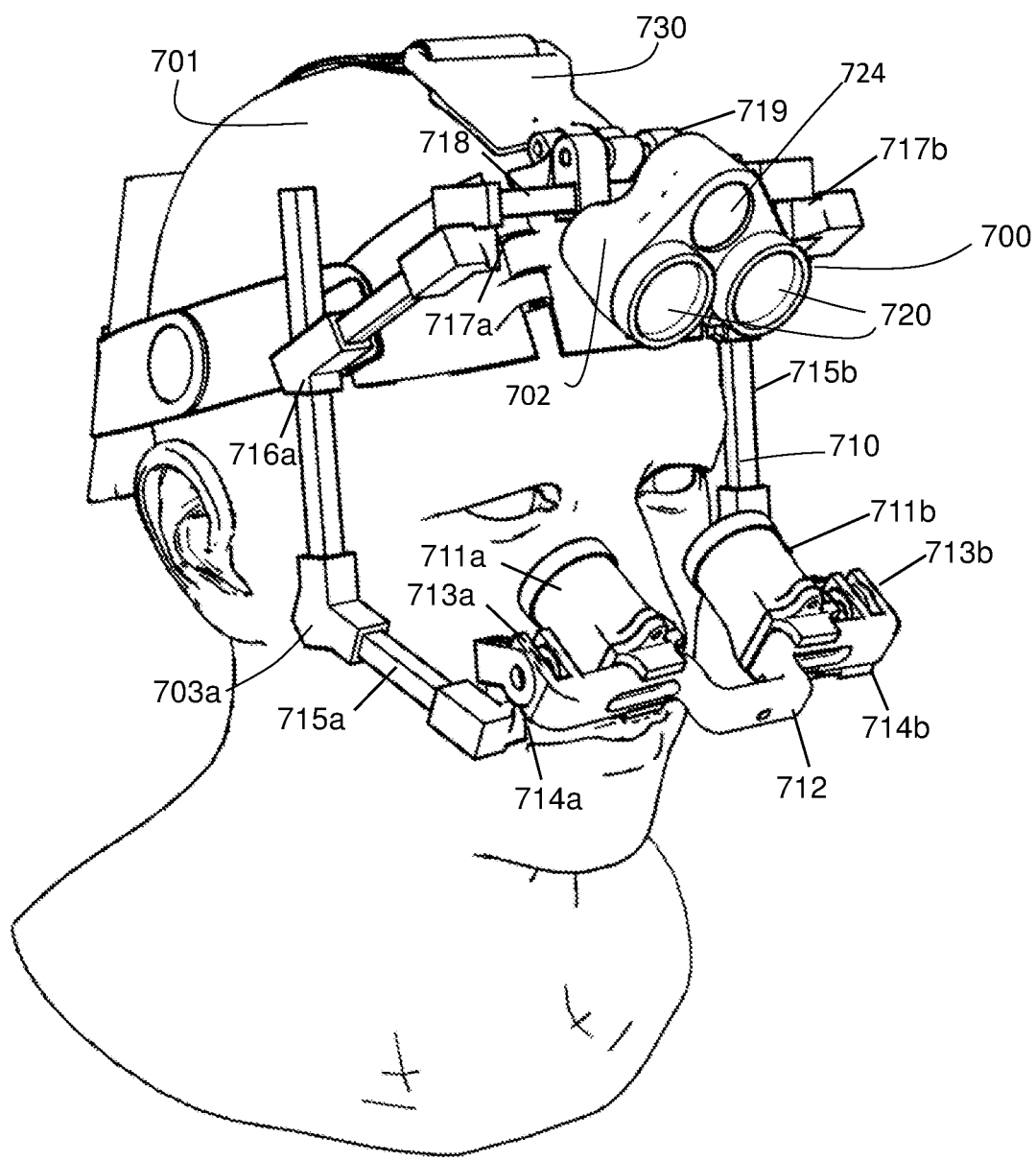
FIG. 7A is a perspective view of a digital loupe system.
Figure 7B:
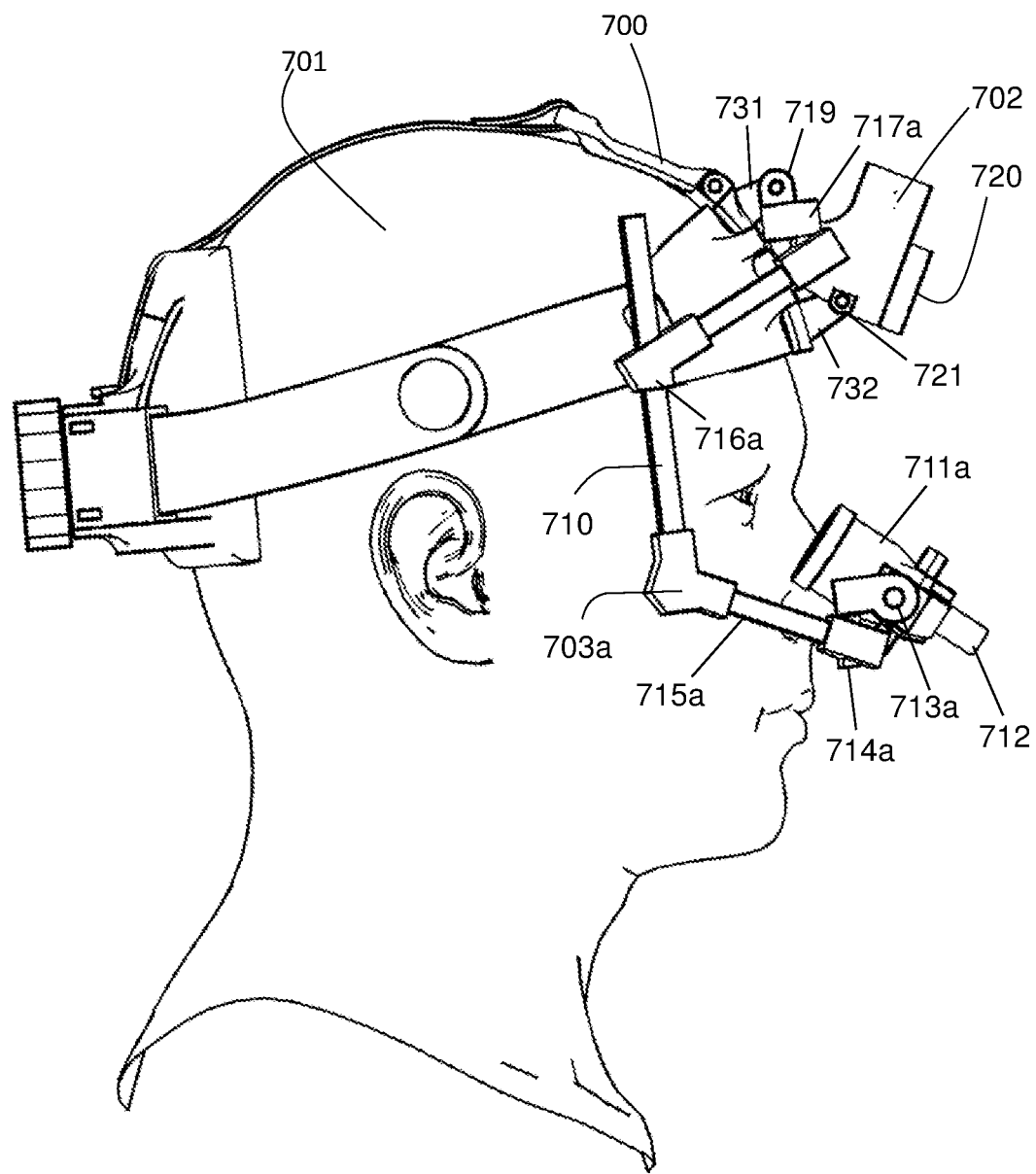
FIG. 7B is a side view of a digital loupe system.
Figure 7C:
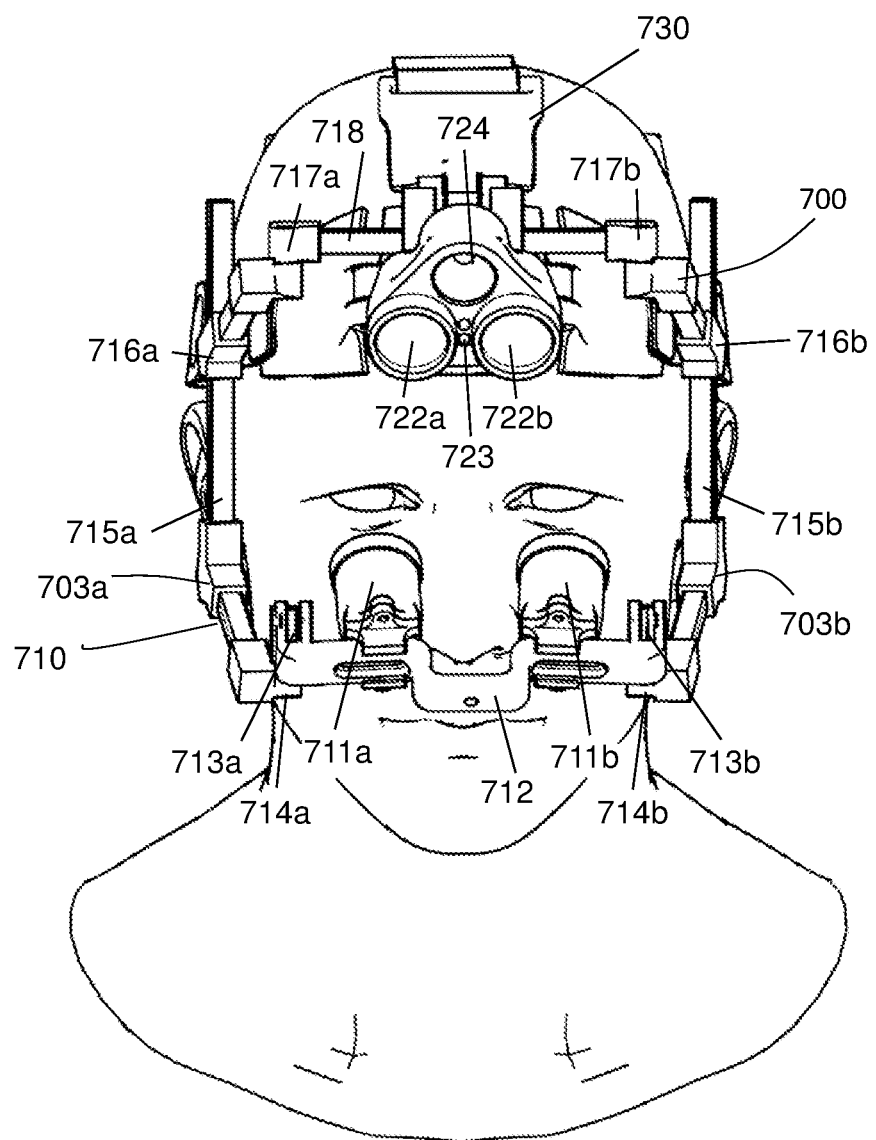
FIG. 7C is a front view of a digital loupe system.

FIGS. 7A-C depict an embodiment of a digital loupe system 700 as worn upon a user's head 701. The head mounting system of this embodiment may be used to support oculars other than digital loupe oculars. Portions of this head mounting system may also be used to support a single ocular using, e.g., a single ocular support arm and associated structure. FIG. 7A depicts a perspective view, FIG. 7B depicts a side view, and FIG. 7C depicts a front view. This embodiment comprises an adjustable binocular display and support structure 710 and a stereo camera pair 720 mounted on a head engagement member 730 on the user's head 701. The adjustable binocular display and support structure has a pair of oculars 711a and 711b supported by adjustable support arms that minimize interference with the user's vision, as described below. The stereo camera pair 720 is mounted in a housing 702 with an adjustable declension angle via rotational hinge 721 so that the cameras 722a,b in the camera pair 720 can be pointed in the desired direction toward, e.g., an object or work area. In addition to the stereo camera pair 720, a distance sensor 723 and an illumination source 724 are disposed in housing 702. The cameras 722a,b, distance sensor 723 and illumination source 724 all have optical axes that converge at a nominal working distance of the user, such as 50 cm. As described with respect to FIGS. 1-4 above, the cameras 722a,b and distance sensor 723 are controlled by a controller (not shown) to display on oculars 711a,b images of, e.g., a work area or object for viewing by the user wearing the device.

In this embodiment, the oculars 711a and 711b are supported by a segmented support arm structure which extends proximally from distal ocular support locations to the periphery of the user's vision by extending laterally, posteriorly, superiorly and medially before coupling to a head engagement member 730 in a position medial to the frontotemporales. In embodiments, the support structure includes an optional display bar to which the oculars are movably attached as well as a pair of support arms, which may comprise multiple articulations that allow for the adjustment of the lateral position of each ocular, e.g., to adapt to different user interpupillary distances; coupled adjustment of the vertical declension angles of the oculars; coupled adjustment of the vertical position of the oculars; and coupled adjustment of the eye relief distance of the oculars. Furthermore, the clearances between the support arms and the sides of the head may be adjustable.

Specifically, oculars 711a and 711b are both coupled to display bar 712 with slidable coupling mechanisms in order to adjust interpupillary distance. Display bar 712 forms an ocular support arm that is secondary to side support arms 715a,b, and is primarily obscured from the perspective of the user by oculars 711a,b, which may display images that extend at least to the edges of the oculars. A convergence angle of the oculars can be maintained independent of their sliding position, or adjusted with an additional articulation (not shown) that would rotate each ocular inward with respect to the other. Display bar 712 extends laterally from the oculars to connect to distal ends of side support arms 715a and 715b via hinges 713a,b and hinges 714a,b. Display bar 712 can rotate about hinges 713a,b to adjust a declension angle of the oculars. The declension angles of both oculars adjust together in this manner, avoiding divergence and thus avoiding double vision. Hinges 714a,b permit side support arms 715a,b to be moved toward and away from the side of the user's head.

In the embodiment shown in FIGS. 7A-C, side support arms 715a and 715b each have three straight segments connected by an angle connector 703a,b and a sliding connector 716a,b. In other embodiments, the side support arms may be unitary components that have straight and/or curved portions. Sliding connectors 716a,b enable adjustment of the vertical height of oculars 711a,b with respect to the user's head 701 by changing the effective height of side support arms 715a,b, i.e., changing the distance side support arms 715a,b extend inferiorly from the head engagement member. The side support arms 715a,b are rotationally connected via hinges 717a,b to a top support arm 718, which is coupled to the head engagement member 730 via rotational hinge 719. When the head engagement member is engaged with the user's head, rotational hinge 719 is medial to the user's frontotemporales. Like hinges 714a,b, hinges 717a,b permit side support arms 715a,b to be moved toward and away from the side of the user's head. The rotational axes of hinges 714a and 717a are nominally collinear, and the rotational axes of hinges 714b and 717b are nominally collinear, to enable movement of the side support arms 715a,b to adjust clearance between the side support arms and the side of the user's head. Eye relief, or the distance from oculars 711a,b to the user's face, is primarily adjusted via rotation of top support arm 718 about hinge 719, which results in movement of side support arms 715a,b and display bar 712 toward or away from the user's face. When the head engagement member 730 is engaged with the user's head, display bar 712 extends laterally from oculars 711a,b to side support arms 715a,b, and side support arms 715a,b extend posteriorly and superiorly from hinges 713a,b in positions at or beyond the periphery of the user's field of vision. Support arms 715a,b may also extend laterally if they have been rotated away from the user's head about hinges 714a,b and hinges 717a,b. Top support arm 718 extends medially from its connections to side support arms 715a,b to the head engagement member 730. Thus, this configuration enables the support arms to extend from the oculars to their connection to the head engagement member medial to the user's frontotemporales without extending through a region of the user's face medial and superior to a center of the user's eyes and inferior to the user's glabella.

Figure 8A:
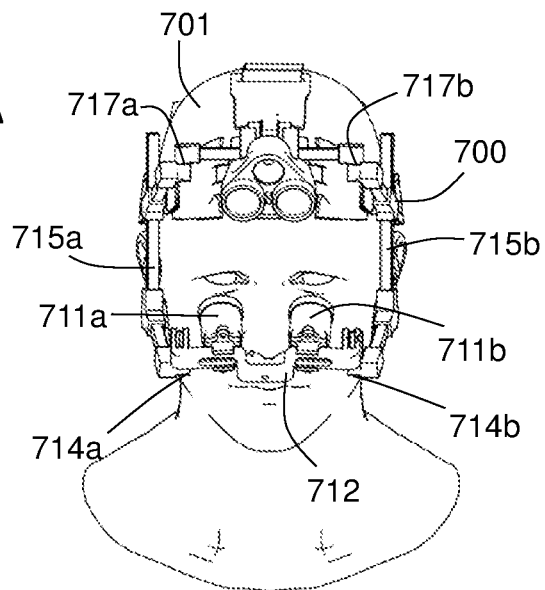
FIGS. 8A-8C show different articulation states of a digital loupe system.
Figure 8B:
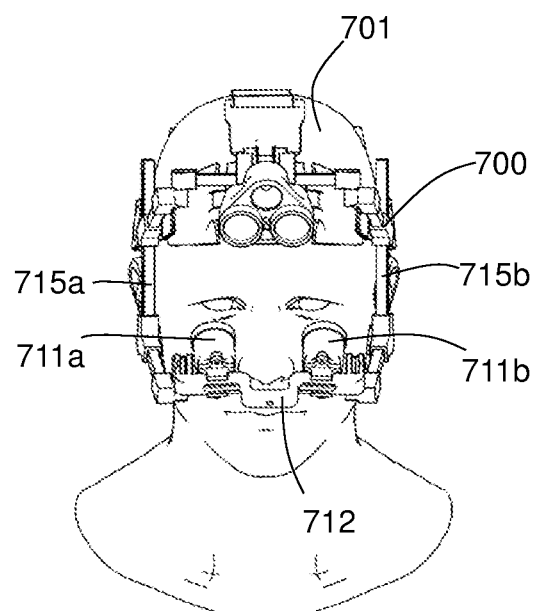
Figure 8C:
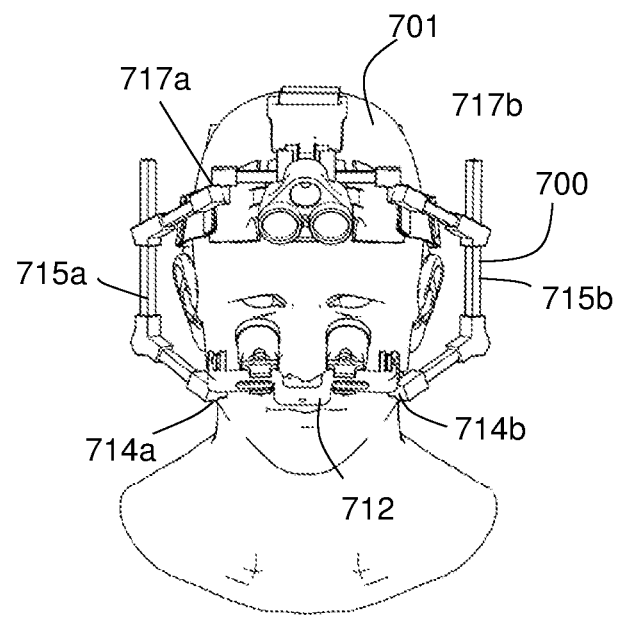

FIGS. 8A-8C show multiple articulation states of the embodiment of the digital loupe system 700 as shown in FIGS. 7A-C, with the forward view of the embodiment as shown in FIG. 7C reproduced for reference in FIG. 8A. FIG. 8B shows the system 700 adjusted to give the user a greater interpupillary distance with respect to the state shown in FIG. 8A, which can be effected by sliding the oculars 711a,b along the display bar 712. FIG. 8C shows the system 700 with a greater clearance between side arms 715a,b and the sides of the wearer's head 701 than the state shown in FIGS. 8A and 8B; this state involves a change in state of rotational hinges 714a,b and 717a,b.

Figure 9A:
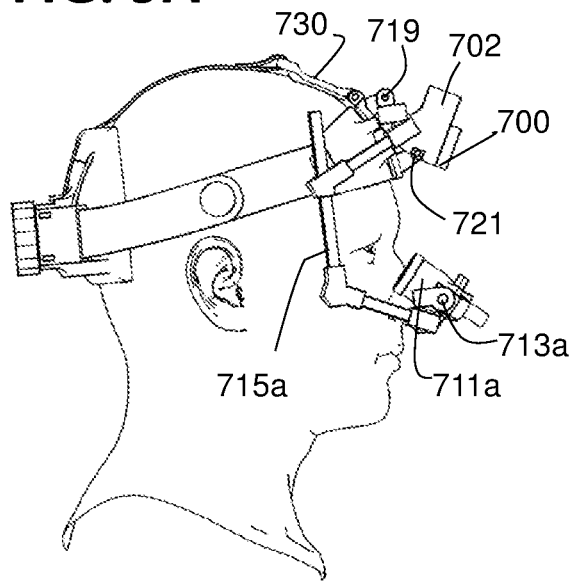
FIGS. 9A-9D show further different articulation states of a digital loupe system.
Figure 9B:
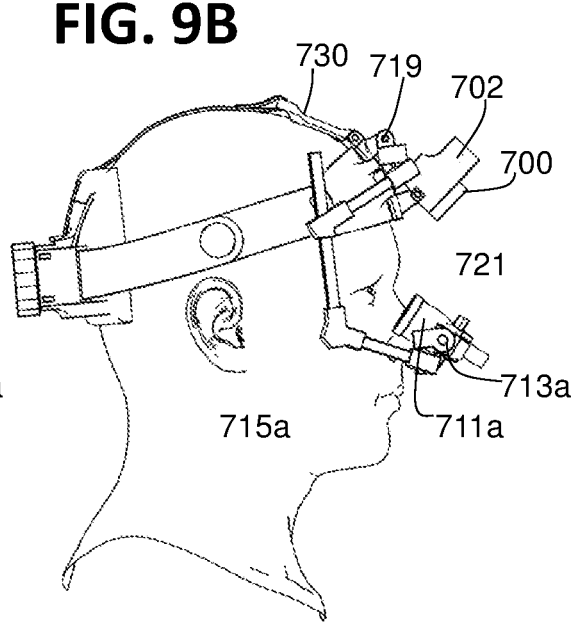
Figure 9C:
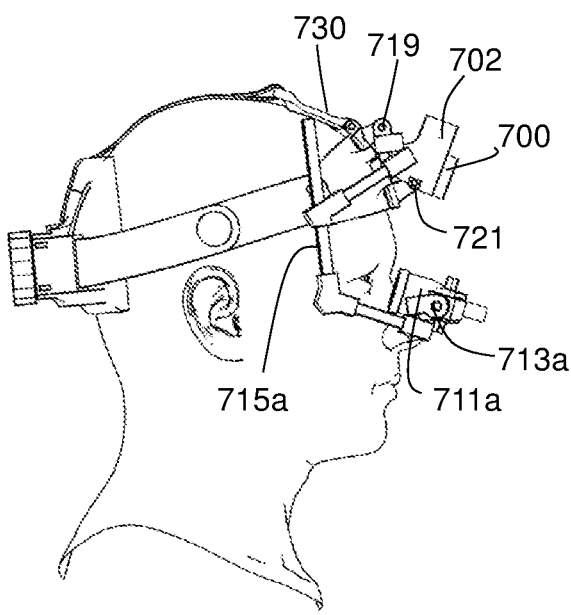
Figure 9D:
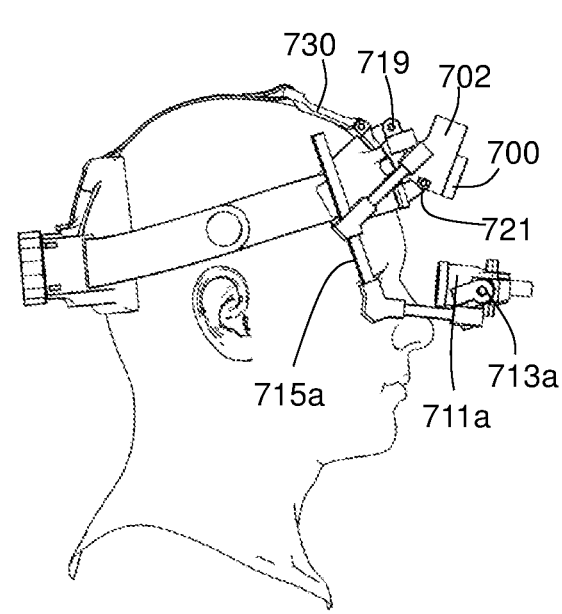

FIGS. 9A-9D show further multiple articulation states of the embodiment of the digital loupe system 700 as shown in FIGS. 7A-C, with the side view of the embodiment as shown in FIG. 7B reproduced for reference in FIG. 9A. FIG. 9B shows the system 700 adjusted to give the user an increased camera declension angle, effected by a rotation of housing 702 about hinge 721. FIG. 9C and FIG. 9D both show states in which the oculars of system 700 have decreased declension angles, with the configuration of FIG. 9D having less declension and more eye relief for the user than the state of FIG. 9C. Both of these states are reached by rotation of display bar 712 about hinges 713a,b, adjustment of side support arms 715a,b via slides 716a,b, and rotation of upper support arm 718 about hinge 719.

It should be appreciated that the different articulation states of FIGS. 8A-8C and 9A-9D are representative samples from a continuum of articulation states, and that surgeons can choose an articulation state that provides the best fit and ergonomics in terms of multiple factors, by intuitively adjusting the position and declension of the oculars. One way to capture the notion of "intuitive" in terms of adjustment of the position and declension of the oculars is the following. Each operating position as shown in FIGS. 8A-8C and 9A-9D comprise a particular state of each of the points of articulation, such as slides and hinges. The state of each articulation exists in a one-dimensional continuum, thus operating positions comprise points in a multidimensional space that is the product of each one-dimensional articulation range. An adjustment can be called intuitive if adjusting between two operating positions corresponds to traversing a straight line in this multidimensional space. Ideally, operating positions are uniquely defined by one point in this configuration space.

The flexibility afforded by the various articulations proffers multiple advantages, one of which is the ability to provide optimal ergonomics for a complete range of head shapes and sizes as well as operating styles. The interpupillary distance of oculars 711a,b can be adjusted to match that of any surgeon. Depending on how the supporting head engagement member 730 rests on the surgeon's head 701, the oculars 711a,b may differ in position relative to the surgeon's eyes even if all the articulations are in the same state—e.g., same slide position for sliding articulations, and same rotational position for rotational articulations. Therefore, the adjustment ranges of both the vertical position and the eye relief can be made large enough to take into account both the variation in how the head engagement member 730 might be supported on the surgeon's head 701, as well as a range of head shapes, sizes, and hairstyles (different hairstyles may cause the head engagement member 730 to sit differently on the surgeon's head 701). Also, a wider face can be accommodated by spreading out the side support arms 715a,b, as in the state shown in FIG. 8C versus the state shown in FIG. 8B.

Even for a given surgeon, the articulations confer flexibility of operating style. The adjustable height and declension of the oculars 711a,b, combined with the adjustable declension of the stereo camera pair 720, allows the surgeon to set up an operating posture whereby she can view the surgical field or work area directly with her eyes, and then with only a small eye rotation, concurrently view the magnified, or augmented, surgical field as displayed in the oculars 711a,b. The surgeon can adjust the height and declension of the oculars 711a,b depending on whether she chooses to view the unmagnified surgical field above the oculars with a slight upward eye rotation, or below the oculars with a slight downward eye rotation. The surgeon can choose to operate in a standing position or a sitting position by simple adjustment of the declension angle of the stereo camera pair 720 to redirect it toward the surgical field. If standing, it may be preferable to have a direct view of the surgical field below the oculars as opposed to above the oculars, as this maintains a more vertical cervical spine, thus decreasing the complications associated with forward head posture. The optical axes of the stereo camera pair 720 and the optical axes of the oculars 711a,b can be adjusted to converge together at a nominal working distance of a user, or they can be adjusted to diverge, such that the user can assume a more upright head position while still viewing a work area that is directed downward, by increasing the declension of the stereo camera pair 720.

A given surgeon may choose different articulations of side arms 715a,b in order to accommodate various eyeglasses or protective eyewear or face shields. It is also possible to incorporate a face shield directly into the frame 710 by attaching one or more transparent windows to the ocular support arms. The face shield can be constructed so as to leave the optical paths from the camera 720 to the surgical field, and from the user to the oculars 711a,b, unobstructed. It can also have segments attached to the side arms 715a,b in order to provide wraparound protection. It can be detached from the frame to be replaced with a different kind of face shield, for example one that incorporates laser filters to protect the eyes from different laser wavelengths that may be in use during the operation.

Figure 10A:
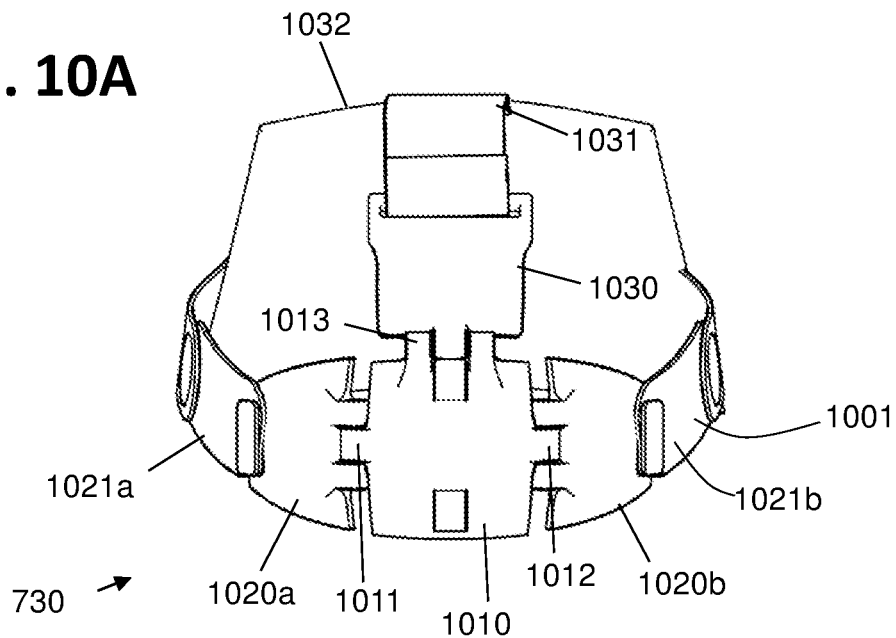
FIGS. 10A-10B show a segmented headband intended for use in a digital loupe system.
Figure 10B:
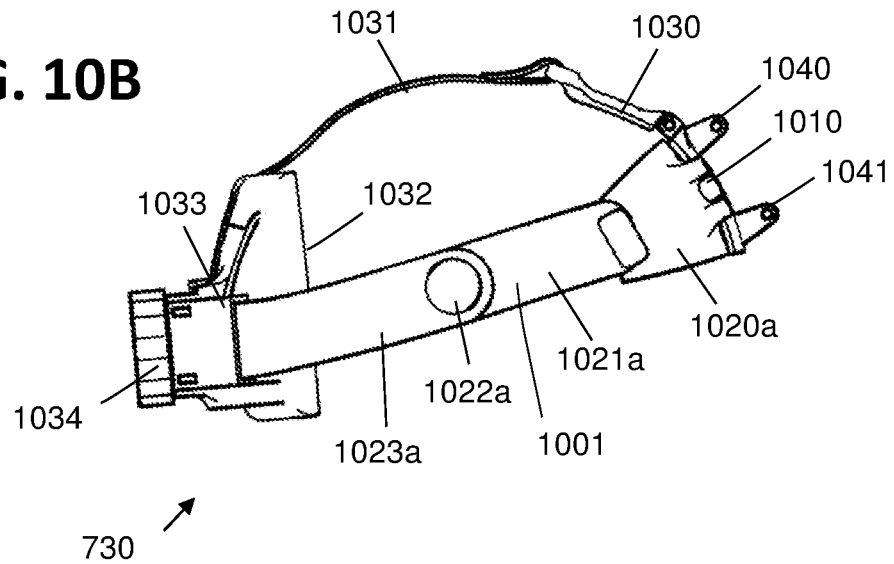

Features of head engagement member 730 are shown in FIGS. 10A-10B. Such a head engagement member has multiple inventive features that are useful especially to support the stereo camera pair and oculars of a digital loupe system, such as the digital loupe systems described above. Firstly, the head engagement member must accommodate ranges of head length, head circumference, slope and curvature of the front of the head, and slope and curvature of the back of the head. Also, it must provide a stable mounting platform for the stereo camera pair and the oculars that is rigidly and closely coupled to the skull of the surgeon, such that head movements of the surgeon directly translate to movements of these subsystems, without amplification or oscillation caused by long and/or finitely stiff lever arms.

Head engagement member 730 has an adjustable circumferential headband 1001 and an adjustable superior strap 1031. Back channel 1033 receives a pair of flexible bands including 1023a, which can be adjusted in length using actuator 1034, for example with a rack and spur gear mechanism, to adapt to variations in head circumference. Flexible support 1032 suspends the back of the head engagement member 730 over the back of the wearer's head, but it is conformable and flexible in order to adapt to different curvatures and slopes of the back of the head. The flexible bands including 1023a comprise a rotational attachment including 1022a that allows the angles of flexible headband extensions 1021a,b to change relative to the angles of the flexible bands including 1023a. This is to accommodate differences in relative slope of the front and back of the head, as the flexible extensions 1021a,b are rigidly coupled to headband pieces 1020a,b, which are made out of a more rigid material. Adjustable strap 1031 adapts to different head lengths and can be used both to help set the height at which center piece 1010 sits on the head, as well as to transfer weight (downward force) from objects mounted to it more toward the back of the head. Center piece 1010 has mounting points 1040 and 1041 for various attachments, such as a stereo camera pair and/or a support frame for oculars, as described above with respect to FIGS. 7A-C. Piece 1030 serves as an attachment point for strap 1031. Piece 1010 is designed to stably engage the user's head in order to support and maintain the stability of the stereo camera pair and ocular support subsystems attached to it. Note that piece 1010 is supported via tension from three directions to engage it with the user's head, that is, from the two sides and from the top.

Piece 1010 has a toroidal curvature that approximates the curvature of the average front of the head. It can include a thin layer of conformal material, such as gel or foam, that rests upon the head, without significantly decoupling it from motions of the head. Pieces 1020a,b also have a toroidal curvature that approximates the curvature of the average head where they would be located on such a head. They can also include a thin layer of conformal material as described above. These layers of conformal material serve to better match the shape of the wearer's head. Flexible couplings 1011, 1012, shown here as rotational hinges, between the side pieces 1020a,b and the center piece 1010, allow the combination of pieces to better match the curvature of a wearer's head over a larger distance, where deviations between the curvature of an average head and of the wearer's head would become more apparent. Thus, the segmented nature of the front of the head engagement member allows a larger surface to be rigidly and closely coupled to the user's head than a single piece could be, providing more support for distributing the weight of attachments, and thus more comfort.

It will be appreciated by those skilled in the art that depending on design intention, not all articulations of digital loupe system 700, including its head engagement member 730, are needed. The articulations could also be designed in different ways to achieve the same or similar degrees of freedom, and the support point for the ocular frame could be moved forward or backward on the skull, while still achieving all the aims of the present disclosure. FIGS. 11A-11D depict some aspects of a different embodiment of a digital loupe 1100 of the present disclosure in perspective view (FIG. 11A), front view (FIG. 11B), and side views (FIGS. 11C-D). The head mounting system of this embodiment may be used to support oculars other than digital loupe oculars. Portions of this head mounting system may also be used to support a single ocular using, e.g., a single ocular support arm and associated structure.

Figure 11A:
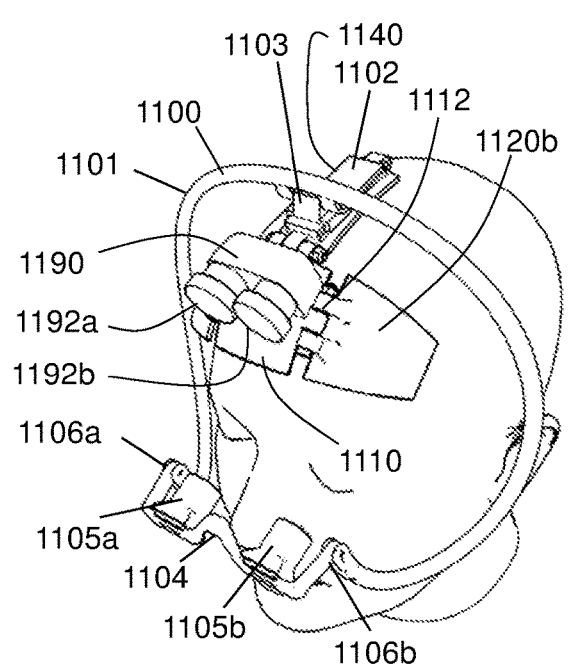
FIGS. 11A-11D depict different views and articulation states of an ocular support structure.
Figure 11B:
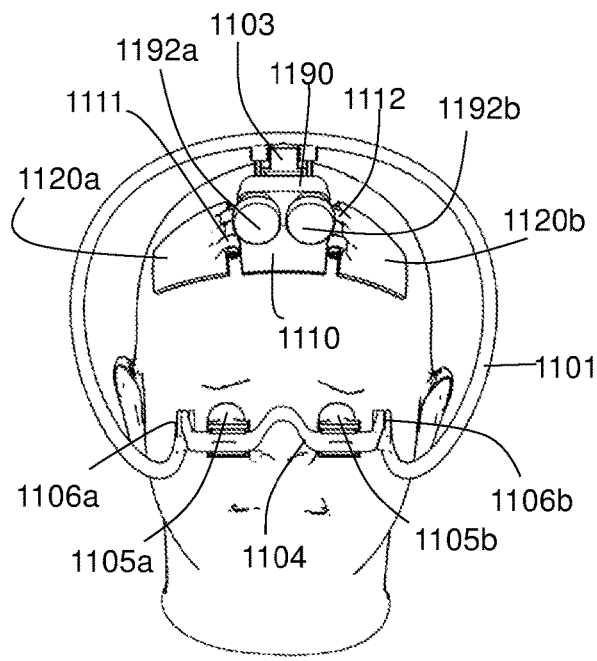
Figure 11C:
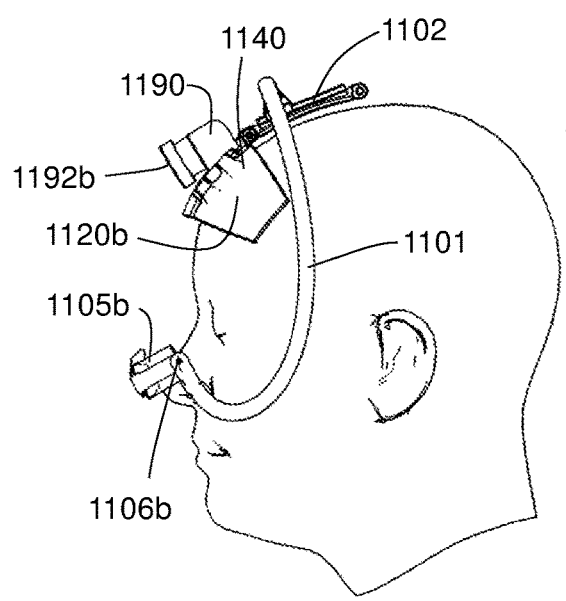
Figure 11D:
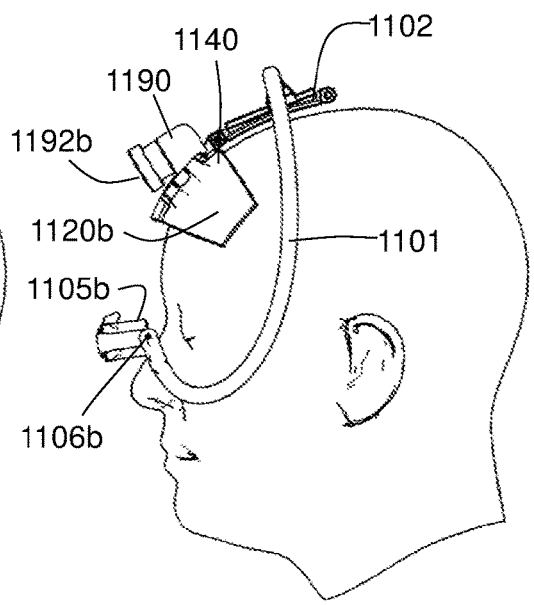

FIG. 11D depicts a different articulation state than the states in FIGS. 11A-C. Oculars 1105a,b are movably supported by display bar 1104 (e.g., via sliding connections permitting adjustment of the distance between the oculars, as described above), which is rotationally coupled via hinges 1106a and 1106b to a unitary, ram's horn-shaped support arm 1101.

A housing 1190 for a stereo camera pair 1192a,b is mounted on a center piece 1110 of a head engagement member 1140. A distance sensor (not shown) may also be disposed in housing 1190, as described with respect to the embodiments above. As in the embodiment of FIGS. 10A-B, center piece 1110 of head engagement member 1140 is designed to stably engage the user's head in order to support and maintain the stability of the stereo camera pair and ocular support subsystems attached to it. Piece 1110 has a toroidal curvature that approximates the curvature of the average front of the head. It can include a thin layer of conformal material, such as gel or foam, that rests upon the head, without significantly decoupling it from motions of the head. Side pieces 1120a,b, of the head engagement member 1140 connect to center piece 1110 via flexible couplings 1111 and 1112 (e.g., rotational hinges). Side pieces 1120a,b of the head engagement member 1140 also have a toroidal curvature that approximates the curvature of the average head where they would be located on such a head. They can also include a thin layer of conformal material as described above. These layers of conformal material serve to better match the shape of the wearer's head. Head engagement member 1140 may also have a headband and/or a superior strap, such as shown in FIGS. 10A-B.

A central portion of support arm 1101 connects to center piece 1110 of the head engagement member 1140 via a rotational hinge 1103 and a slider 1102 to achieve positional degrees of freedom for the support arm 1101 and the oculars supported by it in the vertical and eye relief dimensions. When the head engagement member 1140 is engaged with the user's head, rotational hinge 1103 and slider 1102 are medial to the user's frontotemporales. The oculars 1105a,b are supported by a movable display bar 1104, and the oculars connect to display bar 1104 in a manner that permits the distance between the oculars to be adjusted. As in the prior embodiment, together the display bar and support arm 1101 extend posteriorly, superiorly and medially from the ocular support positions. In this particular embodiment, display bar 1104 extends laterally and posteriorly from the oculars 1105a,b, and the two sides of support arm 1101 extend from their connections to the display bar 1104 in a three-dimensional curve inferiorly, posteriorly, and laterally; then superiorly, posteriorly and laterally; and finally, superiorly and medially toward hinge 1103 and slider 1102 of the head engagement member in positions at or beyond the periphery of the user's field of vision. Thus, this configuration enables the two sides of the unitary support arm to extend from the oculars to the connection to the head engagement member medial to the user's frontotemporales without extending through a region of the user's face medial and superior to a center of the user's eyes and inferior to the user's glabella.

FIG. 11D illustrates an articulation state differing from that in FIG. 11C in that the oculars 1105a,b are higher and closer to the eyes yet still within a line of sight of the eyes. This is accomplished with a different articulation state of hinge 1103, a different state of slide 1102, and a different state of hinges 1106a,b. Display bar 1104 and each of the two sides of unitary support arm 1101 extend laterally, posteriorly and superiorly (more specifically, inferiorly, posteriorly, and laterally; then superiorly, posteriorly and laterally; and finally, superiorly and medially) from the ocular 1105a or 1105b to beyond the edge of the user's peripheral vision, while avoiding the part of the face medial and superior to the pupils and below the glabella, before ultimately extending medially toward the center piece 1110 to be supported on top of the head, medial to the frontotemporales. The ram's horn shape of the support arm 1101 is such that the wearer can still use glasses or face shields, even for the widest faces, yet it rests primarily outside of the user's peripheral vision. Note that in FIGS. 11A-11D, 12A-12D, and 13A-13D the full support headband is not shown.

It should be clear that through considering variations of the shape of the support arm 1101, the mounting point proximal to the head could be more toward the back of the head or more toward the front of the head. A combination of two articulations at the mounting point, sliding and/or rotating, depending on the exact mounting position as well as other design considerations, could provide vertical and eye relief positioning of the oculars. The articulations for the different adjustments could also comprise slides and/or hinges on the support arm. For example, with respect to the embodiment of FIGS. 7A-C, the slides 716a,b of support arm 710 generally provide a vertical position adjustment for the oculars, but if the mounting point of the support arm is on the back of the head, similar slides can be used to adjust eye relief distance, whereas a rotational pivot point would provide primarily vertical adjustment capability. This kind of adjustment mechanism could be applied to the embodiment of FIGS. 11A-D. However, a mounting point toward the front of the head, as shown in FIGS. 7A-C, is generally preferable, as this provides a shorter, and hence more stable, support structure. Another way to adjust the interpupillary distance would be to have a sliding mechanism that allows adjustment of the width of the ocular support structure, for example, lengthening both display bar 1104 and support arm 1101 at their midpoint.

FIGS. 12A-12D depict an alternative embodiment of an ocular support structure supporting, e.g., a digital loupe system. The head mounting system of this embodiment may be used to support oculars other than digital loupe oculars. Portions of this head mounting system may also be used to support a single ocular using, e.g., a single ocular support arm and associated structure. In this embodiment, head engagement member 1210 has a shape adapted to fit a human head. As shown, head engagement member 1210 support a stereo camera pair 1292a,b. Rings 1220, 1221, and 1222 provide a connection to a headband and superior strap (not shown) to hold head engagement member 1210 against the user's head, such as shown in FIGS. 10A-B. A vertical slide 1202 and a hinge 1203 support a unitary support arm 1201 and can be used to adjust respectively the height and eye relief of oculars 1205a,b supported by the support arm 1201. A display bar 1204 supports the oculars 1205a,b, and a sliding connection between oculars 1205a,b and display bar 1204 allows adjustment of the oculars to accommodate a range of interpupillary distances, as described above. Hinges 1206a,b between display bar 1204 and support arm 1201 allow for adjustable and coupled declension angle of the oculars. FIG. 12D depicts a different articulation state than the views of FIGS. 12A-C, in which vertical slide 1202 and hinge 1203 have been adjusted to provide a more horizontal line of sight with more eye relief. Together, the display bar 1204 and the two sides of support arm 1201 extend from the oculars posteriorly, then laterally, superiorly, and medially in a partial rectangle shape to hinge 1203, which supports arm 1201, on to beyond the edge of peripheral vision, while avoiding the part of the face medial and superior to the pupils and below the glabella, before ultimately being supported on top of the head, medial to the frontotemporales.

FIGS. 13A-13D provide four views of yet another embodiment of a digital loupe system according to the present disclosure. The head mounting system of this embodiment may be used to support oculars other than digital loupe oculars. Portions of this head mounting system may also be used to support a single ocular using, e.g., a single ocular support arm and associated structure. Display bar 1304 supports the oculars 1305*a,b*. Display bar 1304 is coupled to distal ends of side support arms 1301*a* and 1301*b* via hinges 1306*a,b* to enable the declension angle of the oculars to be adjusted. A sliding connection between oculars 1305*a,b* and display bar 1304 allows adjustment of the oculars to accommodate a range of interpupillary distances, as described above. It should be noted that display bar 1304 as well as the display bars described previously provide additional stability to the oculars by connecting the full ocular support structure at the bottom as well as the top, i.e., by linking the distal ends of the support arms, in addition to their proximal linkages to the head engagement member.

A housing 1390 for a stereo camera pair 1392*a,b* is mounted on a center piece 1310 of a head engagement member. A distance sensor (not shown) and/or an illumination source (not shown) may also be disposed in housing 1390, as described with respect to the embodiments above. As in the embodiment of FIGS. 10A-B, center piece 1310 is designed to stably engage the user's head in order to support and maintain the stability of the stereo camera pair and ocular support subsystems attached to it. Piece 1310 has a toroidal curvature that approximates the curvature of the average front of the head. It can include a thin layer of conformal material, such as gel or foam, that rests upon the head, without significantly decoupling it from motions of the head. Side pieces 1320*a,b* of the head engagement member connect to center piece 1310 via flexible couplings (e.g., rotational hinges) as described above. Side pieces 1320*a,b* also have a toroidal curvature that approximates the curvature of the average head where they would be located on such a head. They can also include a thin layer of conformal material as described above. These layers of conformal material serve to better match the shape of the wearer's head.

Extending behind housing 1390 is a support arm engagement member 1330 mounted onto a linear slide 1321 in order to provide adjustment of an eye relief distance between oculars 1305*a,b* and a user's head. Support arm engagement member 1330 can slide upon linear slide 1321 in directions anterior and posterior with respect to housing 1390. Side support arms 1301*a,b* engage with support arm engagement member 1330 via sliders 1332*a,b*. Therefore, articulation of linear slide 1321 causes a change in anterior and posterior positioning of the oculars 1305*a,b*, and thus eye relief distance, due to their coupling to support arm engagement member 1330 through display bar 1304 and side support arms 1301*a,b*. Support arms 1301*a,b* can slide with respect to sliders 1332*a,b* to enable the effective length of support arms 1301*a,b* to be adjusted. The curved proximal sections of support arms 1301*a,b*, as well as the curve of sliders 1332*a,b*, follow a circle 1331 (shown in FIG. 13C) which has a center point a distance behind the user's eyes. By sliding the arms 1301*a,b* with respect to sliders 1332*a,b*, the oculars 1305*a,b* coupled to the arms 1301*a,b* via display bar 1304 also follow this circle, thus enabling adjustment of the height of the oculars 1305*a,b* with respect to the user's eyes. FIG. 13D shows a different articulation state of the positions of support arms 1301*a,b* with respect to support arm engagement member 1130 with a consequently higher position of oculars 1305*a,b* with respect to their positions as depicted in FIG. 13C. FIG. 13D also shows a different articulation state of support arm engagement member 1130 with respect to linear slide 1321 as compared to its articulation state depicted in FIG. 13C, with a consequent change in eye relief distance. Loupe declension angle is also adjusted into a different state in FIG. 13D by moving display bar 1304 about hinges 1306*a,b*. When the head engagement member is engaged with the user's head, sliders 1332*a,b* are medial to the user's frontotemporales. Together, the display bar 1304 and the support arms 1301*a,b* extend from their connections to the oculars laterally, posteriorly, and superiorly, then medially toward support arm engagement member 1330 in positions at or beyond the periphery of the user's field of vision. Thus, the ocular support structure of FIGS. 13A-D extends from the oculars to the connection to the head engagement member medial to the user's frontotemporales without extending through a region of the user's face medial and superior to a center of the user's eyes and inferior to the user's glabella.

Figure 14:
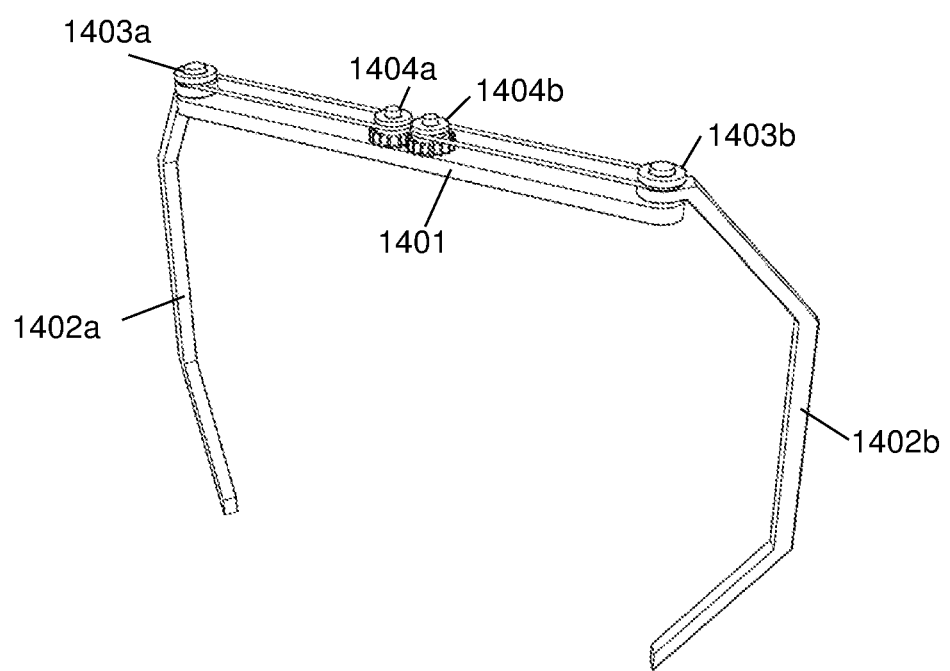
FIG. 14 depicts coupled side arms of an ocular support structure.

FIG. 14 shows a way to couple together the rotational state of two side support arms 1402*a,b* of a head-mounted ocular support. Side support arms 1402*a,b* are analogous to arms 715*a,b*, and a change in rotational state, analogous to the difference between articulation states shown in FIGS. 8B and 8C is contemplated. A change in the rotational state of one of arms 1402*a,b* rotates respectively pulleys 1403*a,b*, which sit atop rigid member 1401. Rotation of one of 1403*a,b* is transferred to the other of the two in the opposing direction. Here, the mechanism that transfers the rotational motion is a set of meshing gears 1404*a,b* connected to pulleys 1403*a,b* via belts or pushrods. Rotational encoders and motors can also be used to measure the articulation state of one side arm 1402*a,b* and actuate the other to match. This mechanism can be used, e.g., when there is no structure between a pair of oculars (e.g., the portion of display bar 712 between oculars 711*a,b* in FIGS. 7A-C) requiring the oculars to be moved together.

Figure 15:
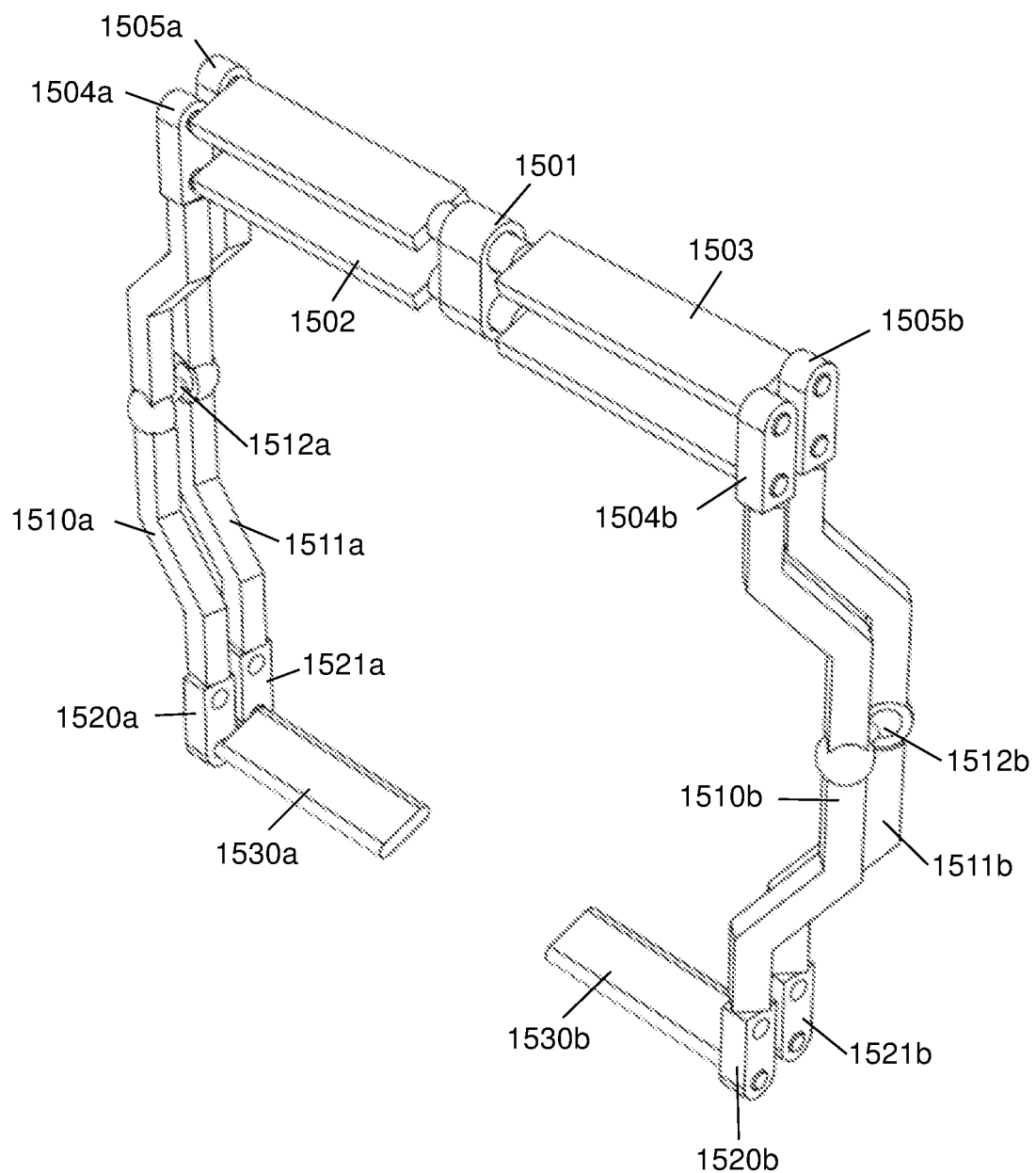
FIG. 15 depicts part of an ocular support structure with ocular declension coupled through the top member.

FIG. 15 depicts a support arm structure with ocular supports 1530*a,b* such that adjusting the declension angle of one ocular support automatically adjusts the declension angle of the other to match. This mechanism can be used when there is no structure between a pair of oculars (e.g., the portion of display bar 712 between oculars 711*a,b* in FIGS. 7A-C) requiring the oculars to be moved together. Part 1501 rotationally supports parts 1502 and 1503, and is itself rigidly coupled to the head of the user. Parts 1502 and 1503 remain parallel as they are rotationally connected to linkages 1504*a,b* and 1505*a,b*. Side support arms 1510*a,b* and 1511*a,b* can swivel about linkages 1504*a,b* and 1505*a,b* respectively, and 1520*a,b* and 1521*a,b* respectively, to adjust their clearance with the head of the user. The rotational state of arms 1510*a* and 1511*a* can be coupled through pin 1512*a* that mates with a ball joint to each arm; similarly for arms 1510*b* and 1511*b* through pin 1512*b*. Ocular supports 1530*a,b* are rotationally coupled to parts 1520*a,b* and 1521*a,b* respectively, and due to parallel linkages, the declension angle of ocular supports 1530*a,b* must be the same as parts 1502 and 1503, hence adjusting the declension of one ocular results in the same declension of the other ocular. Alternatively, as above, the declension angles of the two oculars can be coupled via a sensor/actuator pair.

Each of the articulations described in this disclosure could be manually or automatically actuated, for example with a motor. Each may include a sensor to determine its state, for feedback and control purposes, or simply to track usage. As described previously, knowing the relative positions and orientations of different subsystems of the digital loupe system, for example, the different declension states of the camera and/or oculars as well as the distance between them, could enable compensation of the vertical parallax, or at least the average vertical parallax, that changes as a function of distance away from the surgical field.

Additional articulations or articulation ranges not yet described are envisioned as aspects of the present disclosure. For example, the disclosure could comprise an articulation or articulation range that removes the oculars and/or ocular support structure substantially or completely from the user's field of view. This could be done in the case of digital loupe system 700 of FIGS. 7A-C by articulating hinge 719 such that ocular support structure 710 lifts out of the field of vision of the user. Similarly, for system 1100 of FIGS. 11A-D, hinge 1103 could be brought into a state that lifts the oculars 1105*a,b* and support arms 1101, 1104 completely out of the field of vision. One can envision a track system like tracks at the ends of arms 1301*a,b*, that insert into slots like 1302*a,b* with enough range to lift the oculars and ocular support structures completely out of view.

Figure 16A:
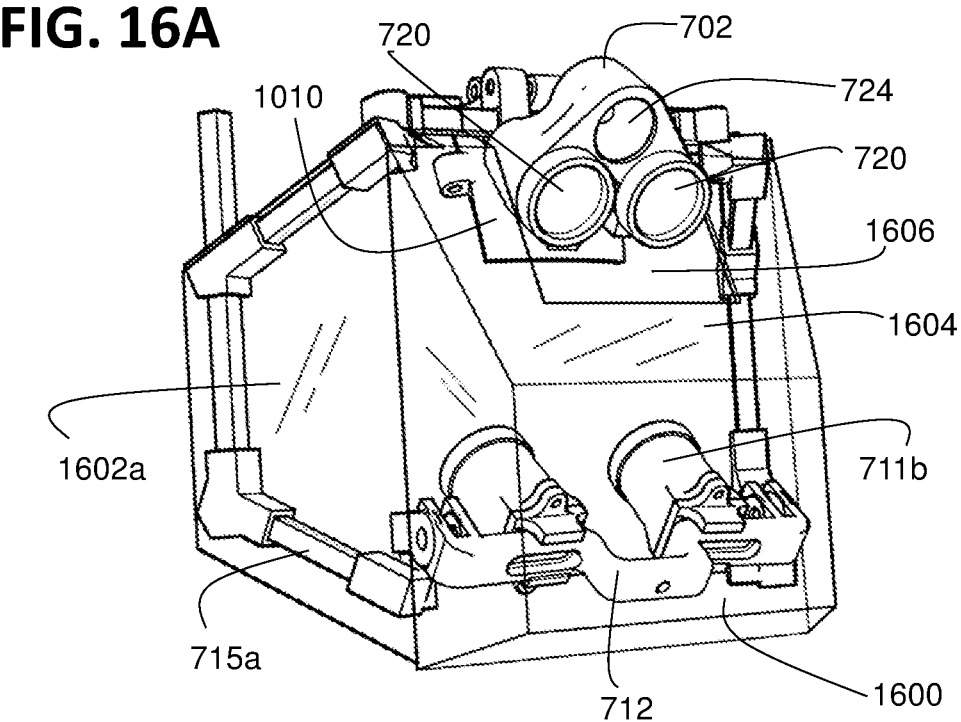
FIGS. 16A-B illustrate a face shield that can be used with the digital loupe system of this invention.
Figure 16B:
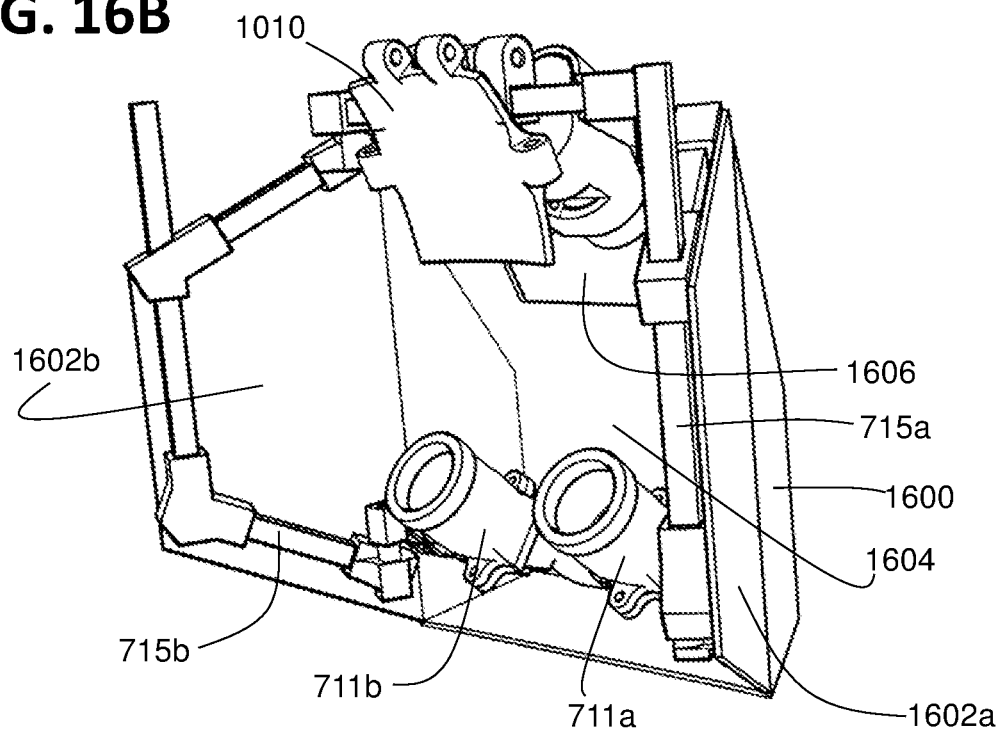

FIGS. 16A-B show a face shield or window that may be used with the digital loupe system of FIGS. 7A-10B. For clarity, FIGS. 16A-B omit all but central plate 1010 of the head engagement member of this embodiment. A front face shield plate 1600 cooperates with side face shield plates 1602*a* and 1602*b* to protect the user's face while wearing the digital loupe system. Side face shield places 1602*a,b* are coupled to portions of side support arms 715*a,b* at their top to maintain the freedom to adjust the height of said support arms. Face shield plates 1602*a,b* articulate together with side support arms 715*a,b*, respectively, to adjust the distance between the face shield plates and the user's face in concert with the same adjustment made to the side support arms 715*a,b*. As shown, face shield plate 1600 has five facets, including a sloped front facet 1604 with a cutout 1606 that permits cameras 720 and distance sensor 724 to view an object or work area without interference from the face shield. Face shield plate 1600 may connect at the top with a hinge permitting it to be tilted upward. In other embodiments, the face shield may have fewer components or facets, as well as alternative means of coupling to ocular support arms and/or head engagement structures. A face shield may be added to any of the other digital loupe system or ocular support systems described above.

Digital loupe controls, such as those used for magnification change, or starting and stopping a video recording, could be actuated via buttons placed on the ocular support arms. This is useful because ocular support arms are easily draped to provide sterility; parts of the ocular support structure may already need to be draped to enable the surgeon to adjust various articulations intraoperatively. However, articulations that are driven by motors or other actuators may be commanded to different positions in a hands-free manner via voice or gesture or other means of issuing commands to a digital system.

Placement of digital loupe system components, such as batteries, at the back of the head can be used to counterweight components such as the stereo camera pair and the oculars. The oculars can include built-in heaters, or structures to transfer heat dissipated from displays or other electronics, to keep them warm enough to prevent fogging from the user's breath.

The processor of the digital loupe system can comprise additional peripherals that may enhance the system's functionality. For example, it could comprise a wired or wireless interface for sending video signals to and from the head-mounted display, such that live video can be streamed from one digital loupe system to another, or to a server for recording or streaming to remote locations, or from a server for playback. A teaching surgeon at a remote location could use such a setup to mark up the field of view of the operating surgeon who may be a trainee, or to telestrate, and indicate points of interest. Various functions may be assisted by the presence of a motion sensing unit such as an accelerometer, gyroscope, and/or magnetometer.

For purposes of this disclosure, the term "processor" is defined as including, but not necessarily being limited to, an instruction execution system such as a computer/processor based system, an Application Specific Integrated Circuit (ASIC), a computing device, or a hardware and/or software system that can fetch or obtain the logic from a non-transitory storage medium or a non-transitory computer-readable storage medium and execute the instructions contained therein. "Processor" can also include any controller, state-machine, microprocessor, cloud-based utility, service or feature, or any other analogue, digital and/or mechanical implementation thereof. When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of viewing a work area, comprising:
engaging a head engagement member with a user's head, the head engagement member supporting first and second cameras above the user's head;
placing a first ocular in a line of sight with a first eye of the user and a second ocular in a line of sight with a second eye of the user, the first and second oculars supported by a distal portion of first and second support arms, respectively, positioned such that a central portion of each support arm extends laterally and superiorly from its respective distal portion toward a proximal portion of the support arm without extending through a region of the user's face medial and superior to the user's eyes and inferior to the user's glabella;
supporting the proximal portion of each of the first and second support arms at a position of the head engagement member medial to the central portion of the first and second support arms, respectively, such that the central portion and the distal portion do not engage the head engagement member or the user's head; and
displaying in the first and second oculars images of the work area obtained by the first and second cameras, respectively.

2. The method of claim 1 wherein the supporting step comprises supporting the proximal portion of each of the first and second support arms at a position of the head engagement member medial to the user's frontotemporales.

3. The method of claim 1 wherein the central portion of each support arm also extends posteriorly from the distal from the first and second oculars toward the head engagement member without extending through a region of the user's face medial and superior to the user's eyes and inferior to the user's glabella when the head engagement member is engaged with the user's head.

4. The method of claim 1 further comprising viewing the work area along a line of sight extending over the first and second oculars.

5. The method of claim 1 further comprising viewing the work area along a line of sight extending under the first and second oculars.

6. The method of claim 1 further comprising viewing the work area simultaneously through the first and second oculars and around the first and second oculars.

7. The method of claim 1 further comprising moving the first and second oculars upward with respect to the user's eyes.

8. The method of claim 1 further comprising moving the first and second oculars downward with respect to the user's eyes.

9. The method of claim 1 further comprising changing a distance between the first and second oculars.

10. The method of claim 1 further comprising adjusting a shape of the head engagement member to fit the user's head.

11. The method of claim 1 further comprising moving at least one of the first support arm and the second support arm medially or laterally.

12. The method of claim 1 further comprising moving the first and second support arms above the user's eyes.

13. The method of claim 1 further comprising obtaining a measurement of distance from the first and second cameras to the work area and applying a transformation to images obtained by the first and second cameras to create transformed images, the displaying step comprising displaying the transformed images on the first and second oculars.

14. The method of claim 13 wherein the step of obtaining a measurement of distance from the first and second cameras to the work area is performed by using a distance sensor supported by the head engagement member.

15. The method of claim 13 wherein the step of applying the transformation comprises virtually adjusting the convergence angle of the first and second oculars.

16. The method of claim 13 wherein the step of applying a transformation comprises causing the first and second images to appear on the first and second oculars as if the first and second cameras had optical axes that converge at a distance corresponding to the measurement of distance.

17. The method of claim 1 further comprising illuminating the work area.

18. The method of claim 17 further wherein the illuminating step comprises determining an illumination parameter based upon the measurement of distance and illuminating the work area based on the illumination parameter.

19. The method of claim 18 wherein the illuminating step comprises pulsing an illumination source in a manner synchronized with an exposure interval of the first and second cameras.

20. The method of claim 1 further comprising moving at least one of the first and second support arms automatically.

21. The method of claim 1 further comprising automatically moving at least part of the second support arm in response to movement of a corresponding part of the first support arm.

* * * * *